US006908994B1

(12) United States Patent
Rich et al.

(10) Patent No.: US 6,908,994 B1
(45) Date of Patent: Jun. 21, 2005

(54) COLLAGEN-BINDING PROTEINS FROM ENTEROCOCCAL BACTERIA

(75) Inventors: Rebecca L. Rich, Salt Lake City, UT (US); Bernd Kriekemeyer, Ulm (DE); Rick T. Owens, Stewartsville, NJ (US); Magnus Hook, Houston, TX (US); Barbara E. Murray, Houston, TX (US); Sreedhar R. Nallapareddy, Houston, TX (US); George M. Weinstock, Houston, TX (US)

(73) Assignees: The Texas A&M University System, College, Station, TX (US); Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 09/568,470

(22) Filed: May 10, 2000

Related U.S. Application Data
(60) Provisional application No. 60/133,334, filed on May 10, 1999.

(51) Int. Cl.[7] ......................... C07H 21/04; C07H 21/02; A61K 39/00; A61K 39/02
(52) U.S. Cl. .................. 536/23.7; 536/23.1; 424/184.1; 424/190.1; 424/234.1
(58) Field of Search ............................. 514/2; 530/350, 530/388.2; 424/242.1

(56) References Cited

U.S. PATENT DOCUMENTS 6,617,156 B1 * 9/2003 Doucette-Stamm et al. ...... 435/320.1

FOREIGN PATENT DOCUMENTS

| WO | WO 85/05553 | 12/1985 |
|----|----|----|
| WO | WO 92/07002 | 4/1992 |
| WO | WO 97/43314 | 11/1997 |
| WO | WO 9850555 A2 * | 11/1998 |
| WO | WO 98/50555 | * 11/1998 |

OTHER PUBLICATIONS

Patti et al, The Journal of Biological Chemistry, vol. 267, No. 7, Mar. 1992, p. 4766–4772.*
Zareba et al, Current Microbiology vol. 34, 1997, p. 6–11.*
Gillaspy et al, Gene 196, 1997, 239–248.*
Smeltzer et al, (Gene 196, 1997, 249–259).*
Smeltzer et al, Gene 196 (1997) 249–259.*
Patti et al., Critical Residues in the Ligand–binding Site of the *Staphylococcus aureus* Collagen–binding Adhesin (MSCRAMM), The Journal of Biological Chemistry, vol. 270, No. 20, Issue of May 19, pp. 12005–12011, 1995.
Patti et al., Identification and Biochemcial Characterization of the Ligand Binding Domain of the Collagen Adhesion from *Staphylococcus aureus*, Biochemistry, vol. 32, No. 42, pp. 11428–11435, 1993.

Smeltzer et al., Comparative Evaluation of Use of *cna*, *fnbA*, *fnbB*, and *hlb* for Genomic Fingerprinting in the Epidemiological Typing of *Staphylococcus aureus*, Journal of Clinical Microbiology, vol. 35, No. 10, Oct. 1997, pp. 2444–2449.
Mohamed et al., Inhibition of *Staphylococcus aureus* Adherence to Collagen under Dynamic Conditions, Infection and Immunity, vol. 67, No. 2, Feb. 1999, pp. 589–594.
Clark et al., The effect of growth temperature on *Staphyloccocus aureus* binding to type I collagen, Microbial Pathogenesis 1994; 17:239–251.
Rich et al., Domain Structure of the *Staphylococcus aureus* Collagen Adhesin, Biochemistry 1998, 37, 15423–15433.
Gillaspy et al., The *Staphylococcus aureus* collagen adhesin–encoding gene (*cna*) is within a discrete genetic element, Gene 196 (1997) 239–248.
Smeltzer et al., Prevalence and chromosomal map location of *Staphylococcus aureus* adhesin genes, Gene 196 (1997) 249–259.
Gillaspy et al., Factors Affecting the Collagen Binding Capacity of *Staphylococcus aureus*, Infection and Immunity, vol. 66, No. 7, Jul. 1998, p. 3170–3178.
Nilsson et al., Vaccination with a Recombinant Fragment of Collagen Adhesin Provides Protection against *Staphylococcus aureus*–mediated Septic Death, J. Clin. Invest., vol. 101, No. 12, Jun. 1998, pp. 2640–2649.
Switalski et al., Collagen Receptor of *Staphylococcus aureus*, pp. 101–115.

(Continued)

Primary Examiner—Lynette R. F. Smith
Assistant Examiner—Vanessa L. Ford
(74) Attorney, Agent, or Firm—Stites & Harbison PLLC; B. Aaron Schulman

(57) ABSTRACT

A collagen-binding MSCRAMM entitled Ace from enterococcal bacteria is provided which was homologous to the ligand-binding region of Cna, the collagen-binding MSCRAMM from *Staphylococcus aureus*, and which can be utilized in a similar manner as other collagen-binding MSCRAMMs to inhibit adhesion of enterococcal bacteria to extracellular matrix proteins. The N-terminal region of Ace contained a region (residues 174–319), or A domain, which appears to be equivalent to the minimal ligand-binding region of the collagen-binding protein Cna (Cna 151-318), and contains several 47-residue tandem repeat units, called B domain repeat units, between the collagen-binding site and cell wall-associated regions. The Ace protein of the invention can thus be utilized in methods of preventing and/or treating enterococcal infection, and in addition, antibodies raised against Ace, or its A domain, can be used to effectively inhibit the adhesion of enterococcal cells to a collagen substrate. The Ace protein of the present invention is thus a functional collagen-binding MSCRAMM and can be utilized to treat or prevent invention in the same manner as other isolated MSCRAMMs have been utilized, namely in methods of treating or preventing infections and diseases caused by enterococcal bacteria.

4 Claims, 16 Drawing Sheets

OTHER PUBLICATIONS

Figure 2A:

Switalski et al., Isolation and Characterization of a Putative Collagen Receptor from *Staphylococcus aureus* Strain Cowan 1*, The Journal of Biological Chemistry, vol. 264, Nos. 35–36, 1989, pp. 20823–22078.

Patti et al., MSCRAMM–Mediated Adherence of Microorganisms to Host Tissues, Annu. Rev. Microbiol. 1994, 48:585–617.

Patti et al., Microbial adhesins recognizing extracellular matrix macromolecules, Current Opinion in Cell Biology, 1994, 6:752–758.

Xiao et al., Conditional adherence of *Enterococcus faccalis* to extracellular matrix proteins, FEMS Immunology and Medical Microbiology 21 (1998) 287–295.

Patti et al., Molecular Characterization and Expression of a Gene Encoding a *Staphylococcus aureus* Collagen Adhesin, The Journal of Biological Chemistry, vol. 267, No. 7, Issue of Mar. 5, pp. 4766–4772 (1992).

* cited by examiner

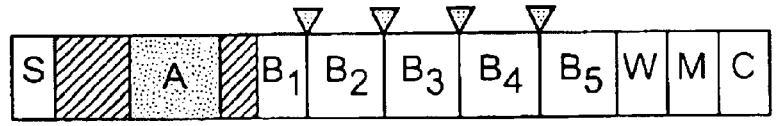
FIG. 1A
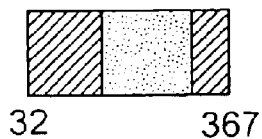
FIG. 1B
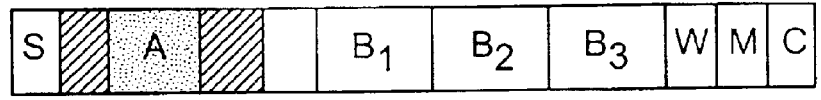
FIG. 1C
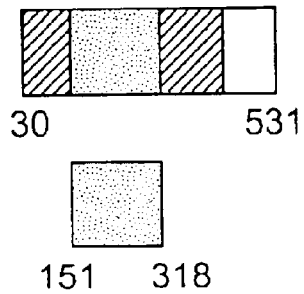
FIG. 1D
```
R D Y P F F Y K V G D L A G E S N Q V R
W F L N V N L N K S D V T E D I S I A D
R Q G S G Q Q L N K E S F T F D I V N D
K E T K Y I S L A E F E Q Q G Y G K I D
F V T D N D F N L R F Y R D K A R F T S
F I V R Y T S T I T E A G Q H Q A T F E
N S Y D I N Y Q L N N Q D A T N E K N T
S Q V K N V
```
FIG. 1E

FIG. 12A FIG. 12B FIG. 12C

SEQUENCE LISTING

<160> NUMBER OF SEQ ID NOS: 31

<210> SEQ ID NO 1
<211> LENGTH: 458
<212> TYPE: PRT
<213> ORGANISM: Enterococcus faecalis

<400> SEQUENCE: 1

```
Glu Leu Ser Lys Ser Ser Ile Val Asp Lys Val Glu Leu Asp His Thr
1               5                  10                  15

Thr Leu Tyr Gln Gly Glu Met Thr Ser Ile Lys Val Ser Phe Ser Asp
            20                  25                  30

Lys Glu Asn Gln Lys Ile Lys Pro Gly Asp Thr Ile Thr Leu Thr Leu
        35                  40                  45

Pro Asp Glu Leu Val Gly Met Thr Glu Asn Asp Gly Ser Pro Arg Lys
    50                  55                  60

Ile Asn Leu Asn Gly Leu Gly Glu Val Phe Ile Tyr Lys Asp His Val
65                  70                  75                  80

Val Ala Thr Phe Asn Glu Lys Val Glu Ser Leu His Asn Val Asn Gly
                85                  90                  95

His Phe Ser Phe Gly Ile Lys Thr Leu Ile Thr Asn Ser Ser Gln Pro
            100                 105                 110

Asn Val Ile Glu Thr Asp Phe Gly Thr Ala Thr Ala Thr Gln Arg Leu
```

```
                115                 120                 125
Thr Ile Glu Gly Val Thr Asn Thr Glu Thr Gly Gln Ile Glu Arg Asp
            130                 135                 140

Tyr Pro Phe Phe Tyr Lys Val Gly Asp Leu Ala Gly Glu Ser Asn Gln
145                 150                 155                 160

Val Arg Trp Phe Leu Asn Val Asn Leu Asn Lys Ser Asp Val Thr Glu
                165                 170                 175

Asp Ile Ser Ile Ala Asp Arg Gln Gly Ser Gly Gln Gln Leu Asn Lys
            180                 185                 190

Glu Ser Phe Thr Phe Asp Ile Val Asn Asp Lys Glu Thr Lys Tyr Ile
        195                 200                 205

Ser Leu Ala Glu Phe Glu Gln Gln Gly Tyr Gly Lys Ile Asp Phe Val
    210                 215                 220

Thr Asp Asn Asp Phe Asn Leu Arg Phe Tyr Arg Asp Lys Ala Arg Phe
225                 230                 235                 240

Thr Ser Phe Ile Val Arg Tyr Thr Ser Thr Ile Thr Glu Ala Gly Gln
                245                 250                 255

His Gln Ala Thr Phe Glu Asn Ser Tyr Asp Ile Asn Tyr Gln Leu Asn
            260                 265                 270

Asn Gln Asp Ala Thr Asn Glu Lys Asn Thr Ser Gln Val Lys Asn Val
        275                 280                 285

Phe Val Glu Gly Glu Ala Ser Gly Asn Gln Asn Val Glu Met Pro Thr
    290                 295                 300

Glu Glu Ser Leu Asp Ile Pro Leu Glu Thr Ile Glu Glu Trp Glu Pro
305                 310                 315                 320

Lys Thr Pro Thr Ser Glu Gln Ala Thr Glu Thr Ser Glu Lys Thr Asp
                325                 330                 335

Thr Thr Glu Thr Val Glu Ser Ser Gln Pro Glu Val His Val Ser Pro
            340                 345                 350

Thr Glu Glu Glu Asn Pro Asp Glu Ser Glu Thr Leu Gly Thr Ile Glu
        355                 360                 365

Pro Ile Leu Pro Glu Lys Pro Ser Val Thr Thr Glu Glu Asn Gly Thr
    370                 375                 380

Thr Glu Thr Ala Glu Ser Ser Gln Pro Glu Val His Val Ser Pro Thr
385                 390                 395                 400

Glu Glu Glu Asn Pro Asp Glu Ser Glu Thr Leu Gly Ile Ile Ser Pro
                405                 410                 415

Ile Ile Pro Glu Lys Pro Ser Val Thr Thr Glu Glu Asn Gly Thr Thr
            420                 425                 430

Glu Thr Ala Glu Ser Ser Gln Pro Glu Val His Val Ser Pro Thr Lys
        435                 440                 445

Glu Ile Thr Thr Thr Glu Lys Lys Gln Pro
    450                 455

<210> SEQ ID NO 2
<211> LENGTH: 1374
<212> TYPE: DNA
<213> ORGANISM: Enterococcus faecalis

<400> SEQUENCE: 2
gaattgagca aaagttcaat cgttgacaaa gtagaattag atcacactac tttatatcaa      60
ggggagatga cctccattaa agtatctttt agtgacaaag aaaatcagaa aataaaacct     120
ggcgatacta ttactttaac tttaccagac gaactagttg aatgaccga gaacgatggc     180
```

```
tcaccacgaa aaatcaattt aaatggttta ggggaagttt ttatctataa agatcatgtt    240
gtagcaacat ttaatgaaaa agttgaatct ttacataatg tgaatgggca tttttctttc    300
gggattaaaa cgcttatcac caatagttcg caaccgaatg tgatagaaac ggatttcgga    360
acagcaacgg cgactcaacg tttgacgatt gaaggagtga ccaacacaga gactggccaa    420
attgagcgag actatccgtt tttttataaa gtaggcgatt tggctggaga gtcaaatcaa    480
gtacgttggt ttttaaatgt gaacctcaat aaatccgatg tcacagaaga tatttcaatt    540
gcggatcgac aaggaagtgg tcaacaatta aataaagaga gttttacatt tgatattgtg    600
aatgacaaag aaactaaata tatttcactt gccgagtttg agcaacaagg ttatggcaaa    660
attgacttcg taacagataa tgactttaat ttacgttttt atcgggataa agcacgcttt    720
acttccttta tcgtccgtta cacttcgaca atcacggaag caggccaaca tcaagcaaca    780
tttgaaaata gttatgacat caattatcaa ctaaacaatc aagacgcaac gaatgaaaaa    840
aatacatcac aggttaaaaa tgtttttgta gaaggcgagg caagcggcaa tcaaaatgtg    900
gaaatgccaa cagaagaaag tctagacatt cctttagaga caatagaaga atgggaacca    960 aagcaccta cttcggaaca ggcaacagaa acaagtgaaa agacagacac aacagaaacc    1020
gtagaaagca gccaaccaga agttcatgtt tcaccaacag aagaagaaaa tccagatgaa    1080
agtgaaacac taggcacgat tgagccaatc ctacctgaaa aaccaagtgt gacaactgaa    1140
gagaacggca acagaaac cgcagaaagc agtcaaccag aagttcatgt ctcaccaacg    1200
gaagaagaaa atccagatga agtgaaacg ttaggtataa tttccaccaat tattcctgaa    1260 aaaccaagtg tgacaactga agagaacggc acaacagaaa ccgcagaaag cagtcaacca    1320
gaagtccatg tctcaccaac aaaagaaatt actacaactg agaaaaaaca gcca          1374
```

<210> SEQ ID NO 3
<211> LENGTH: 12
<212> TYPE: PRT
<213> ORGANISM: Enterococcus faecalis

<400> SEQUENCE: 3

Met Arg Gly Ser His His His His His His Gly Ser
1               5                   10

<210> SEQ ID NO 4
<211> LENGTH: 15
<212> TYPE: DNA
<213> ORGANISM: Enterococcus faecalis

<400> SEQUENCE: 4
gaaaatccag atgaa                                                        15

<210> SEQ ID NO 5
<211> LENGTH: 5
<212> TYPE: PRT
<213> ORGANISM: Enterococcus faecalis
<220> FEATURE:
<221> NAME/KEY: UNSURE
<222> LOCATION: (3)..(3)
<223> OTHER INFORMATION: Xaa can be any amino acid

<400> SEQUENCE: 5

Leu Pro Xaa Thr Gly
1               5

<210> SEQ ID NO 6
<211> LENGTH: 30

-continued

```
<212> TYPE: DNA
<213> ORGANISM: Enterococcus faecalis

<400> SEQUENCE: 6
gcaggatccg aattgagcaa aagttcaatc                                           30

<210> SEQ ID NO 7
<211> LENGTH: 33
<212> TYPE: DNA
<213> ORGANISM: Enterococcus faecalis

<400> SEQUENCE: 7
gcagtcgact cagtctgtct tttcacttgt ttc                                       33

<210> SEQ ID NO 8
<211> LENGTH: 30
<212> TYPE: DNA
<213> ORGANISM: Enterococcus faecalis

<400> SEQUENCE: 8
gcaggatccg aattgagcaa aagttcaatc                                           30

<210> SEQ ID NO 9
<211> LENGTH: 35
<212> TYPE: DNA
<213> ORGANISM: Enterococcus faecalis

<400> SEQUENCE: 9
gcagtcgact catggctgtt ttttctcagt tgtag                                     35

<210> SEQ ID NO 10
<211> LENGTH: 15
<212> TYPE: DNA
<213> ORGANISM: Enterococcus faecalis

<400> SEQUENCE: 10
gaaaatccag atgaa                                                           15

<210> SEQ ID NO 11
<211> LENGTH: 22
<212> TYPE: DNA
<213> ORGANISM: Enterococcus faecalis

<400> SEQUENCE: 11
gagcaaaagt tcaatcgttg ac                                                   22

<210> SEQ ID NO 12
<211> LENGTH: 22
<212> TYPE: DNA
<213> ORGANISM: Enterococcus faecalis

<400> SEQUENCE: 12
gtctgtcttt tcacttgttt ct                                                   22

<210> SEQ ID NO 13
<211> LENGTH: 29
<212> TYPE: DNA
<213> ORGANISM: Enterococcus faecalis

<400> SEQUENCE: 13
cagaactcga gttgagcaaa agttcaatc                                            29

<210> SEQ ID NO 14
```

```
<211> LENGTH: 30
<212> TYPE: DNA
<213> ORGANISM: Enterococcus faecalis

<400> SEQUENCE: 14
tggaggtacc ctagtctgtc ttttcacttg                              30

<210> SEQ ID NO 15
<211> LENGTH: 15
<212> TYPE: DNA
<213> ORGANISM: Enterococcus faecalis

<400> SEQUENCE: 15
gaaaatccag atgaa                                              15

<210> SEQ ID NO 16
<211> LENGTH: 22
<212> TYPE: DNA
<213> ORGANISM: Enterococcus faecalis

<400> SEQUENCE: 16
ctattgtcaa cttctgaaaa ag                                      22

<210> SEQ ID NO 17
<211> LENGTH: 22
<212> TYPE: DNA
<213> ORGANISM: Enterococcus faecalis

<400> SEQUENCE: 17
gagcaaaagt tcaatcgttg ac                                      22

<210> SEQ ID NO 18
<211> LENGTH: 20
<212> TYPE: DNA
<213> ORGANISM: Enterococcus faecalis

<400> SEQUENCE: 18
tcaccaatag ttctcaaccg                                         20

<210> SEQ ID NO 19
<211> LENGTH: 20
<212> TYPE: DNA
<213> ORGANISM: Enterococcus faecalis

<400> SEQUENCE: 19
ccaaattgag cgagactatc                                         20

<210> SEQ ID NO 20
<211> LENGTH: 18
<212> TYPE: DNA
<213> ORGANISM: Enterococcus faecalis

<400> SEQUENCE: 20
cacttgccga gtttgagc                                           18

<210> SEQ ID NO 21
<211> LENGTH: 30
<212> TYPE: DNA
<213> ORGANISM: Enterococcus faecalis

<400> SEQUENCE: 21
aaaatgtgga aatgccaaca gaagaaagtc                              30
```

-continued

```
<210> SEQ ID NO 22
<211> LENGTH: 21
<212> TYPE: DNA
<213> ORGANISM: Enterococcus faecalis

<400> SEQUENCE: 22
agtgaaaaga cagacacaac a                                              21

<210> SEQ ID NO 23
<211> LENGTH: 19
<212> TYPE: DNA
<213> ORGANISM: Enterococcus faecalis

<400> SEQUENCE: 23
aaatgaagga agcccacag                                                 19

<210> SEQ ID NO 24
<211> LENGTH: 21
<212> TYPE: DNA
<213> ORGANISM: Enterococcus faecalis

<400> SEQUENCE: 24
gagaactatt ggtgataagc g                                              21

<210> SEQ ID NO 25
<211> LENGTH: 20
<212> TYPE: DNA
<213> ORGANISM: Enterococcus faecalis

<400> SEQUENCE: 25
cattcgttgc gtcttgattg                                                20

<210> SEQ ID NO 26
<211> LENGTH: 22
<212> TYPE: DNA
<213> ORGANISM: Enterococcus faecalis

<400> SEQUENCE: 26
gtctgtcttt tcacttgttt ct                                             22

<210> SEQ ID NO 27
<211> LENGTH: 20
<212> TYPE: DNA
<213> ORGANISM: Enterococcus faecalis

<400> SEQUENCE: 27 ggttttcag gtaggattgg                                                 20

<210> SEQ ID NO 28
<211> LENGTH: 21
<212> TYPE: DNA
<213> ORGANISM: Enterococcus faecalis

<400> SEQUENCE: 28
tggctgtttt ttctcagttg t                                              21

<210> SEQ ID NO 29
<211> LENGTH: 30
<212> TYPE: DNA
<213> ORGANISM: Enterococcus faecalis

<400> SEQUENCE: 29 atttaattt tgaattggtt cactaagcag                                      30
```

```
<210> SEQ ID NO 30
<211> LENGTH: 30
<212> TYPE: DNA
<213> ORGANISM: Enterococcus faecalis

<400> SEQUENCE: 30
cagcaattta tctccagata atagaaaagc                                           30

<210> SEQ ID NO 31
<211> LENGTH: 146
<212> TYPE: PRT
<213> ORGANISM: Enterococcus faecalis

<400> SEQUENCE: 31

Arg Asp Tyr Pro Phe Phe Tyr Lys Val Gly Asp Leu Ala Gly Glu Ser
1               5                   10                  15

Asn Gln Val Arg Trp Phe Leu Asn Val Asn Leu Asn Lys Ser Asp Val
            20                  25                  30

Thr Glu Asp Ile Ser Ile Ala Asp Arg Gln Gly Ser Gly Gln Gln Leu
        35                  40                  45

Asn Lys Glu Ser Phe Thr Phe Asp Ile Val Asn Asp Lys Glu Thr Lys
    50                  55                  60

Tyr Ile Ser Leu Ala Glu Phe Glu Gln Gln Gly Tyr Gly Lys Ile Asp
65                  70                  75                  80

Phe Val Thr Asp Asn Asp Phe Asn Leu Arg Phe Tyr Arg Asp Lys Ala
                85                  90                  95

Arg Phe Thr Ser Phe Ile Val Arg Tyr Thr Ser Thr Ile Thr Glu Ala
            100                 105                 110

Gly Gln His Gln Ala Thr Phe Glu Asn Ser Tyr Asp Ile Asn Tyr Gln
        115                 120                 125

Leu Asn Asn Gln Asp Ala Thr Asn Glu Lys Asn Thr Ser Gln Val Lys
    130                 135                 140

Asn Val
145
```

COLLAGEN-BINDING PROTEINS FROM ENTEROCOCCAL BACTERIA

This application claims benefit of 60/133,334 filed May 10, 1999.

FIELD OF THE INVENTION

The present invention relates in general to collagen-binding proteins from Enterococcal bacteria, and in particular to collagen-binding proteins identified as "Ace" proteins which are adhesins of collagen from enterococcal bacteria such as *Enterococcus faecalis*, and to antibodies of these proteins and nucleic acid sequences coding for those proteins. In addition, the invention relates to the use of these proteins to inhibit the adhesion of enterococcal cells to a collagen substrate. The collagen-binding proteins and antibodies generated thereto in accordance with the invention can thus be utilized to prepare compositions used in methods to treat or prevent infections and other pathogenic conditions caused by enterococcal bacteria.

BACKGROUND OF THE INVENTION

The enterococcal bacteria, including *Enterococcus faecalis*, are commensal Gram-positive bacteria colonizing the intestines of human and other animal hosts. These bacteria have been recognized as a common cause of endocarditis since the early 1900s, and in the past two decades as opportunistic pathogens that can lead to serious nosocomial infections [1]. They are also associated with many clinical infections in humans including septicemia, bacteremia, and various urinary tract infections. *E. faecalis* has many intrinsic and acquired antibiotic resistances that have long been known to complicate therapy of endocarditis, and during recent years resistances to almost all commercially available antibiotics have appeared, making the development of new therapies against the enterococci all the more important.

Without new therapies to treat or prevent enterococcal infections, health care providers may be left without any effective means to treat serious infections caused by the emerging multi-drug resistant enterococci. New and alternative strategies to treat or prevent these infections are thus clearly needed.

Adherence of pathogenic bacteria to the host tissue, mediated by adhesins, is the first event in a multi-step process that may lead to clinically manifested infections. For organisms such as *Staphylococcus aureus* and *E. faecalis*, which are primarily extracellular pathogens, ECM (extracellular matrix—see footnote 1) components are the targets for adherence. MSCRAMMs (microbial surface components recognizing adhesive matrix molecules) represent a subfamily of bacterial adhesins that recognize and bind to ECM components. Several MSCRAMMs have been isolated and characterized from staphylococci and streptococci [2,3], among them the *S. aureus* collagen-binding MSCRAMM, Cna, such as disclosed in U.S. Pat. No. 6,288,214, incorporated herein by reference.

Cna is a mosaic protein with a molecular mass of 135 kDa (FIG. 1c) [4–8]. This protein features an N-terminal signal sequence followed by a 500-residue long A domain of unique amino acids sequence and a B domain that contains a 110-residue long unit repeated tandemly one to four times in Cna isolated from different strains of *S. aureus* [9]. The C-terminal region of Cna contains a cell wall-associated domain, which includes the LPXTG motif that is a putative recognition site for the hypothetical enzyme sortase that covalently links Cna to the cell wall [4]. A hydrophobic transmembrane region is followed by a short cytoplasmic tail rich in positively charged residues. Earlier work showed that the presence of Cna is necessary and sufficient to allow *S. aureus* cells to adhere to collagenous tissues such as cartilage [10], and Cna was shown to be a virulence factor in experimental septic arthritis [11]. Vaccination of mice with a recombinant form of the Cna A domain protected against induced *staph* sepsis [6].

However, present knowledge of the molecular pathogenesis of enterococcal infections is very limited, and there is a distinct need in the field to develop compositions and methods to address the serious problems presented by enterococcal infection. In addition, despite the fact that it has been shown that clinical isolates can adhere to ECM proteins such as collagen, laminin, and fibrinogen [12,13], the MSCRAMMs involved have not been previously identified, and thus there have not been any collagen-binding proteins isolated which can prevent or treat infections caused by enterococcal bacteria.

SUMMARY OF THE INVENTION

Accordingly, it is an object of the present invention to provide an isolated collagen binding protein from enterococcal bacteria which can bind to intercellular matrix proteins such as collagen so as to be useful in developing methods of inhibiting collagen binding and attachment of enterococcal bacteria to cells.

It is further an object of the present invention to provide ligand-binding domains from the collagen binding protein region of enterococcal bacteria which also can bind to intercellular matrix proteins such as collagen and which can also be isolated and utilized so as to be useful in methods of inhibiting collagen binding and attachment of enterococcal bacteria to cells.

It is a further object of the present invention to provide isolated enterococcal surface proteins that are able to inhibit adhesion to the immobilized extracellular matrix of host cells or the surface of implanted biomaterials.

It is a further object of the present invention to provide a vaccine which can be used in generating an immunogenic reaction in a host and which thus can be used in treating or preventing infection by enterococcal bacterial such as *Enterococcus faecalis*.

It is still further an object of the present invention to generate antisera and antibodies to the collagen binding proteins from *enterococcus* bacteria which can also be useful in methods of treatment which can inhibit binding of the enterococcal bacteria to host cells or to implanted biomaterials and thus be employed in order to treat or prevent enterococcal infections.

It is a further object of the present invention to provide improved materials and methods for detecting and differentiating collagen-binding proteins in enterococcal organisms in clinical and laboratory settings.

It is a further object of the invention to provide nucleic acid sequences which code for the collagen binding proteins in enterococcal bacteria which can be useful in producing the collagen-binding proteins of the invention and in developing probes and primers specific for identifying and characterizing these proteins.

These and other objects are provided by virtue of the present invention which comprises an isolated collagen binding protein identified as the Ace protein from enterococcal bacteria such as *Enterococcus faecalis*, which has been determined to bind to collagen, along with their amino acid and nucleic acid sequences, as well as the sequences governing the specific collagen-binding domains of these proteins. The isolated Ace proteins of the present invention, or active portions or fragments thereof, such as the individual collagen-binding A domain described below, can thus be utilized in methods of treating or preventing enterococcal infection through the inhibition of the ability of the bacteria to bind to collagen, or through the development of antibodies thereto which will prevent or inhibit the bacteria's ability to bind to host cells. In addition, the collagen-binding Ace proteins of the present invention may be utilized in much the same manner as the Cna collagen-binding protein from staphylococcal bacteria, as described more fully in U.S. Pat. No. 6,288,214, incorporated herein by reference.

In another aspect of the present invention, there is also provided antisera and antibodies generated against the collagen binding proteins of the present invention which also can be utilized in methods of treatment which involve inhibition of the attachment of the Ace proteins to collagen. In particular, it has been shown that antibodies to Ace in accordance with the present invention can block adherence of *enterococcus* bacteria to extracellular matrix proteins.

Accordingly, in accordance with the invention, antisera and antibodies raised against the Ace proteins, or immunogenic portions thereof, may be employed in vaccines, and other pharmaceutical compositions containing the proteins for therapeutic purposes are also provided herein. In addition, diagnostic kits containing the appropriate proteins, or antibodies or antisera raised against them, are also provided so as to detect bacteria expressing these proteins.

These embodiments and other alternatives and modifications within the spirit and scope of the disclosed invention will become readily apparent to those skilled in the art from reading the present specification and/or the references cited herein.

BRIEF DESCRIPTION OF THE DRAWING FIGURES

FIG. 1a depicts the domain organization of the Ace protein from *E. faecalis*. The recer sequence present in multiple copies within the B domain is denoted by arrows; FIG. 1b depicts a recombinant protein in accordance with the present invention that mimics the Ace A domain, with the inclusive residues indicated; FIG. 1c depicts the domain organization of *S. aureus* FDA 574 Can; FIG. 1d depicts recombinant proteins that mimic portions of the Cna MSCRAMM's A domain, with the inclusive residues indicated. The putative signal peptide (S), collagen-binding domain (A), domain of repeat units (B), cell wall domain (W), membrane-spanning domain (M), and charged C-terminal domain (C) are indicated for both MSCRAMMs. The region of homology between Ace and Cna spans the hash-marked blocks, with the shaded blocks depicting the regions modeled in FIGS. 2a–2c. In these recombinant proteins, MRGSHHHHHHGS (SEQ ID No. 3) is the amino acid sequence of the unstructured N-terminal His$_6$-tag required for purification; and FIG. 1e depicts amino acids 174–319 of the *E. faecalis* Ace protein (obtained from the Microbial Genome Database). Ace residues that are identical to the corresponding residues in Cna 151–318 are in bold; those that are similar are in italics. Residues corresponding to those in Cna 151–318 known to be critical for collagen binding are underlined (the sequence of Cna 151–318 is reported in reference 5).

Figure 2B:
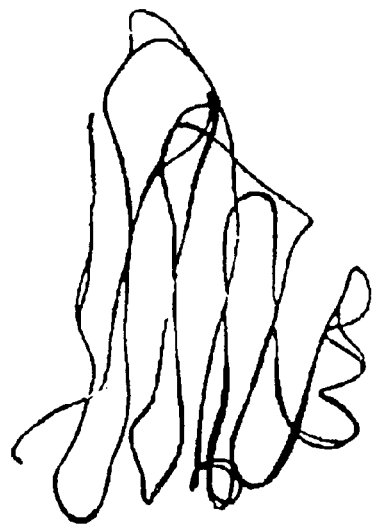
Figure 2C:

FIG. 2a depicts a ribbon diagram of *E. faecalis* Ace residues 174–319 mapped onto Cna 151–318 X-ray structure, with cyan segments denoting regions of sequence identity or similarity and gray denoting regions lacking homology. FIG. 2b depicts ribbon diagrams of *E. faecalis* Ace A domain residues 174–319 (green) overlaid with Cna 151–318 (red); FIG. 2c depicts Space-filled model of *E. faecalis* Ace A domain residues 174–319 mapped onto Cna 151–318 structure. In panel c, residues within the putative collagen-binding trench that are conserved in *S. aureus* Cna 151–318 and *E. faecalis* Ace 174–319 are depicted in blue, trench residues that are not conserved are depicted in green, and the one cyan residue is a T in Cna 151–318 and a V in Ace. These structures harbor the introduced gaps described herein.

Figure 3:
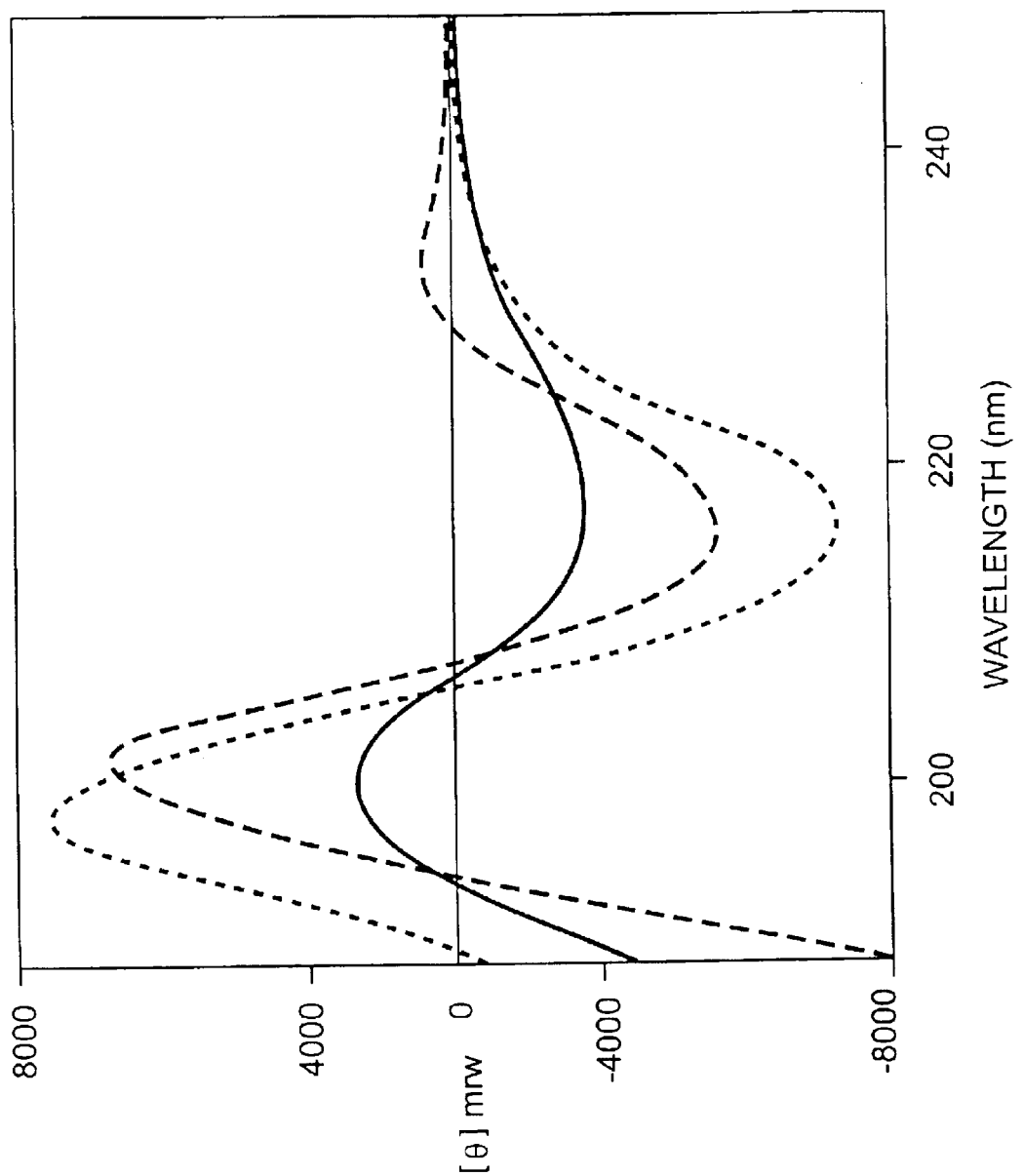

FIG. 3 depicts the far-UV CD spectra of recombinant proteins mimicking the *E. faecalis* EF1 Ace A domain (—) and the *S. aureus* Cna A domain, full-length (- - -) and residues 151–318, ( ). Secondary structure compositions are reported in Table 1. Mean residue weight ellipticity reported in (deg·cm$^2$/dmol).

Figure 4A:
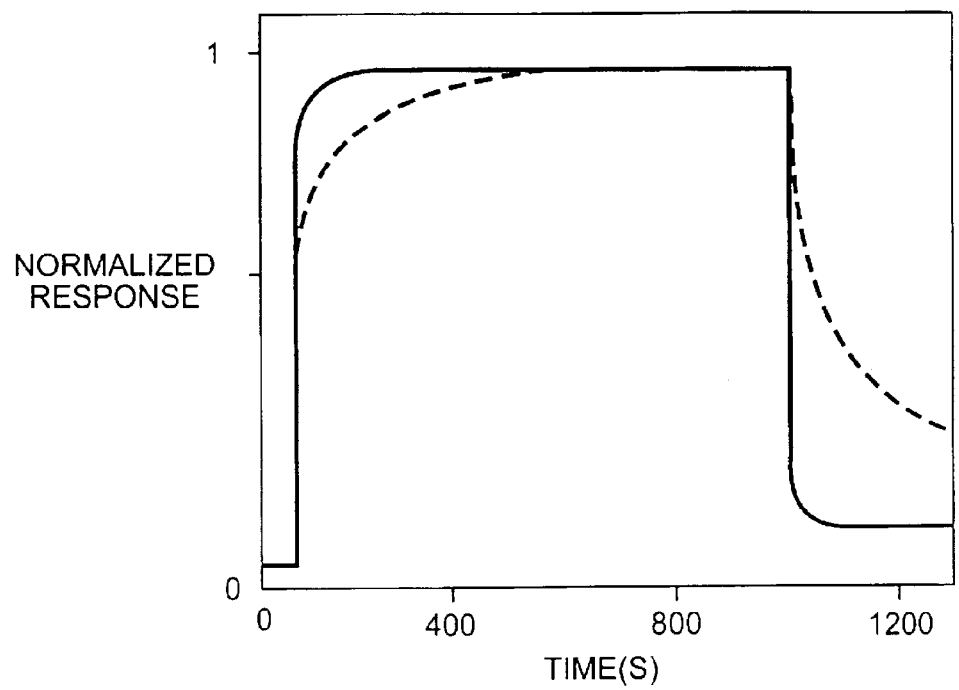
Figure 4B:
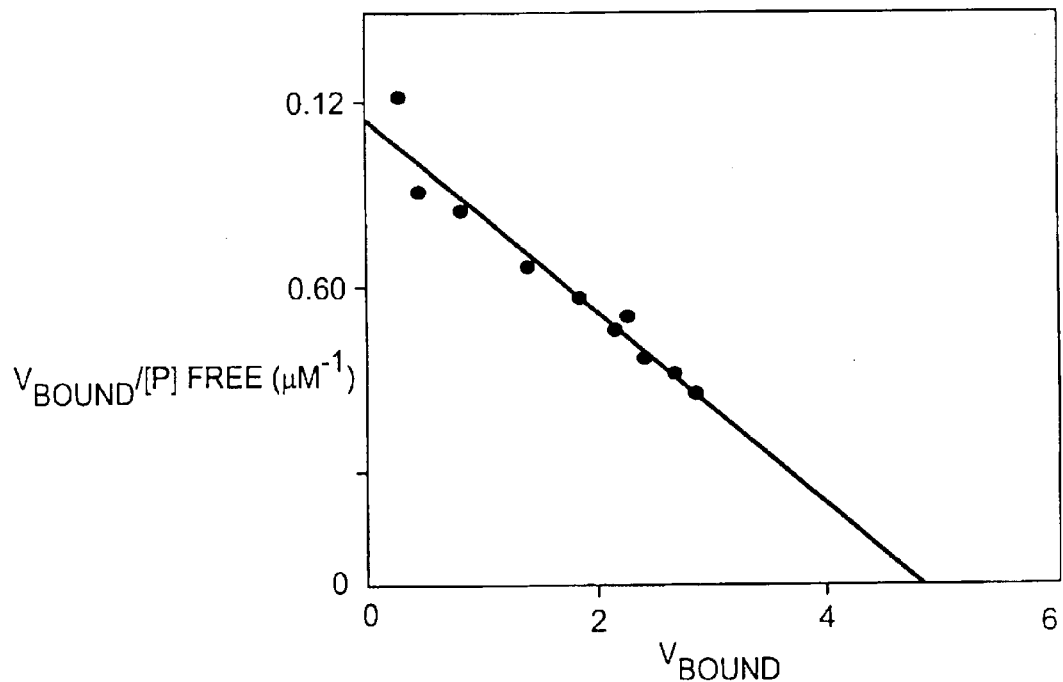

FIG. 4a depicts representative profiles of the relative SPR responses for the binding of 20 $\mu$M recombinant *E. faecalis* EF1 Ace A domain (—) and *S. aureus* Cna A domain residues 151–318 (—) to immobilized Type I collagen. In the analyses shown here, the association occurs from 55 to 960 s and the dissociation begins at 960 s. Both profiles have been corrected for the response of protein over a flow cell containing no collagen; FIG. 4b depicts a Scatchard plot of 1–70 $\mu$M *E. faecalis* EF1 Ace A domain binding to 2436 RU immobilized Type I collagen as measured by SPR. The analysis was repeated with varying MSCRAMM concentrations and amounts of immobilized collagen. No SPR signal was detected for Ace A domain concentrations of less than 1 $\mu$M. From three measurements, $K_D$=48±7 $\mu$M; n=5.3±0.3.

Figure 5:
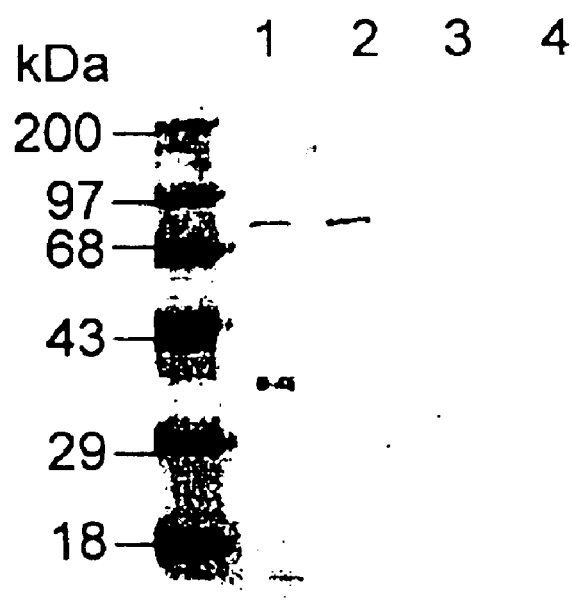

FIG. 5 depicts a Western blot analysis of *E. faecalis* surface extracts. *E. faecalis* strains EF1 (lanes 1 and 3) and EF2 (lanes 2 and 4) surface extracts were prepared by mutanolysin digestion and detected using anti-Ace A domain IgG (lanes 1 and 2) or pre-immune IgG (lanes 3 and 4). Prestained molecular mass standards are shown on the left.

Figure 6A:
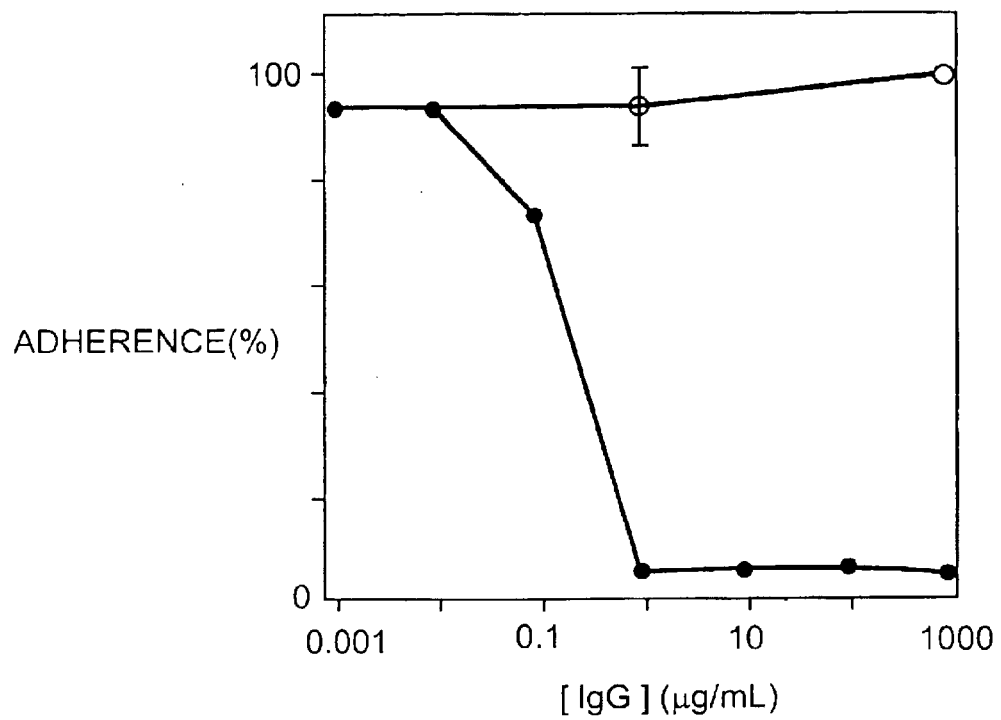
Figure 6B:
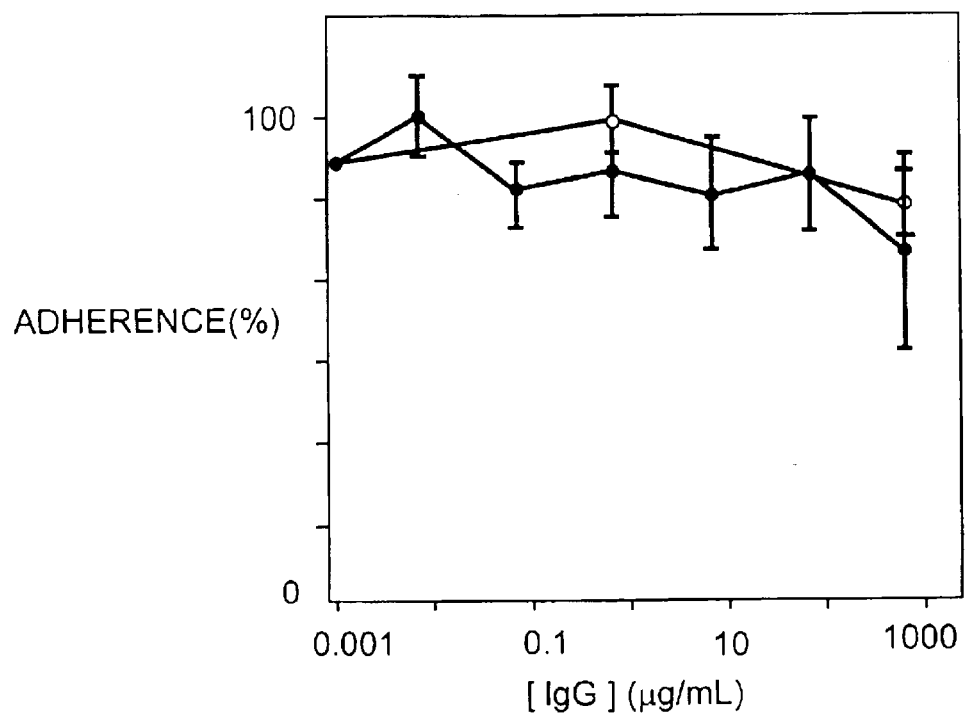

FIG. 6a depicts the inhibition of *E. faecalis* strain OG1RFΔGel and FIG. 6b depicts *S. aureus* strain Phillips binding to Type I collagen by anti-Ace A domain IgG. FITC-labeled bacteria were preincubated with anti-Ace A domain IgG (●) or pre-immune IgG (○) before addition to wells coated with Type I collagen. Values are expressed as the percent adherence obtained in the absence of antibody and represent the mean±.

Figure 7:
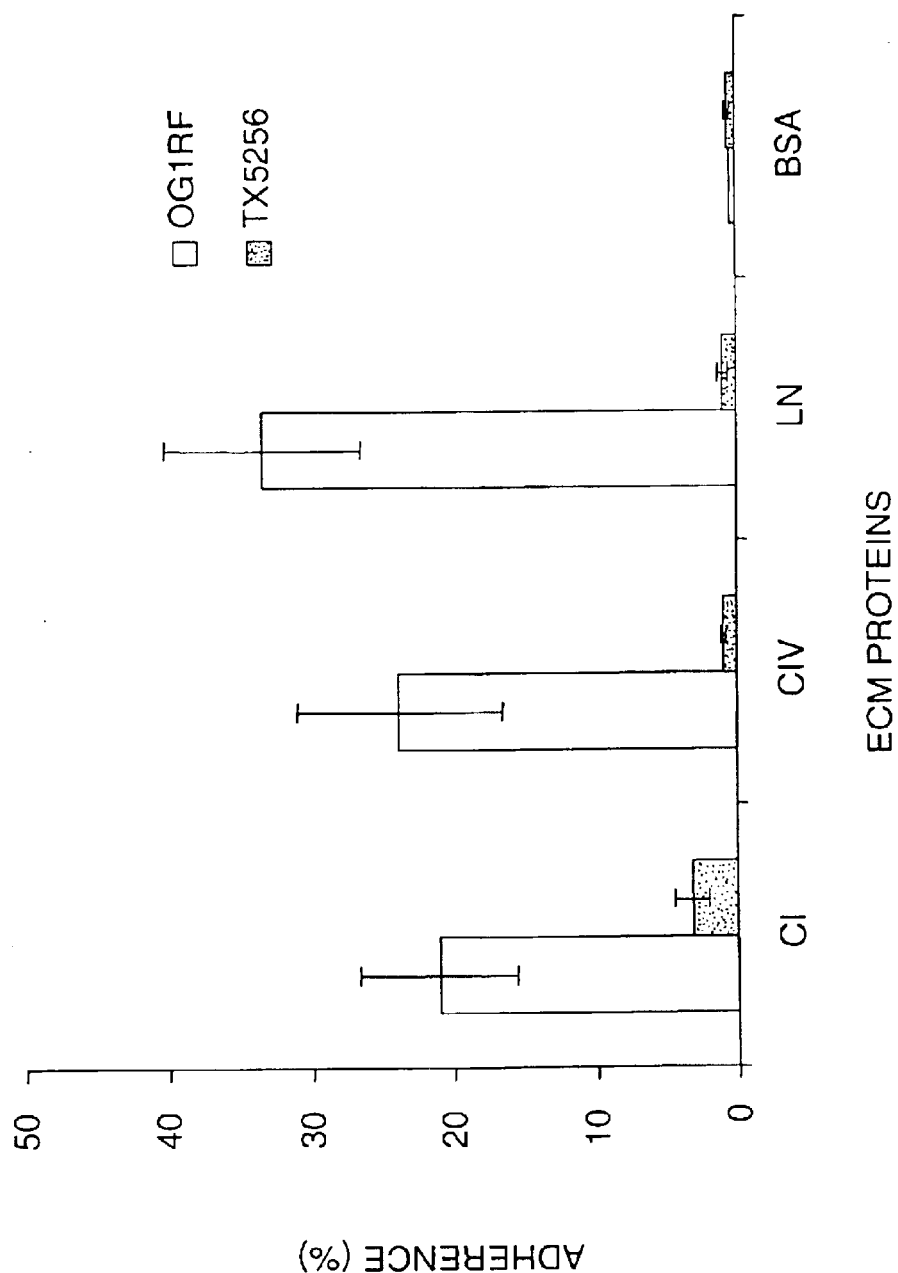

FIG. 7 depicts the adherence of *E. faecalis* OG1 RF and TX5256 (OG1RF ace::pTEX5253) to immobilized collagen type I (CI), collagen type IV (CIV), laminin (LN), and bovine serum albumin (BSA). Adherence was tested in wells coated with 1 $\mu$g of ECM proteins (see text). Bars represent the means of % of cells bound±standard deviation for six wells. Results are representative of three independent experiments. BSA was used as a negative control. (ECM proteins: extracellular matrix proteins).

Figure 8:
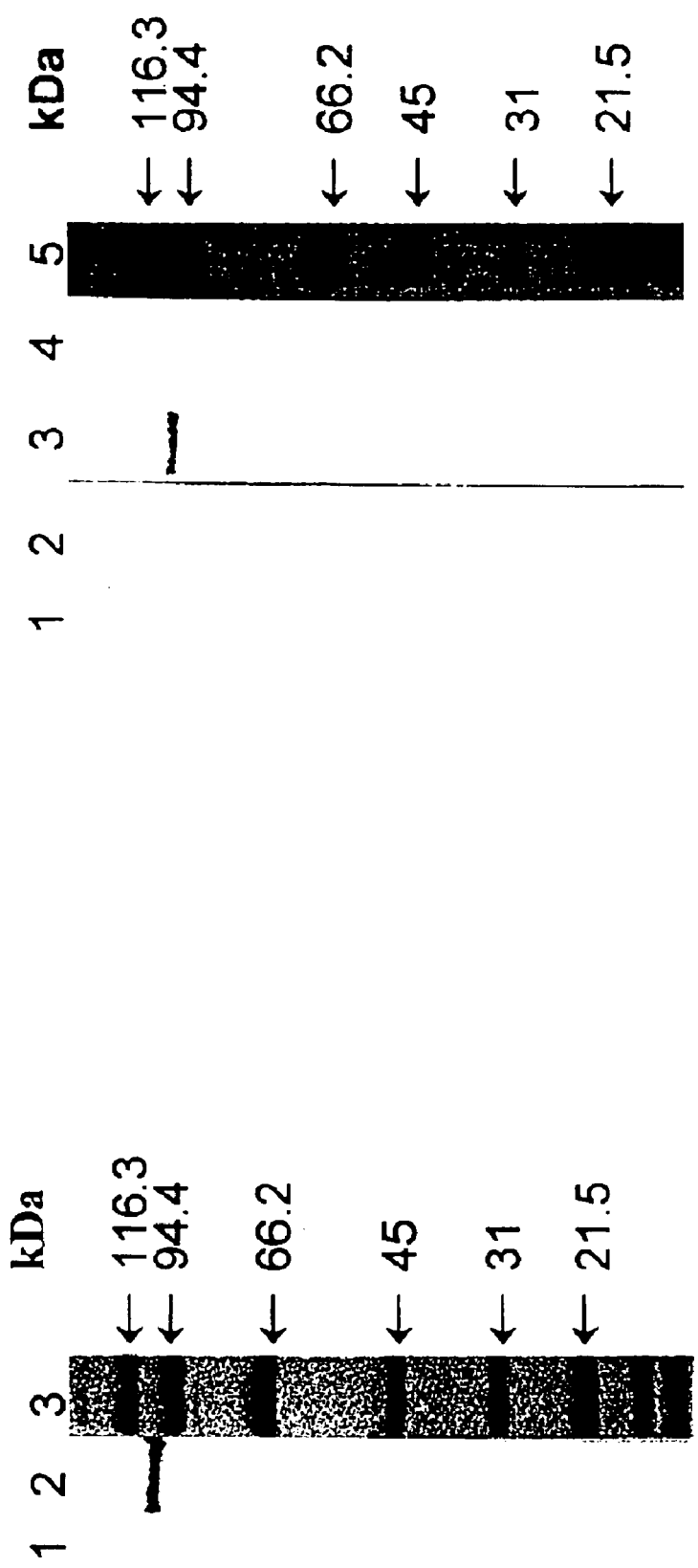

FIGS. 8A and 8B depict Western blots of *E. faecalis* OG1 RF and its ace mutant TX5256 (OG1 RF ace::pTEX5253). A) Mutanolysin surface preparations probed with anti-Ace A polyclonal immune serum. Lanes 1 and 2: protein extracts from 37° C. and 46° C. grown OG1 RF, respectively; and lane 3: molecular weight standards. B) Mutanolysin surface preparations of 46° C. grown *E. faecalis* OG1 RF and TX5256. Lanes 1 and 2: OG1RF and TX5256 protein extracts probed with rabbit preimmune serum; lanes 3 and 4:

OG1RF and TX5256 protein extracts probed with anti-Ace A polyclonal immune serum; and lane 5: molecular weight standards.

Figure 9:
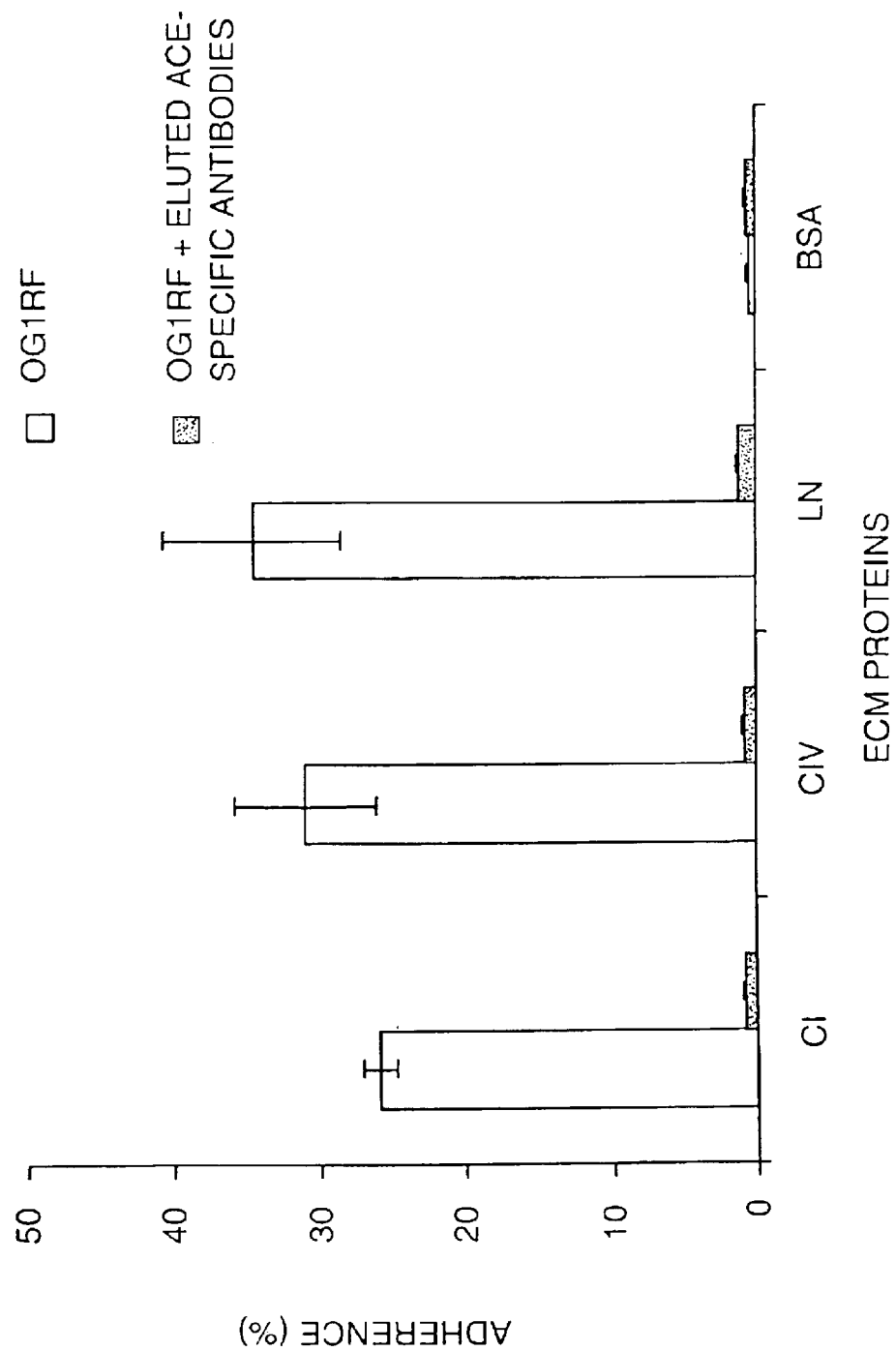

FIG. 9 depicts the inhibition of adherence of E. faecalis OG1 RF to ECM proteins by eluted Ace A specific antibodies. These antibodies were eluted using recombinant Ace A on western blot and were from anti-Ace A polyclonal immune serum. Labeled bacteria were incubated with 1 μg/ml of eluted Ace-specific antibodies for 1 hour at 37° C. Adherence was tested in wells coated with 1 μg of ECM proteins (see text). Bars represent the means of % of cells bound±standard deviation for four wells. (ECM proteins: extracellular matrix proteins; CI: collagen type I; CIV: collagen type IV; LN: laminin; and BSA: bovine serum albumin).

Figure 10:
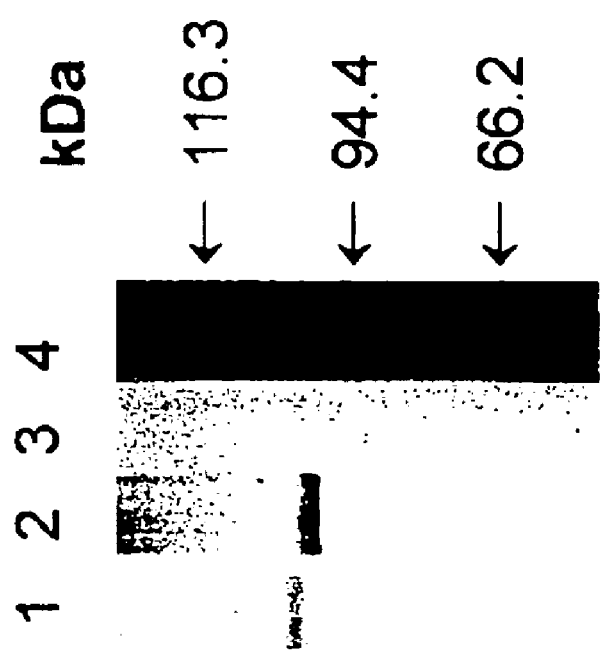

FIG. 10 depicts a Far-western blot assay of extracts of 46° C. grown E. faecalis OG1 RF and its ace mutant TX5256. OG1 RF and TX5256 extracts on PVDF membrane were probed with 10 μg/ml of collagen type IV (CIV) and bound CIV was detected using anti-CIV monoclonal antibodies. Lane 1: collagen type IV (positive control); lanes 2 and 3: OG1 RF and TX5256 mutanolysin extracts; and lane 4: molecular weight standards.

Figure 11:
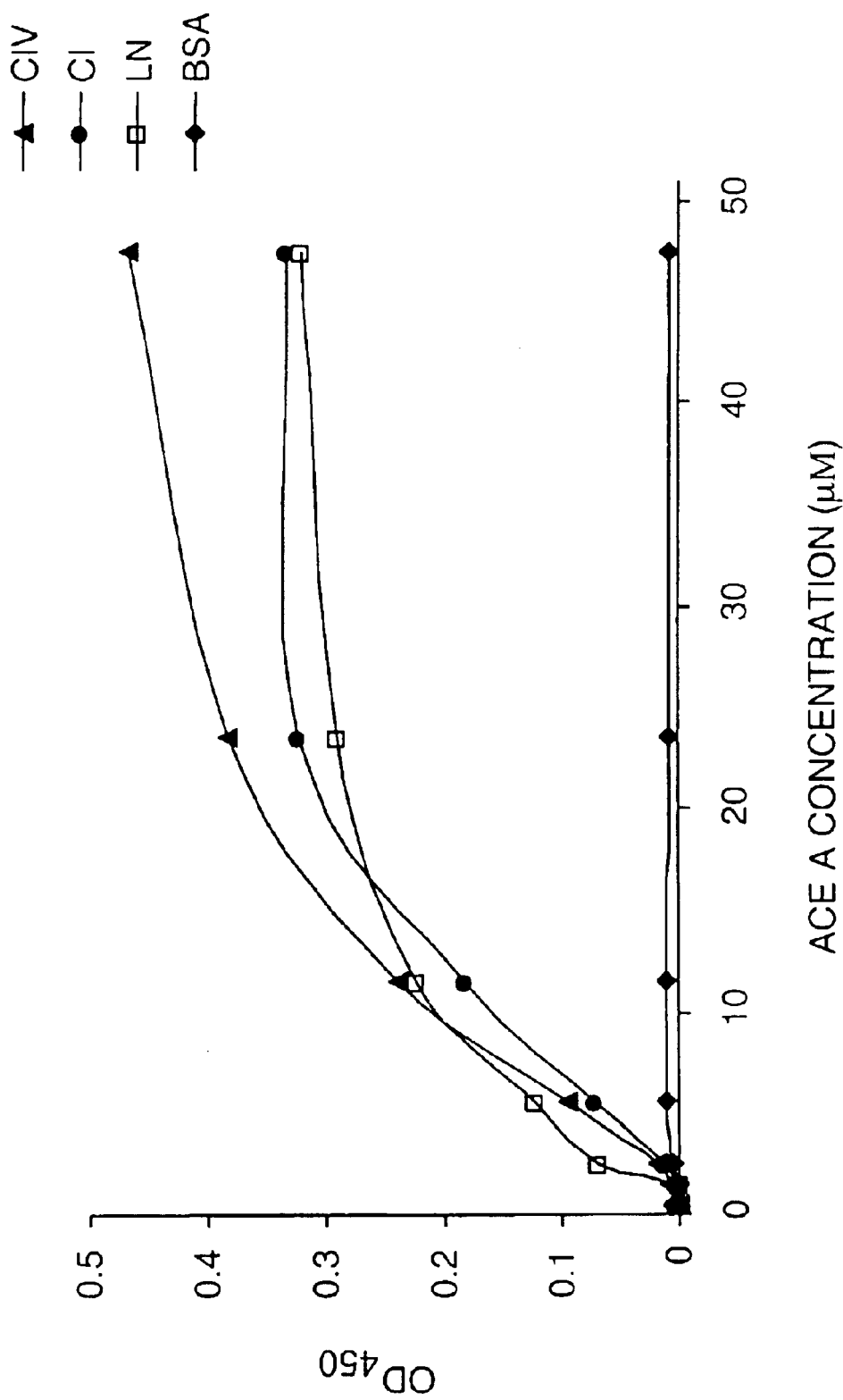

FIG. 11 depicts the binding of recombinant Ace A to immobilized ECM proteins CI, CIV, and LN (10 μg) as a function of concentration of Ace A. BSA was used as a negative control. All $OD_{450}$ values were corrected for the response of penta-His monoclonal antibodies with CI, CIV, and LN, respectively. (ECM proteins: extracellular matrix proteins; CI: collagen type I; CIV: collagen type IV; LN: laminin; and BSA: bovine serum albumin).

FIGS. 12A–D depict the structural organization of Ace and its variation in different E. faecalis strains; A) Schematic representation of E. faecalis OG1RF Ace. S: 31 amino acid putative signal peptide; A domain: 335 amino acid non-repetitive binding domain; B domain (5.4 repeats): 20 amino acid partial repeat followed by five 47 amino acid repeats separated by recer sequences (GAA AAT CcA GAT GAA (SEQ ID No. 4) coding for presumably unstructured ENPDE); W: cell wall domain; M: membrane-spanning domain; and C: charged C-terminal. B) Diagrammatic representation of Ace B domain variants. C) Variations in Ace A identified in 26 E. faecalis strains collected worldwide. Shaded region represents amino acids 174–319 of the E. faecalis Ace protein that corresponds to S. aureus, Cna, 151–318 known to be critical for collagen binding. X→Y denotes respective amino acid change. Number in parentheses denotes number of strains in which amino acid change was observed in the 26 sequenced strains. D) Amino acid sequence of B repeats of OG1 RF. Non-identical amino acids are shaded.

Figure 13:
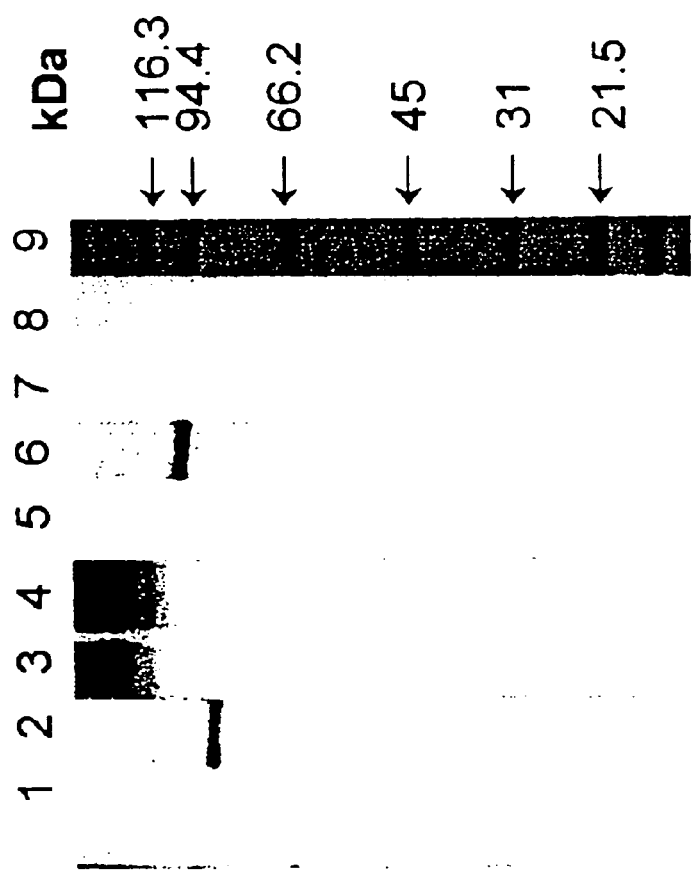

FIG. 13 depicts a Western blot of mutanolysin surface preparations from 37° C. and 46° C. grown E. faecalis isolates probed with anti-Ace A polyclonal immune rabbit serum. Lanes 1 and 2: protein extracts from 37° C. and 46° C. grown MC02152; lanes 3 and 4: protein extracts from 37° C. and 46° C. grown END6; lanes 5 and 6: protein extracts from 37° C. and 46° C. grown V583; lanes 7 and 8: protein extracts from 37° C. and 46° C. grown SE47b; and lane 9: molecular weight standards.

Figure 14:
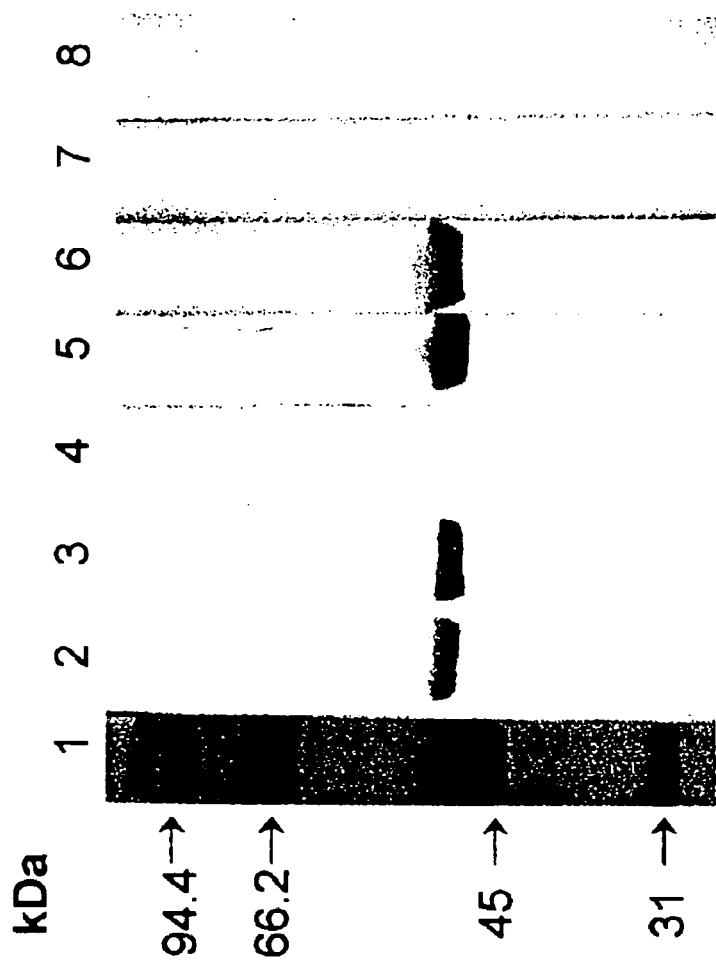

FIG. 14 depicts an immunoblot of recombinant Ace A protein of E. faecalis OG1RF after probing with sera obtained from patients diagnosed with enterococcal infections. Lane 1: molecular weight standards; lanes 2 to 6: sera from different patients with E. faecalis endocarditis; Lane 7: serum from patient with E. faecium endocarditis; and lane 8: normal human serum.

Figure 15:
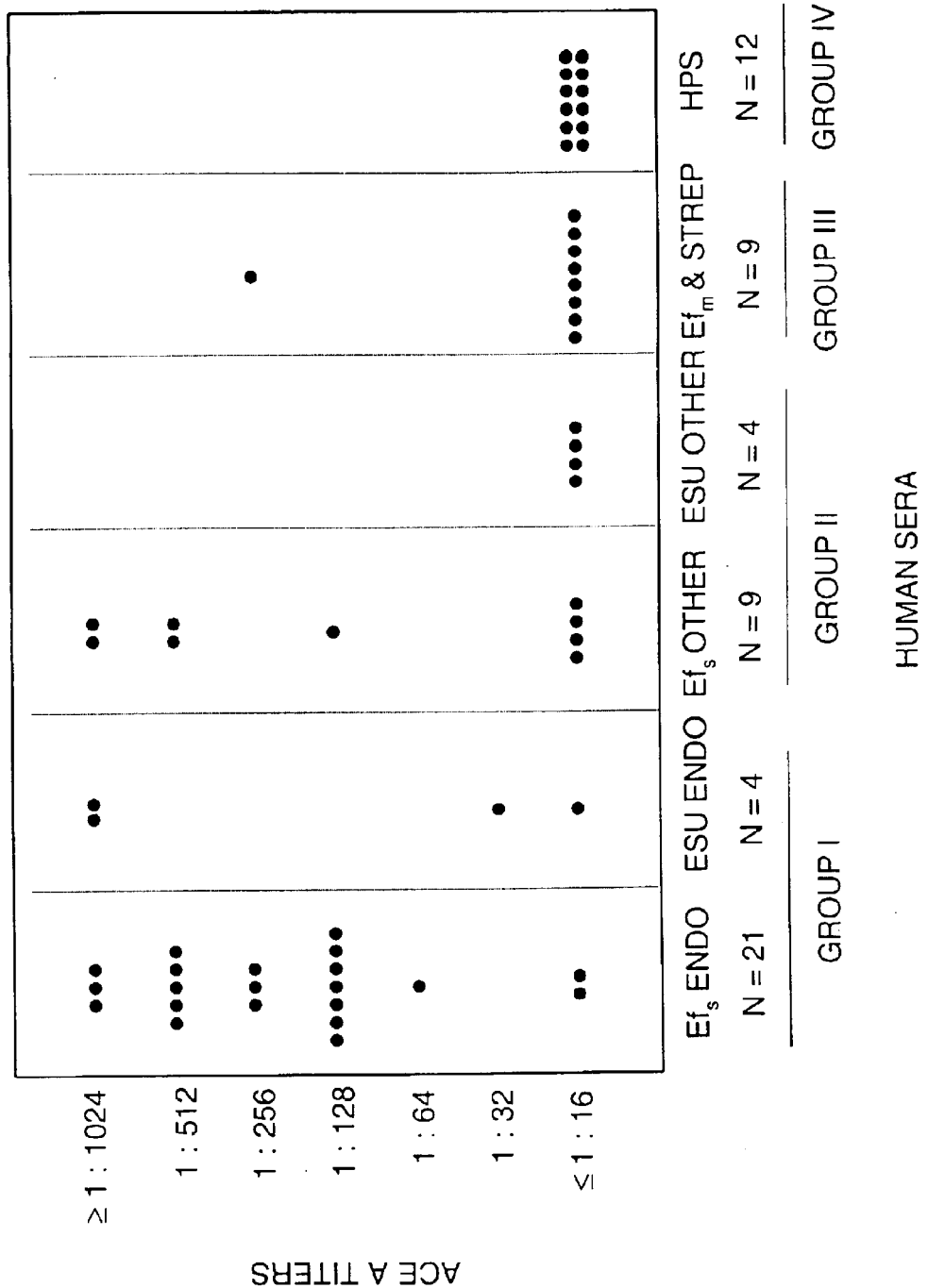

FIG. 15 depicts the distribution of anti-Ace A IgG titers in human sera. $Ef_s$ endo: sera from patients with E. faecalis endocarditis; ESU endo: sera from patients with endocarditis due to Enterococci Species Unknown; $Ef_s$ other: sera from patients with E. faecalis non-endocarditis infections; ESU other sera from patients with ESU non-endocarditis infections; $Ef_m$: sera from 6 patients with E. faecium endocarditis and one patient with E. faecium urosepsis; Strep: patient sera from streptococcal infections; and HPS: hospitalized patient sera with no knowledge of their diagnosis or of any infection. (ESU represents species identified at time of diagnosis and the strains isolated from patients who had donated serum were not available to us and hence were not identified to species in our laboratory).

Figure 16:
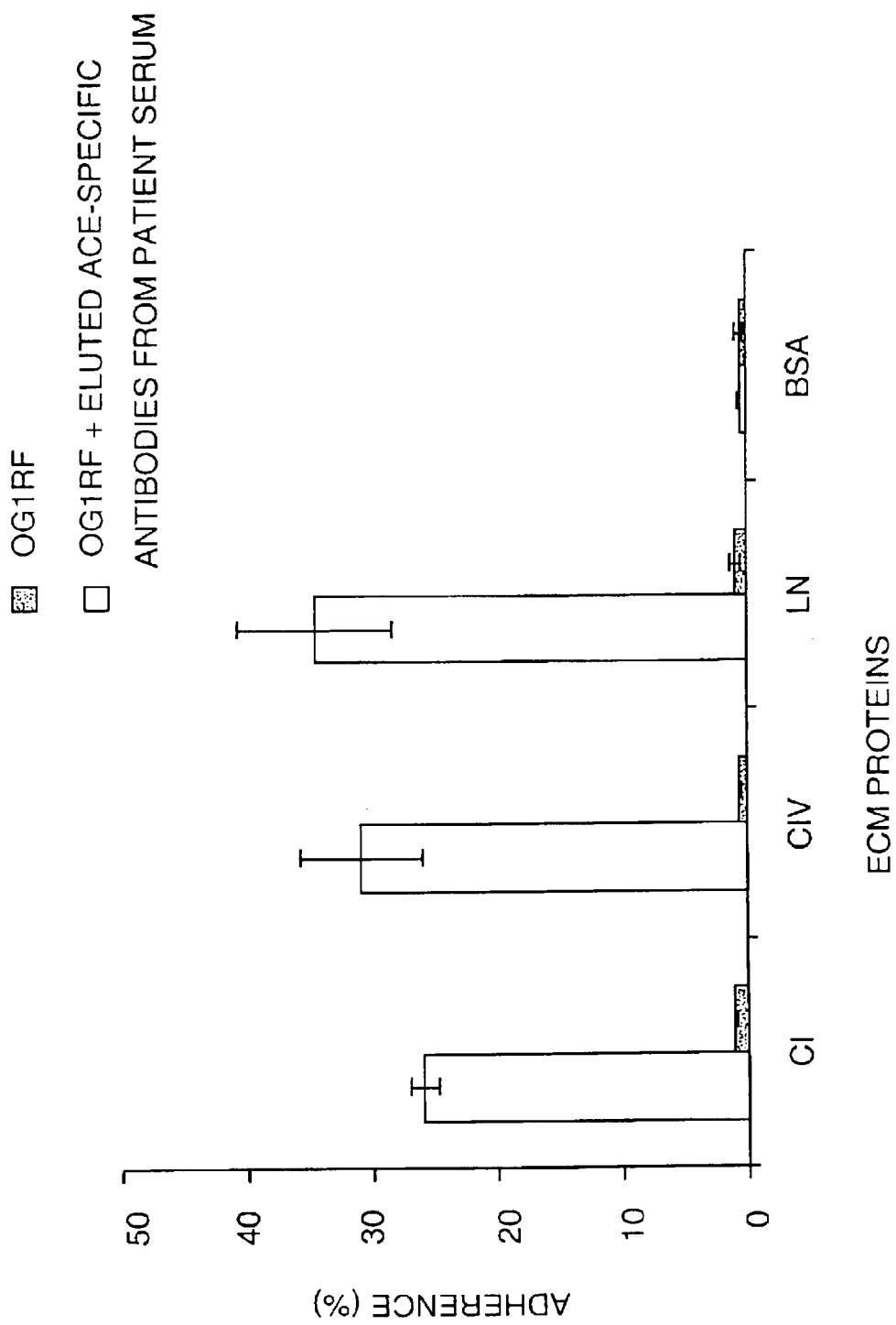

FIG. 16 depicts the inhibition of adherence of E. faecalis OG1 RF to ECM proteins by Ace A specific antibodies eluted from E. faecalis endocarditis patient serum S0032. $^{35}S$ labeled bacteria were incubated with 10 μg/ml of eluted Ace A specific antibodies for 1 hour at 37° C. Adherence was tested in wells coated with 1 μg of ECM proteins (see text). Bars represent the means of % of cells bound±standard deviation for four wells. (ECM proteins: extracellular matrix proteins; CI: collagen type I; CIV: collagen type IV; LN: laminin; and BSA: bovine serum albumin).

DETAILED DESCRIPTION OF THE PREFERRED EMBODIMENTS

In accordance with the present invention, there is provided an isolated collagen binding protein from enterococcal bacteria identified as the Ace protein (or adhesion of collagen from enterococcal bacteria), which is a 74 kDa protein which has a structural similarity to that of MSCRAMMs from other Gram-positive bacteria such as depicted in FIG. 1a. The Ace protein in accordance with the invention is an extracellular matrix-binding protein of enterococcal bacteria such as Enterococcus faecalis, which can bind with collagens such as collagen type I and type IV and with laminin, and includes any portion, fragment or domain, such as the A domain described further below, which possesses collagen-binding activity. The collagen-binding Ace protein from Enterococcus faecalis has the amino acid sequence set forth herein as SEQ ID No. 1, and the nucleic acid sequence encoding the Ace protein is set forth herein as SEQ ID No. 2.

In the collagen-binding Ace protein of the invention, a possible signal sequence involving the first 31 amino acids is followed by a 335-long amino acid domain identified as the A domain. The B domain is composed of 4.5 tandemly repeated 47-residue units of >90% identity. The C-terminus region is composed of a putative cell wall-associated domain rich in proline residues and contains the cell-wall anchoring LPXTG (SEQ ID No. 5) consensus sequence [26]. An 18-amino acid hydrophobic transmembrane segment followed by a short cytoplasmic tall represents the terminal end of the protein.

A central segment of the A domain of the enterococcal Ace protein appears to have a high degree of similarity to residues 151–318 of the Cna protein of S. aureus and shows a similar pattern in structural models, as shown in FIGS. 2a–2c. In addition, when produced recombinantly, an isolated A domain recombinant was shown to have a sheet structure and to bind collagen. Further, antibodies to the A domain were generated, as described further below, and were tested for their ability to inhibit the adherence of enterococcal cells to a substrate of Type I collagen. As shown in FIG. 6a as little as 1 μg/mL of anti-Ace IgG almost completely inhibited bacterial adherence to immobilized collagen, whereas there was no effect of the pre-immune IgG over the range of concentrations examined. Accordingly, Ace was shown to be a collagen adhesin present on the surface of enterococcal bacteria, and antibodies to the A domain of this protein were shown to inhibit enterococcal adherence to immobilized collagen.

Accordingly, the Ace proteins of the present invention may be utilized in many applications for the treatment, identification, or prevention of enterococcal infections. For example, compositions containing isolated Ace proteins, or the fragments or portions containing the collagen-binding domain, may be used as blocking agents to bind to collagen-binding sites in a patient, or in implanted biomaterials or other instruments used in surgical operations, and thus be able to inhibit the binding of enterococcal bacteria to collagen and thereby treat or prevent enterococcal infection. In addition, as described more fully below, the Ace proteins or peptides of the invention, including active portions and domains thereof, may be utilized to generate antibodies which can treat or prevent enterococcal infection, either when generated directly in the patient through the use of Ace vaccines, or through therapeutic compositions containing antibodies to the Ace protein or its active portions or fragments.

In accordance with the present invention, a method of inhibiting the attachment of enterococcal bacteria to collagen is provided which comprises administering an Ace collagen-binding protein, or the collagen-binding domain A, in an amount sufficient to inhibit the attachment of enterococcal bacteria to collagen, and such administration may be utilized to block the sites for enterococcal attachment in a patient, a medical device, or a bioimplant. A method is also provided for treating or preventing enterococcal infection in a patient comprising administering an Ace protein or the collagen-binding domain A, such as in a pharmaceutical composition, in an amount sufficient to treat or prevent an enterococcal infection. As would be recognized by one skilled in this art, the precise treatment regimen will be dependent upon the circumstances surrounding the need for treatment, including, e.g., the nature and condition of the patient, the extent and the seriousness of the afflicted area, and the amenability of the patient to particular forms of treatment. Similarly, where the method involves other objects such as biomedical instruments or implants made from biological materials, an appropriate amount and treatment form will be determined based on the circumstances and the materials involved.

As would be recognized by one skilled in the art, the isolated collagen-binding Ace proteins of the present invention may be obtained through conventional isolation or recombination methods well known in the art. For example, in a conventional recombinant procedure, a cloning-vector, such as a plasmid or phage DNA is cleaved with a restriction enzyme, and the DNA sequence encoding the Ace protein, or its A domain or other active fragments thereof, such as consensus or variable sequence amino acid motifs, is inserted into the cleavage site and ligated. The cloning vector is then inserted into a host to produce the protein or fragment encoded by the Ace protein or its A domain as desired. Suitable hosts include bacterial hosts such as *Escherichia coli, Bacillus subtilis*, yeasts and other cell cultures. Production and purification of the gene product may be achieved and enhanced using known molecular biology techniques.

In accordance with the present invention, pharmaceutical compositions are also provided which contain the Ace proteins, or active portions as described herein, and which may be formulated in combination with a suitable pharmaceutical vehicle, excipient or carrier well know in the art. Examples of some suitable vehicles, carriers and excipients would include saline, dextrose, water, glycerol, ethanol, other therapeutic compounds, and combinations thereof. In addition, pharmaceutical compositions may also be formulated using other aspects of the present invention, including nucleic acid molecules coding for Ace, as well as antibodies, or fragments thereof, and these other formulations would similarly be produced using suitable pharmaceutical vehicles, excipients or carriers such as saline, dextrose, water, glycerol, ethanol, etc. The formulation should be appropriate for the mode of administration. The Ace compositions of the present invention will thus be useful for interfering with, modulating, or inhibiting binding interactions between enterococcal bacteria and collagen on host cells.

In addition to the structures of the Ace protein as described herein, as would be recognized by one of ordinary skill in this art, modification and changes may be made in the structure of the proteins and peptides of the present invention and DNA segments which encode them and still obtain a functional molecule that encodes a protein or peptide with desirable characteristics. The amino acid changes may be achieved by changing the codons of the DNA sequence. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In addition, amino acid substitutions are also possible without affecting the collagen binding ability of the isolated proteins of the invention, provided that the substitutions provide amino acids having sufficiently similar properties to the ones in the original sequences.

Accordingly, acceptable amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. The isolated proteins of the present invention can be prepared in a number of suitable ways known in the art including typical chemical synthesis processes to prepare a sequence of polypeptides.

The synthetic polypeptides of the invention can thus be prepared using the well known techniques of solid phase, liquid phase, or peptide condensation techniques, or any combination thereof, can include natural and unnatural amino acids. Amino acids used for peptide synthesis may be standard Boc ($N^a$-amino protected $N^a$-t-butyloxycarbonyl) amino acid resin with the standard deprotecting, neutralization, coupling and wash protocols of the original solid phase procedure of Merrifield (*J. Am. Chem. Soc.,*

85:2149–2154, 1963), or the base-labile N$^\alpha$-amino protected 9-fluorenylmethoxycarbonyl (Fmoc) amino acids first described by Carpino and Han (*J. Org. Chem.*, 37:3403–3409, 1972). Both Fmoc and Boc N$^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other N$^\alpha$-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept Protein Res.* 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties may be used in accordance with the invention. For example, peptides comprising D-amino acids will be resistant to L-amino acid-specific proteases in vivo. In addition, the present invention envisions preparing peptides that have more well defined structural properties, and the use of peptidomimetics and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown or protease activity. It is also well known that in certain systems, constrained peptides show enhanced functional activity (Hruby, *Life Sciences*, 31:189–199, 1982); (Hruby et al., *Biochem J.*, 268:249–262, 1990).

Also provided herein are sequences of nucleic acid molecules that selectively hybridize with nucleic acid molecules encoding the enterococcal collagen-binding proteins of the invention, or portions thereof, such as consensus or variable sequence amino acid motifs, from *Enterococcus faecalis* described herein or complementary sequences thereof. By "selective" or "selectively" is meant a sequence which does not hybridize with other nucleic acids. This is to promote specific detection of Ace or its active fragments, portions or domains. Therefore, in the design of hybridizing nucleic acids, selectivity will depend upon the other components present in a sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus, has the same meaning as "specifically hybridizing". The selectively hybridizing nucleic acids of the invention can have at least 70%, 80%, 85%, 90%, 95%, 97%, 98%, and 99% complementarity with the segment of the sequence to which they hybridize.

The invention contemplates sequences, probes and primers which selectively hybridize to the Ace-encoding DNA or the complementary, or opposite, strand of DNA as those specifically provided herein. Specific hybridization with nucleic acid can occur with minor modifications or substitutions in the nucleic acid, so long as functional species-specific hybridization capability is maintained. By "probe" is meant nucleic acid sequences that can be used as probes or primers for selective hybridization with complementary nucleic acid sequences for their detection or amplification, which probes can vary in length from about 5 to 100 nucleotides, or preferably from about 10 to 50 nucleotides, or most preferably about 18–24 nucleotides. Therefore, the terms "probe" or "probes" as used herein are defined to include "primers". Isolated nucleic acids are provided herein that selectively hybridize with the species-specific nucleic acids under stringent conditions and should have at least 5 nucleotides complementary to the sequence of interest as described by Sambrook et al., 1989. MOLECULAR CLONING: A LABORATORY MANUAL, 2nd ed. Cold Spring Harbor Laboratory, Cold Spring Harbor, N.Y.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of diagnosing the presence of the *E. faecalis*, the degree of complementarity between the hybridizing nucleic acid (probe or primer) and the sequence to which it hybridizes (e.g., enterococcal DNA from a sample) is at least enough to distinguish hybridization with a nucleic acid from other bacteria.

The nucleic acid sequences encoding the Ace protein, or domain A of the Ace protein, can be inserted into a vector, such as a plasmid, and recombinantly expressed in a living organism to produce recombinant proteins or active fragments thereof which will exhibit collagen-binding activity and which can thus be utilized in accordance with the invention to prevent or treat enterococcal infection, or to prevent enterococcal attachment to implanted biological materials.

The present invention also relates to the Ace amino acid sequences and nucleic acid sequences encoding those sequences in a wide variety of *enterococcus* bacteria, including numerous strains of *E. faecalis* bacteria. One study of *enterococcus* bacteria confirmed the specificity of Ace among 350 enterococci including 161 *E. faecalis* isolates obtained from different geographic regions as well as from various clinical sources and then sequenced from selected strains. A comparison of nucleotide and deduced amino acid sequences of Ace from 9 *E. faecalis* strains identified a highly conserved N-terminal domain, followed by a variable B domain which contains 2 to 5 repeats of 47 amino acids in tandem array, preceded by a 20 amino acid partial repeat. Using 17 other strains collected worldwide, the 5'-region of the gene ace that encodes the A domain was sequenced, and these sequences showed $\geq$97.5% identity. Among the previously reported five amino acids critical for collagen binding by Cna of *S. aureus*, four were found to be identical in Ace from all strains tested. Polyclonal immune rabbit serum prepared against recombinant Ace A derived from OG1RF (as described further below) detected Ace in mutanolysin extracts of 7 out of 9 *E. faecalis* strains after growth at 46° C.

In addition to the use of the Ace proteins above in various procedures, including the detection of the presence of Ace or antibodies thereto, the present invention also contemplates the use of the nucleic acids described herein to detect and identify the presence of collagen-binding Ace proteins as well. The methods are useful for diagnosing enterococcal infections as described above or those infections related to enterococcal attachment to implanted biological materials, such as may occur, for example, in catheter related infections, biomaterial related infections, respiratory tract infections, cardiac, gastrointestinal or central nervous system infections, ocular infections, wound infections, skin infections, and a myriad of other diseases that may be caused or exacerbated by enterococcal bacteria.

In accordance with the invention, a preferred method of detecting the presence of enterococcal Ace proteins involves the steps of obtaining a sample suspected of containing enterococci. The sample may be taken from an individual, for example, from one's blood, saliva, tissues, bone, muscle, cartilage, or skin. The cells can then be lysed, and the DNA extracted, precipitated and amplified. Detection of DNA from enterococci can be achieved by hybridizing the amplified DNA with a probe for Ace that selectively hybridizes with the DNA as described above. Detection of hybridization is indicative of the presence of enterococcal bacteria.

Preferably, detection of nucleic acid (e.g. probes or primers) hybridization can be facilitated by the use of detectable moieties. For example, the probes can be labeled with biotin and used in a streptavidin-coated microtiter plate assay. Other detectable moieties include radioactive labeling, enzyme labeling, and fluorescent labeling, for example.

DNA may be detected directly or may be amplified enzymatically using polymerase chain reaction (PCR) or other amplification techniques prior to analysis. RNA or cDNA can be similarly detected. Increased or decrease expression of Ace can be measured using any of the methods well known in the art for the quantification of nucleic acid molecules, such as, for example, amplification, PCR, RT-PCR, RNase protection, Northern blotting, and other hybridization methods.

Diagnostic assays for the Ace protein or active portions thereof, such as consensus or variable sequence amino acid motifs, or anti-Ace or anti-domain A antibodies may also be used to detect the presence of a enterococcal bacteria *Enterococcus faecalis*. Assay techniques for determining protein or antibody levels in a sample are well known to those skilled in the art and include methods such as radioimmunoasssay, Western blot analysis and ELISA assays.

In another aspect of the present invention, the isolated natural, recombinant or synthetic proteins of the present invention, or antigenic portions thereof (including epitope-bearing fragments), or fusion proteins including the Ace protein or the Ace A domain as described above, can be administered to animals as immunogens or antigens, alone or in combination with an adjuvant, for the production of antibodies reactive with the Ace proteins or active portions thereof. Accordingly, the Ace proteins of the present invention, or active domains thereof, may be useful as vaccines to generate an immune response in a patient, or in methods of generating antibodies in a host organism which can then be introduced into a patient in order to prevent or treat an enterococcal infection. In addition, the Ace proteins can be used to screen antibodies or antisera for hyperimmune patients from whom can be derived specific antibodies having a very high affinity for the proteins.

Antibodies to Ace, or its A domain, can also be used in accordance with the invention for the specific detection of collagen-binding enterococcal proteins, for the prevention of infection from the enterococci, for the treatment of an ongoing infection, or for use as research tools. The term "antibodies" as used herein includes monoclonal, polyclonal, chimeric, single chain, bispecific, simianized, and humanized or primatized antibodies as well as Fab fragments, including the products of an Fab immunoglobulin expression library. Generation of any of these types of antibodies or antibody fragments is well known to those skilled in the art. In the present case, isolated antibodies against Ace or its A domain, or antiserum containing such antibodies, has been generated which reacts with Ace in Western immunoblots and ELISA assays and has been shown to interfere with Ace binding to collagen. The isolated antibodies or antiserum can thus be used in methods of preventing or treating enterococcal infection, or for specific agglutination assays to detect bacteria which express Ace on their surface.

To determine if there was any evidence to indicate that Ace might be produced under physiological conditions, a quantitative assay was performed on sera collected from patients with enterococcal infections for the presence of anti-Ace A antibodies. In this study, ninety percent of sera (19 of 21) from patients with *E. faecalis* endocarditis a showed reactivity with titers from 1:32 to >1:1024; the only two sera which lacked the antibodies to Ace A had considerably lower titers of antibodies to other *E. faecalis* antigens as well. Human derived, anti-Ace A purified from an *E. faecalis* endocarditis patient serum inhibited adherence of 46° C. grown *E. faecalis* OG1RF to collagen type I, type IV, and laminin. The experimental results thus confirmed that Ace and the ace gene coding for it are highly conserved among isolates of *E. faecalis* with at least 4 variants appeared to be related to the B domain, and this protein is expressed by different strains during infection in man. Further, in accordance with the present invention, it has been shown that human-derived antibodies to Ace or the Ace A collagen-binding domain can block adherence to these extracellular matrix proteins.

Additionally, an OG1RFace disruption mutant was prepared which showed marked reduction in adherence (to <1 to 3%) to collagen types I and IV, and laminin, when compared to OG1 RF after growth at 46° C. Further, IgGs purified from the anti-Ace A immune serum in accordance with the invention inhibited adherence of 46° C. grown *E. faecalis* OG1RF to immobilized collagen type IV and laminin as well as collagen type I, at a concentration as low as 1 $\mu$g/ml, and also inhibited the 46° C. evoked adherence of two clinical isolates tested. Binding of recombinant Ace A to immobilized collagen types I and IV and laminin was demonstrated in an ELISA and was shown to be concentration dependent. These types of results have confirmed that Ace A mediates the conditional binding of *E. faecalis* OG1 RF to collagen type IV and laminin in addition to collagen type I.

In addition to their use in treatment or prevention of enterococcal diseases and infections, any of the above described antibodies may be labeled directly with a detectable label for identification and quantification of enterococci. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies to the collagen-binding Ace proteins of the present invention, or active portions or fragments thereof, such as the A domain, may also be used in production facilities or laboratories to isolate additional quantities of the proteins, such as by affinity chromatography. For example, antibodies to the collagen-binding protein Ace or its A domain may also be used to isolate additional amounts of collagen.

The isolated Ace proteins of the present invention, or active fragments thereof, and antibodies to the proteins, may thus be utilized in many applications involving the treatment, prevention and diagnosis of enterococcal bacterial infections as described above, or for the development of anti-enterococcal vaccines for active or passive immunization. Further, when administered as pharmaceutical composition to a patient or used to coat medical devices or polymeric biomaterials in vitro and in vivo, both the proteins and the antibodies are useful as blocking agents to prevent or inhibit the binding of enterococci to collagen at the wound site or the biomaterials themselves. Preferably, the antibody is modified so that it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., *Nature* 321:522–525 (1986) or Tempest et al. *Biotechnology* 9:266–273 (1991).

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the protein, antibody, or active fragment to a surface of the device, preferably an outer surface that would be exposed to enterococcal bacterial infection. The surface of the device need not be entirely covered by the protein, antibody or active fragment.

In addition, the present invention may be utilized as immunological compositions, including vaccines, and other pharmaceutical compositions containing the Ace protein or its active regions, are included within the scope of the present invention. Either the Ace protein, or its ligand-binding A domain, or other active or antigenic fragments thereof, or fusion proteins thereof, can be formulated and packaged, alone or in combination with other antigens, using methods and materials known to those skilled in the art for vaccines. The immunological response may be used therapeutically or prophylactically and may provide antibody immunity or cellular immunity, such as that produced by T lymphocytes.

The immunological compositions, such as vaccines, and other pharmaceutical compositions can be used alone or in combination with other blocking agents to protect against human and animal infections caused by or exacerbated by enterococcal bacteria. In particular, the compositions can be used to protect humans against a variety of skin and internal infections normally associated with enterococci, including those serious infections that individuals with compromised immune systems are particularly susceptible towards [1]. The compositions may also be useful as appropriate in protecting both humans and other species of animals where needed to combat similar infections caused by a variety of enterococcal bacteria.

To enhance immunogenicity, the proteins may be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 Daltons, preferably greater than 10,000 Daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

The isolated Ace proteins or its active portions or fragments, such as the A domain, may be administered with an adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. *J.*

Immunol. 147:410–415 (1991) and incorporated by reference herein, encapsulation of the conjugate within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N. H.) may also be useful.

The term "vaccine" as used herein includes DNA vaccines in which the nucleic acid molecule encoding for a collagen-binding Ace protein is used in a pharmaceutical composition is administered to a patient. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), coprecipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992 and Eisenbraun et al., *DNA Cell Biol.* 12:791, 1993), and in vivo infection using cloned retroviral vectors (Seeger et al., *Proc. Natl. Acad. Sci.* 81:5849, 1984).

In another embodiment, the invention is a polynucleotide which comprises contiguous nucleic acid sequences capable of being expressed to produce an Ace gene product upon introduction of said polynucleotide into eukaryotic tissues in vivo. The encoded gene product preferably either acts as an immunostimulant or as an antigen capable of generating an immune response. Thus, the nucleic acid sequences in this embodiment encode an immunogenic epitope, and optionally a cytokine or a T-cell costimulatory element, such as a member of the B7 family of proteins.

There are several advantages of immunization with a gene rather than its gene product. The first is the relative simplicity with which native or nearly native antigen can be presented to the immune system. Mammalian proteins expressed recombinantly in bacteria, yeast, or even mammalian cells often require extensive treatment to ensure appropriate antigenicity. A second advantage of DNA immunization is the potential for the immunogen to enter the MHC class I pathway and evoke a cytotoxic T cell response. Immunization of mice with DNA encoding the influenza A nucleoprotein (NP) elicited a $CD8^+$ response to NP that protected mice against challenge with heterologous strains of flu. (See Montgomery, D. L. et al., *Cell Mol Biol*, 43(3):28592, 1997 and Ulmer, J. et al., *Vaccine*, 15(8): 792–794, 1997.)

Cell-mediated immunity is important in controlling infection. Since DNA immunization can evoke both humoral and cell-mediated immune responses, its greatest advantage may be that it provides a relatively simple method to survey a large number of *E. faecalis* genes for their vaccine potential.

The amount of expressible DNA or transcribed RNA to be introduced into a vaccine recipient will have a very broad dosage range and may depend on the strength of the transcriptional and translational promoters used. In addition, the magnitude of the immune response may depend on the level of protein expression and on the immunogenicity of the expressed gene product. In general, effective dose ranges of roughly about 1 ng to 5 mg, 100 ng to 2.5 mg, 1 $\mu$g to 750 $\mu$g, and preferably about 10 $\mu$g to 300 $\mu$g, of DNA may be suitable, e.g., if administered directly into muscle tissue. Subcutaneous injection, intradermal introduction, impression through the skin, and other modes of administration such as intraperitoneal, intravenous, or inhalation delivery may also be suitable as would be recognized by one skilled in this art. It is also contemplated that booster vaccinations may be provided. Following vaccination with a polynucleotide immunogen, boosting with protein immunogens such as the isolated Ace protein or the isolated A domain is also contemplated.

The polynucleotide may be "naked", that is, unassociated with any proteins, adjuvants or other agents which affect the recipient's immune system. In this case, it is desirable for the polynucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used. These agents are generally referred to herein as transfection facilitating reagents and pharmaceutically acceptable carriers. Techniques for coating microprojectiles coated with polynucleotide are known in the art and are also useful in connection with this invention. For DNA intended for human use it may be useful to have the final DNA product in a pharmaceutically acceptable carrier or buffer solution. Pharmaceutically acceptable carriers or buffer solutions are known in the art and include those described in a variety of texts such as Remington's Pharmaceutical Sciences.

It is recognized by those skilled in the art that an optimal dosing schedule for a vaccination regimen as set forth above will vary according to the needs of the particular patient, but may include as many as one to six or more administrations of the immunizing entity given at intervals of as few as two to four weeks, to as long as five to ten years, or occasionally at even longer intervals, as needed.

Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

In a preferred embodiment, a vaccine is packaged in a single dosage for immunization by parenteral (i.e., intramuscular, intradermal or subcutaneous) administration or nasopharyngeal (i.e., intranasal) administration. If intramuscularly introduced, the vaccine is preferably injected directly intramuscularly into the deltoid muscle. The vaccine is preferably combined with a pharmaceutically acceptable carrier to facilitate administration. The carrier is usually water or a buffered saline, with or without a preservative. The vaccine may be lyophilized for resuspension at the time of administration or in solution.

Microencapsulation of the protein will give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters, polyamides, poly (D,L-lactide-co-glycolide) (PLGA) and other biodegradable polymers. The use of PLGA for the controlled release of antigen is reviewed by Eldridge et al., CURRENT TOPICS IN MICROBIOLOGY AND IMMUNOLOGY, 146:59–66 (1989).

The preferred dose for human administration will be determined based on the needs of the individual patient and the nature of the disorder being treated, for example ranging 0.01 mg/kg to 10 mg/kg. Based on this range, equivalent dosages for heavier body weights can be determined. The dose should be adjusted to suit the individual to whom the composition is administered and will vary with age, weight and metabolism of the individual. The vaccine may additionally contain stabilizers or pharmaceutically acceptable preservatives, such as thimerosal (ethyl(2-mercaptobenzoate-S)mercury sodium salt) (Sigma Chemical Company, St. Louis, Mo.).

When labeled with a detectable biomolecule or chemical, the collagen-binding proteins described herein are useful for purposes such as in vivo and in vitro diagnosis of enterococcal infections or detection of enterococcal bacteria. Laboratory research may also be facilitated through use of such protein-label conjugates. Various types of labels and methods of conjugating the labels to the proteins are well known to those skilled in the art. Several specific labels are set forth below. The labels are particularly useful when conjugated to a protein such as an antibody or receptor. For example, the protein can be conjugated to a radiolabel such as, but not restricted to, $^{32}P$, $^{3}H$, $^{14}C$, $^{35}S$, $^{125}I$ or $^{131}I$. Detection of a label can be by methods such as scintillation counting, gamma ray spectrometry or autoradiography.

Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allophycocyanin, phycocyanin, rhodamine, and Texas Red. The fluorogens are generally detected by a fluorescence detector.

The protein can alternatively be labeled with a chromogen to provide an enzyme or affinity label. For example, the protein can be biotinylated so that it can be utilized in a biotin-avidin reaction, which may also be coupled to a label such as an enzyme or fluorogen. For example, the protein can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, proteins may be labeled with colloidal gold for use in immunoelectron microscopy in accordance with methods well known to those skilled in the art.

The location of a ligand in cells can be determined by labeling an antibody as described above and detecting the label in accordance with methods well known to those skilled in the art, such as immunofluorescence microscopy using procedures such as those described by Warren and Nelson (Mol. Cell. Biol., 7: 1326–1337, 1987).

In addition to the therapeutic compositions and methods described above, the Ace proteins or active portions or fragments thereof, nucleic acid molecules or antibodies may also be useful for interfering with the initial physical interaction between a pathogen and mammalian host responsible for infection, such as the adhesion of bacteria, to mammalian extracellular matrix proteins such as collagen on in-dwelling devices or to extracellular matrix proteins in wounds; to block Ace protein-mediated mammalian cell invasion; to block bacterial adhesion between collagen and bacterial Ace proteins or portions thereof that mediate tissue damage; and, to block the normal progression of pathogenesis in infections initiated other than by the implantation of in dwelling devices or surgical techniques.

The Ace proteins, or active fragments thereof, are useful in a method for screening compounds to identify compounds that inhibit collagen binding of enterococci to host molecules. In accordance with the method, the compound of interest is combined with one or more of the Ace proteins or fragments thereof and the degree of binding of the protein to collagen or other extracellular matrix proteins is measured or observed. If the presence of the compound results in the inhibition of protein-collagen binding, for example, then the compound may be useful for inhibiting enterococci in vivo or in vitro. The method could similarly be used to identify compounds that promote interactions of enterococci with host molecules. The method is particularly useful for identifying compounds having bacteriostatic or bacteriocidal properties.

For example, to screen for enterococcal agonists or antagonists, a synthetic reaction mixture, a cellular compartment (such as a membrane, cell envelope or cell wall) containing one or more of the Ace proteins or fragments thereof and a labeled substrate or ligand of the protein is incubated in the absence or the presence of a compound under investigation. The ability of the compound to agonize or antagonize the protein is shown by a decrease in the binding of the labeled ligand or decreased production of substrate product. Compounds that bind well and increase the rate of product formation from substrate are agonists. Detection of the rate or level of production of product from substrate may be enhanced by use of a reporter system, such as a calorimetric labeled substrate converted to product, a reporter gene that is responsive to changes in Ace nucleic acid or protein activity, and binding assays known to those skilled in the art. Competitive inhibition assays can also be used.

Potential antagonists include small organic molecules, peptides, polypeptides and antibodies that bind to nucleic acid molecules coding for Ace proteins or portions thereof and thereby inhibit their activity or bind to a binding molecule (such as collagen to prevent the binding of the Ace nucleic acid molecules or proteins to its ligand. For example, a compound that inhibits Ace activity may be a small molecule that binds to and occupies the binding site of the Ace protein, thereby preventing binding to cellular binding molecules, to prevent normal biological activity. Examples of small molecules include, but are not limited to, small organic molecule, peptides or peptide-like molecules. Other potential antagonists include antisense molecules. Preferred antagonists include compounds related to and variants or derivatives of the Ace proteins or portions thereof. The nucleic acid molecules described herein may also be used to screen compounds for antibacterial activity.

The invention further contemplates a kit containing one or more Ace-specific nucleic acid probes, which can be used for the detection of collagen-binding proteins from enterococci in a sample, or for the diagnosis of enterococcal infections. Such a kit can also contain the appropriate reagents for hybridizing the probe to the sample and detecting bound probe. In an alternative embodiment, the kit contains antibodies specific to either or both the Ace protein and/or the A domain which can be used for the detection of enterococci.

In yet another embodiment, the kit contains either or both the Ace protein and/or the Ace A domain which can be used for the detection of enterococcal bacteria or for the presence of antibodies to collagen-binding Ace proteins in a sample. The kits described herein may additionally contain equipment for safely obtaining the sample, a vessel for containing the reagents, a timing means, a buffer for diluting the sample, and a calorimeter, reflectometer, or standard against which a color change may be measured.

In a preferred embodiment, the reagents, including the protein or antibody, are lyophilized, most preferably in a single vessel. Addition of aqueous sample to the vessel results in solubilization of the lyophilized reagents, causing them to react. Most preferably, the reagents are sequentially lyophilized in a single container, in accordance with methods well known to those skilled in the art that minimize reaction by the reagents prior to addition of the sample.

The present invention thus provides for the first time an isolated collagen-binding protein from enterococcus bacteria which can be useful in treating or preventing enterococcus infections without the use of antibiotics.

The following example is provided which exemplify aspects of the preferred embodiments of the present invention and investigations regarding the properties of the proteins of the present invention. It should be appreciated by those of skill in the art that the techniques disclosed in these studies which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Experimental Procedures to Isolate and Test the Ace Protein

Identification of *E. faecalis* Ace in a microbial genome database. The amino acid sequence comprising the minimal collagen-binding region (residues 151–318) of the *S. aureus* collagen adhesin, Cna, [4,5] was used to search for homologous sequences in the Microbial Genome Database at the National Center for Biotechnology Information. The BLAST [14] search resulted in the discovery of a novel putative gene sequence from *E. faecalis* of significant homology. The complete open reading frame comprising this sequence was subsequently obtained from The Institute for Genomic Research (TIGR) web site.

Structural modeling studies. The 335 amino acid sequence of Ace A domain was sent to the ExPASy SWISS-MODEL Automated Protein Modeling Server and modeled using the Cna 151–318 molecule structure (11AMX.pdb, Genbank accession number M81736) as a template. A sequence alignment and model of the Ace A domain was returned by the ExPASy server composed of 145 amino acid residues based on the structure of Cna 151–318. Even when the 335 amino acid sequence of Ace A domain was sent to the SWISS-MODEL server without specific instructions to model the sequence on the Cna 151–318 structure, the Cna 151–318 structure file was chosen as a template automatically as determined by a BLAST P(N) search of known protein structure sequences in the ExPDB modified PDB database. Manipulation of the Ace A domain model and Cna 151–318 (IAMX.pdb) was accomplished using the Swiss-PDB Viewer 3.0 software package available at the ExPASy web site and images were rastered using the software package Persistence of View Ray-tracer (POV-Ray 3.0) [15–17]. Temperature factors for the Ace model were higher in the loop regions, especially in regions where there are gaps in the sequence alignment. The RMS deviation calculated between the two structures was 0.63 Å for the Cα atoms (142 total) and 0.61 Å for the analysis of all backbone atoms (426 total). These values for the RMS deviation of the backbone atoms suggested a high level of accuracy for the model.

Bacterial strains and culture conditions. Unless otherwise noted, chemicals and reagents were molecular-biology grade from Sigma (St. Louis, Mo.) or U.S. Biochemical Corp (Cleveland, Ohio). Based on our previous report [12], the *E. faecalis* strains were grown in BHI medium (Difco, Detroit, Mich.) overnight at 46° C. The two *E. faecalis* strains used for the Western blot analysis are designated EF1 (originally described by Caparon and Scott [18]) and EF2 (a clinical *E. faecalis* isolate obtained from University of Alabama-Birmingham, Birmingham, Ala., USA), respectively. Strain OG1RFΔGel is a gelatinase mutant of strain OG1RF [12,19] and was grown in BHI supplemented with 2 mg/ml kanamycin. *S. aureus* strain Phillips, a clinical isolate from an osteomyelitis case [11], was grown in TSB (Difco) at 37° C.

Cloning and construction of expression plasmids. The nucleotide sequence encoding the Ace A or A+B domains (FIG. 1a) was obtained by PCR using a thermocycler (Perkin Elmer Cetus 480) and chromosomal DNA [20] from *E. faecalis* strain EF1 as the template. Primers (USB Life Technologies) were designed to amplify nucleotides 94 (5' GCAGGATCCGAATTGAGCAAAAGTTCAATC 3') (SEQ ID No. 6) to 1101 (5' GCAGTCGACTCAGTCTGTCT-TCACTTGTTTC 3') (SEQ ID No. 7) of the A domain and nucleotides 94 (5' GCAGGATCCGAATTGAGCAAAAGT-TCAATC 3') (SEQ ID No. 6) to 1750 (5' GCAGTCGACT-CATGGCTGTTTTTTCTCAGTTGTAG 3') (SEQ ID No. 9) of the A+B domain sequence as determined from the nucleotide information obtained from TIGR. The resulting gene fragments were subcloned into pQE-30 (Qiagen Inc., Chatsworth, Calif.), transformed into *Eschericia coli* strain JM101 and analyzed by automated DNA sequencing (University of Texas Medical School, Houston, Tex.). Construction of the Cna plasmids that yield the recombinant proteins in FIG. 1d has been described previously [5].

Expression and purification of recombinant proteins. Recombinant polyhistidine Ace A domain fusion protein was produced by inoculating 1 L cultures of LB (supplemented with 100 μg/mL ampicillin) with 40 mL of an overnight culture of the A domain expression construct described above. Following 2.5 hrs of growth at 37° C., IPTG was added to a final concentration of 0.2 mM to induce protein expression and the cultures were allowed to grow for another 3 hrs. Bacteria were harvested by centrifugation, the supernatant decanted, and the cell pellets resuspended in PBS before being stored at −80° C. The suspension was later thawed in an ambient-temperature water bath for 30 minutes and the cells lysed using a French press. Insoluble cell debris was removed by centrifugation at 28,000×g for 20 minutes followed by filtration through a 0.45 μm membrane. Recombinant Ace A domain was then initially purified using metal-chelating chromatography. Bacterial lysates were applied to a 5 mL Ni$^{2+}$-charged HiTrap chelating column (Pharmacia Biotech Inc., Piscataway, N.J.) and bound protein eluted with a 200 mL linear gradient of 0–200 mM imidazole in 4 mM Tris-HCl, 100 mM NaCl, pH 7.9 at a flow rate of 5 mL/min. Fractions corresponding to recombinant Ace A domain, as determined by SDS-PAGE, were pooled and dialyzed against 25 mM Tris-HCl, pH 8.0 before further purification by ion-exchange chromatography. Dialyzed protein was applied to a 5 mL HiTrap Q column (Pharmacia Biotech Inc.) and bound protein eluted with 200 mL linear gradient of 0–0.5 M NaCl in 25 mM Tris-HCl, pH 8.0 at a flow rate of 5 mL/min. Fractions containing purified Ace A domain were identified by SDS-PAGE and estimated to be >90% pure. Production and isolation of recombinant Cna proteins was performed as described previously [5].

Preparation of Ace A domain polyclonal antibodies. Purified Ace A domain was dialyzed against 10 mM Na$_2$HPO$_4$, 150 mM NaCl, pH 7.4 (PBS) before being sent to HTI Bio Products (La Jolla, Calif.) for immunization in rabbits and production of polyclonal antisera. For some experiments, IgGs were purified from both immune and pre-immune serum by chromatography using Protein A sepharose (Sigma).

Western blot analysis. Mutanolysin surface extracts [21] were prepared from *E. faecalis* strains EF1 and EF2 grown at 46° C. and analyzed by Western blot analysis. The presence of Ace was detected following incubation with anti-Ace A domain polyclonal antiserum, followed by goat anti-rabbit IgG horseradish peroxidase, and development in the presence of 4-chloronaphthol and H$_2$O$_2$.

Bacterial adherence assays. ELISA plates were coated with 5 μg of Type I collagen in 100 μL PBS per well overnight at 4° C. Wells were then washed 3 times with PBS and then blocked with 1% BSA in PBS for 1 h before the addition of bacteria. Bacteria (*E. faecalis* grown at 46° C., *S. aureus* at 37° C.) were harvested from liquid cultures and diluted to a concentration having an absorbance of 1.0 at 600 nm in PBS (approx. 5×10$^8$ bacteria/ml) before being labeled with FITC [22]. 100 μL of labeled bacteria were added per well and the plates were incubated at 37° C. for 1 h. The total fluorescence (F$_{total}$) per well was measured after a 1 h incubation using a Fluoroskan II fluorescence reader (Labsystems, Beverly, Mass.), with $\lambda_{ex}$=485 nm and $\lambda_{em}$=535 nm. The wells were washed with PBS three times to remove unbound bacteria and the remaining fluorescence (F$_{test}$) measured. Adherence was calculated as follows: Adherence=F$_{test}$/F$_{total}$. For the data shown in FIG. 6, adherence of labeled cells in the absence of antibodies was normalized to 100%. BSA-coated wells were used as negative controls. For inhibition assays, FITC-labeled bacteria were first incubated with anti-Ace A domain IgG for one hour at 37° C. before addition of the mixture to the collagen-coated wells.

Absorption spectroscopy. Absorption measurements were taken at ambient temperature (23+2° C.) on a Beckman DU-70 UV/vis spectrophotometer using a 1.0 cm pathlength cuvette. All spectra were corrected for background noise. Molar extinction coefficients of each protein were calculated using values of Pace et al. for the extinction coefficients of the individual residues [23].

Circular dichroism spectroscopy. Far-UV CD data were collected on a Jasco J720 spectropolarimeter calibrated with d-10-camphorsulfonic acid, employing a bandpass of 1 nm and integrated for 4 sec at 0.2 nm intervals. All samples were less than 15 μM in 0.1 mM Na$_2$HPO$_4$, 1 mM NaCl, pH 7.0. Spectra were recorded at ambient temperature in cylindrical 6.5 mm pathlength cuvettes. Twenty scans were averaged for each spectrum and the contribution from buffer was subtracted. Quantitation of secondary structural components was performed as described in reference 8. The validity of these results was confirmed by comparison with the results obtained from X-ray crystallographic data for Cna 151–318: the breakdown of secondary structural components is nearly identical for the solid- and solution-phase structures (Table 1).

TABLE 1

Summary of Secondary Structural Components.

| species | α-helix | β-sheet | other |
|---|---|---|---|
| Ace A | 0.07 ± 0.02 | 0.50 ± 0.13 | 0.43 ± 0.13 |
| Cna A | 0.09 ± 0.04 | 0.49 ± 0.02 | 0.42 ± 0.09 |
| Cna 151-318 | 0.12 (0.08)$^a$ ± 0.04 | 0.49 (0.53) ± 0.04 | 0.39 (0.39) ± 0.13 |

$^a$Data in parentheses are those obtained from X-ray crystallography [7].

Surface Plasmon Resonance Spectroscopy. Analyses were performed using the BIAcore 1000 system. Bovine Type I collagen predissolved in 0.1 M HCl (Collagen Corp., Fremont, Calif., USA) was immobilized on a CM5 sensor chip as described previously [5]. Recombinant proteins in 150 mM NaCl, 50 mM HEPES, 0.005% P-20 surfactant, pH 7.4 were flowed over multiple flow cells containing different amounts of immobilized collagen. The slowest flow rate (1 μL/min) specified for the instrument was employed. Even at this rate, however, the association and dissociation of the recombinant Ace A domain protein with the collagen-coated surface was too rapid to be quantitated. Specific binding response data were obtained by subtracting the response obtained using a flow cell that was not coated with collagen. Analytical conditions were as described previously [24,25]. No mass transport effects were observed in these measurements. The data for the construction of the Scatchard plots were obtained from the equilibrium portion of the SPR sensorgrams (e.g., the response at approximately 900 s in the Ace sensorgram of FIG. 4a). Values for the collagen-bound protein, v$_{bound}$, and concentration of unbound protein, [P]$_{free}$, are calculated from:

$$v_{bound} = \frac{R_p m_c}{R_c m_p} \quad (1)$$

$$v_{total} = \frac{10^{12} [P]_o vol_{flowcell} m_c}{R_c area_{flowcell}} \quad (2)$$

$$[P]_{free} = [P]_o \frac{v_{total} - v_{bound}}{v_{total}} \quad (3)$$

wherein in equation 1, R is the SPR response, m is the molecular mass, P is the protein, C is collagen; and in equation 2, [P]$_o$ is the concentration of total protein, vol$_{flowcell}$ is the volume of sample in the flow cell, and area is the surface area of the flow cell. Plotting v$_{bound}$/[P]$_{free}$ vs. v$_{bound}$ yields the plot shown in FIG. 4b. The negative reciprocal of the slope yields the dissociation constant, K$_D$, and the x-axis intercept is equivalent to the number of sites, n, in collagen at which the MSCRAMM protein binds.

Results *Enterococcus faecalis* Ace is a mosaic protein having critical sequence homology with *Staphylococcus*

*aureus* Cna. In an attempt to identify novel collagen binding proteins, we searched microbial genome databases for amino acid sequences which have significant similarity to that of Cna 151–318 (previously referred to as Cna M19 [4–8]), the central region of the A domain of the *S. aureus* collagen-binding MSCRAMM (FIG. 1c). A significant match was recorded in the *E. faecalis* genome database. The complete sequence of the gene encoding this protein, which has been given the working name Ace[3] (adhesin of collagen from *E. faecalis*), was obtained from The Institute for Genomic Research (TIGR) and was present on contig gef #6285 (TIGR, personal communication). Translation of the nucleotide sequence revealed a 74 kDa protein which has a structural organization very similar to that of MSCRAMMs from other Gram-positive bacteria (FIG. 1a). A possible signal sequence involving the first 31 amino acids is followed by a 335 amino acid long A domain. The B domain is composed of 4.5 tandemly repeated 47-residue units of >90% identity. The C-terminus region is composed of a putative cell wall-associated domain rich in proline residues and contains the cell wall-anchoring LPXTG consensus sequence [26]. An 18 amino acid hydrophobic transmembrane region followed by a short cytoplasmic tail represents the C-terminal end of the protein.

PCR primers were designed to amplify the nucleotide sequence encoding the A or A+B domains of ACE from *E. faecalis* strain EF1. The resulting PCR fragment for the A domain corresponded to the same size fragment encoded by strain V583 [27] in the TIGR sequence. However, the PCR fragment for the A+B domains construct was approximately 300 base pairs smaller than expected. DNA sequence analysis revealed that the ace gene from strain EF1 contained only 2.5 B domain repeat units, whereas 4.5 B domain repeat units were present in the sequence of strain V583. With the exception of having two fewer B domain repeat units, the DNA sequence of ace from strain EF1 was greater than 95% identical to that of strain V583.

A central region (residues 174–319) in the A domain of *E. faecalis* Ace (from either strain EF1 or V583) has a high degree of sequence similarity to residues 151–318 of the *S. aureus* Cna protein. Within this span of amino acids, 27% of the residues are identical to residues in Cna 151–318 and an additional 29% are similar (FIG. 1e). Significant similarity (46%) continues throughout the A domain of Ace and the corresponding region of the Cna A domain; outside the A domains, however, there is no obvious sequence homology between Ace and Cna.

Structural models suggest a similar folding motif for *S. aureus* Cna 151–318 and *E. faecalis* Ace 174–319. Modeling of Ace 174–319 onto the structure determined for Cna 151–318 gave the structure shown in FIG. 2a. To obtain the best sequence alignment, three one-residue gaps and one three-residue gap were introduced into the sequence of Ace 174–319 and a two-residue gap was introduced into the sequence of Cna 151–318. It is noteworthy that the polypeptide region in Ace covered by residues 174–319 is predicted to fold in a "jelly-roll" as Cna 151–318 does, even though a substantial number of the amino acids involved are different as shown in FIG. 2a, where the residues conserved between the two proteins are presented in cyan segments and the residues unique to Ace 174–319 are presented in gray. The more substantial residue differences are located in loops connecting the β-strands. When the polypeptides of Ace 174–319 and Cna 151–318 are overlaid (FIG. 2b), the β-strands are almost identical and the most notable folding differences are observed in the loops.

A trench present on the surface of the Cna 151–318 structure has been identified as the collagen-binding site and can accommodate a collagen-like triple-helical peptide [7]. The structure predicted for Ace 174–319 contains a trench in the same orientation, as highlighted in FIG. 2c. Approximately half of the Cna trench-lining residues are conserved in Ace. Of the conserved putative Ace trench residues shown in blue in FIG. 2c, four (Y180, R193, F195, and N197) shown to be critical for collagen binding in Cna [9]. Another residue (K237) known to be critical for collagen binding in Cna 151–318 is not conserved in Ace and is one of the residues shown in green (FIG. 2c). These modeling studies, based on the known collagen-binding MSCRAMM, Cna, suggested that Ace (1) can act as a collagen adhesin and (2) possesses a trench-shaped binding site.

A recombinant form of Ace A domain has a β-sheet structure and binds collagen. A recombinant form of the Ace A domain was expressed as a fusion protein with a N-terminal His-tag. This protein was soluble and could be purified by chromatography on a $Ni^{2+}$ charged IDA-sepharose column and a anion-exchange column. Analysis of the protein by CD spectroscopy gave a spectrum with a maximum at 195 nm and a minimum at 217 nm (FIG. 3). This spectrum was qualitatively similar to that of the intact A domain and residues 151–318 of Cna. Deconvolution of the spectra revealed very similar compositions of secondary structure for each of the three proteins dominated by β-sheet structures and with a small α-helical component (Table 1).

We used surface plasmon resonance spectroscopy (SPR) to analyze the predicted collagen-binding activity of Ace. The sensorgrams in FIG. 4a show that recombinant Ace A domain and Cna 151–318 both bind to Type I collagen immobilized on a BIAcore sensor chip. However, the kinetics of the two interactions were dramatically different. The on- and off-rates of the Ace/collagen interaction were far too rapid to be determined from these measurements, whereas the association and dissociation rates of the binding of Cna 151–318 to collagen were slower and measurable [24,25].

Scatchard analysis of SPR equilibrium binding data from increasing concentrations of Ace flowed over immobilized collagen yielded a linear plot (FIG. 4b), indicating five copies of a single class of Ace A domain binding sites exist in Type I collagen. The calculated dissociation constant (48 µM) indicated a relatively weak affinity. In contrast, our earlier analyses of the binding of Cna 151–318 and intact Cna A domain to Type I or Type II collagen yielded a concave upward Scatchard plot, indicating the presence of several classes of Cna binding sites in these collagens [24,25,28].

Ace is a collagen-binding MSCRAMM. Analyses of the ace gene sequence revealed many elements including the cell wall-anchoring motif characteristic of cell wall-associated surface proteins from Gram-positive bacteria. This raised the question: Is Ace a functional collagen-binding MSCRAMM present on the surface of enterococci? We have previously demonstrated that most strains of *E. faecalis* can adhere to a collagen substrate after growth at 46° C., indicating the presence of collagen-binding MSCRAMMs on the bacterial surface [12]. Western blot analyses of proteins released from *E. faecalis* strain EF1 and EF2 grown at 46° C. by digestion with mutanolysin demonstrated the presence of two major bands reacting with antibodies raised against the Ace A domain, whereas proimmune sera did not react with any protein (FIG. 5). The larger band migrated at approximately 80 kDa and most likely represented the full-length Ace protein, whereas the smaller band may represent a proteolytically processed form of the protein. Ace from strain EF1 has an expected molecular mass of only 60 kDa. The difference between this mass and the apparent molecular mass observed in FIG. 5 may be due to the acidic nature (pI=4.3) of the Ace protein.

Antibodies to Ace A domain were tested for their ability to inhibit the adherence of enterococcal cells to a substrate of Type I collagen. As shown in FIG. 6a, as little as one µg/mL of anti-Ace IgG almost completely inhibited bacterial adherence to immobilized collagen, whereas there was no effect of the pre-immune IgG over the range of concentrations examined. Neither immune or pre-immune IgG types had any effect on S. aureus strain Phillips adherence to Type I collagen, indicating that anti-Ace A domain antibodies did not interfere with the binding of Cna to collagen (FIG. 6b). Taken together, these results demonstrate that Ace is present on the surface of E. faecalis cells and acts as a collagen adhesin.

Discussion

An earlier study from our laboratories showed that most strains of E. faecalis adhered to a substrate of Type I collagen when bacteria were grown at elevated temperatures (46° C.), a condition that also retarded growth, but not when grown at 37° C. We now report the identification of a gene, ace, encoding a MSCRAMM, Ace, which may be the agent responsible for the E. faecalis adhesion to collagen.

E. faecalis Ace closely resembles the S. aureus MSCRAMM, Cna, in its domain organization. Both contain a signal peptide, a nonrepetitive A domain, a B domain composed of multiple repeat units, and cell wall-associated, transmembrane, and cytoplasmic domains (FIGS. 1a and 1c). The A domain is present in four of four strains examined: V583, EF1, EF2, and OG1 RFΔGel. Ace from two strains of E. faecalis examined varied in the number of B domain repeat units (V583 has 4.5 B domain repeats; EF1 has 2.5). Similar variation in the number of B domain repeats units has been observed previously for Cna in S. aureus [9].

Module shuffling has been observed in Peptostreptococcus magnus protein PAB and is presumed to occur at recers (recombinant sites in genes that also serve as flexible spacers in the protein) within the nucleotide sequence [29]. Employing de Chateau and Björk's criteria for the identification of recer sequences (GAA.AAt.CCA.GAt.GAA, (SEQ ID No. 10) translating into the presumably unstructured ENPDE [29]), we identified the recer nucleotide consensus sequence at the boundary between each B domain repeat unit in both sequenced E. faecalis strains, V583 and EF1 (FIG. 1a). No recer sequences were identified in the Ace A domain or in the entire Cna sequence. Although we have no evidence that recombination occurs at the putative Ace recer sites shown in FIG. 1a, module shuffling of a genetic element may explain why the number of Ace B domain repeat units varies among strains of E. faecalis. The role of these B domains is unidentified to date, but it has been shown that the B domain in Cna does not influence the MSCRAMM's collagen-binding capability [8].

Antibodies raised against the Ace A domain effectively inhibited the adhesion of E. faecalis grown at 46° C. to collagen (FIG. 6). Although 46° C. is a nonphysiological condition, antibodies to Ace have been isolated from serum from E faecalis endocarditis patients (unpublished results, B.E.M.), indicating that under some physiologic conditions Ace is expressed in vivo. The failure of anti-Ace antibodies to prevent collagen adhesion by S. aureus was most likely due to the fact that these antibodies did not cross-react well with Cna. This concept is supported by the fact that anti-Ace antibodies failed to react with a recombinant Cna construct in a Western blot (data not shown). In addition, a panel of monoclonal antibodies raised against Cna 151–318 did not cross-react with recombinant Ace A domain.

Not only does the domain organization of Ace resemble that of Cna, but it appears that the A domains of the two MSCRAMMs also may fold similarly. The hypothesis that Ace domain residues 174–319 fold as Cna 151–318 does is derived from sequence homologies and molecular modeling studies (FIGS. 1e and 2a–2c). This is supported by the CD spectra of the Cna and Ace A domains and the deconvolution results from these spectra (FIG. 3 and Table 1). Not only are the A domains of both Cna and Ace composed primarily of β-sheets structures, with a minor α-helical component, but the arrangement of the secondary structural elements in the two MSCRAMMs are alike. This secondary structural organization may be an important factor in the MSCRAMMs' ligand-binding capabilities. Based on the molecular modeling, Ace contains a trench similar to the collagen-binding site identified in Cna 151–318. Furthermore, many of the trench residues in Cna 151–318, including most of those known to affect collagen binding, are conserved in Ace 174–319 (six residues highlighted in blue, FIG. 2c).

Although the models and spectra in FIGS. 2 and 3 suggest similar structures for the Ace A domain and Cna 151–318, the mechanism of binding collagen is apparently distinct for the two proteins. Not only are their respective on- and off-rates to collagen of different magnitudes (FIG. 4a), but their specificities for sites within the collagen macromolecule are also different, as demonstrated by the Scatchard plots of Ace and Cna: the Scatchard plot of Ace is linear (FIG. 4b), but that of Cna 151–318 is distinctly nonlinear [5]. The Ace A domain associates and dissociates with collagen rapidly, binding at five sites in the Type I collagen strand with equal affinity. Under similar analytical conditions, Cna 151–318 and full-length Cna A domain associate and dissociate with collagen much slower and interact more promiscuously with collagen, binding at a great number of sites in the ligand and with a range of affinities [5,28]. We cannot exclude the possibility of lower-affinity interactions occurring between Ace and collagen at Ace concentrations greater than 70 µM, but consider protein concentrations much above 100 µM to approach the boundary between specific and nonspecific protein-ligand interactions. Therefore, we have chosen to study the collagen binding by ACE over the range of MSCRAMM concentrations that have yielded the multiphasic Scatchard plots for Cna.

Although the collagen-binding regions of Cna and Ace may be so similar in structure, it remained unclear what accounted for their very different interaction mechanisms with Type I collagen. One possibility would be that the residues that are conserved in these proteins (particularly those residues in the binding-site trench) are (1) responsible for recognition of a common element within the triple-helical collagen or (2) vital for maintaining the MSCRAMM's gross trench structure. In the first scenario, the binding-trench residues that are not conserved may regulate a particular MSCRAMM's specificity for and affinity to collagen. In the second, the nonconservation of residue K237 and other trench residues in the Ace A domain may result in a more rigid and/or "slippery" binding, trench, in which collagen may fit with little conformational rearrangement of the binding site or ligand. Under such conditions, only a few sites within collagen may be amenable to MSCRAMM binding and rapid interaction rates would be possible. On the other hand, the trench in Cna 151–318 may be more flexible or contain more residues that form hydrogen bonds or hydrophobic patches with collagen; thereby (1) exhibiting slower interaction rates as conformational reorganization occurs during the binding event and (2) providing for suitable contact with a variety of sites in collagen. These results suggest different mechanisms of ligand interactions may exist for MSCRAMMs binding to the same ECM molecule. It is also possible that collagens other than Type I contain high-affinity Ace-binding sites. Identification of the residues critical for collagen binding in *E. faecalis* ACE and the resolution of the Ace A domain crystal structure may provide additional information concerning this new member of the MSCRAMM family.

In conclusion, the results confirmed that Ace is an enterococcal collagen-binding MCSRAMM which may be utilized in methods which advantageously make use of its ability to bind collagen so as to provide compositions based on Ace proteins and antibodies thereto that can be useful in treating or preventing enterococcal infections.

EXAMPLE 2

Ace Attachment to ECM Proteins Collagen Type IV and Laminin in Addition to Collagen Type I Overview Adhesin mediated binding to extracellular matrix (ECM) proteins is a crucial step in the pathogenic process of many bacterial infections. In this study, we constructed an ace disruption mutant in *E. faecalis* strain OG1 RF that showed marked reduction in adherence to collagen types I and IV, and laminin, when compared to the parental OG1 RF strain after growth at 46° C. Polyclonal immune serum raised against OG1 RF derived recombinant Ace A domain reacted with a single ~105 kDa band of mutanolysin extracts from OG1 RF grown at 46° C., while no band was detected in extracts from OG1 RF grown at 37° C., nor from the OG1 RF ace mutant grown at 37° C. or 46° C. IgGs purified from the anti-Ace A immune serum inhibited adherence of 46° C. grown *E. faecalis* OG1 RF to immobilized collagen type IV and laminin as well as collagen type I, at a concentration as low as 1 µg/ml, and also inhibited the 46° C. evoked adherence of two clinical isolates tested. We also showed in vitro interaction of collagen type IV with Ace from OG1 RF mutanolysin extracts on a far-western blot. Binding of recombinant Ace A to immobilized collagen types I and IV and laminin was demonstrated in an ELISA and was shown to be concentration dependent. These results indicate that Ace A mediates the conditional binding of *E. faecalis* OG1RF to collagen type IV and laminin in addition to collagen type I.

BACKGROUND

Collagens, proteoglycans, and structural glycoproteins such as fibronectin and laminin are found in the extracellular matrix (ECM) of all eukaryotic tissues and are frequently exploited for colonization by microbes and initiation of infections (6, 14, 39). Collagen contains a characteristic Gly-X-Y repeating tripeptide sequence where X and Y often are proline and hydroxyproline, respectively. Segments of the collagen polypeptides containing this repeat sequence form characteristic triple helix structures with a rope-like appearance. In mammals, collagen occurs in close to twenty genetically different types, some of which show tissue specific distribution. For example, collagen type IV is found exclusively in basement membranes, whereas collagen type I has a relative broad distribution (17). Laminins, which also occur in several genetically distinct forms, are composed of three polypeptides that are partly associated to form a characteristic cross as revealed by electron microscopy. In the long arm of the cross the three polypeptides are forming a rope-like structure resembling that seen in collagen. The laminins are basement membrane components where they contribute to the structural integrity of the tissue and in the cell signaling (1, 3, 7, 41).

In normal tissues, most extracellular matrices are covered by epithelial or endothelial cells and hence are not available for binding. However, any type of trauma that damages host tissues may expose the extracellular matrix and allow microbial colonization and infection. During the past decade, several microorganisms including streptococci and staphylococci have been shown to express surface components that recognize extracellular matrix molecules including collagen and laminin (6, 13–16, 21, 31, 32, 34–36).

Our earlier investigations oh adherence of clinical isolates of *Enterococcus faecalis*, regardless of their source, showed that most isolates displayed conditional binding to collagen type I (CI), collagen type IV (CIV), and mouse laminin (LN). The adherence phenotype was termed conditional because it was observed after growth at 46° C., but not, for most isolates, after growth at 37° C. (40); in these experiments, we defined adherence as being present if >5% of total labeled cells were bound to the ECM coated wells. We then identified a putative collagen binding gene, ace, in the *E. faecalis* strain V583 partial database (25) and based on structural similarities with Cna of *Staphylococcus aureus*, followed by some biochemical and biophysical characterization, we assigned a CI binding function to Ace (25).

In the present investigation, we constructed an *E. faecalis* strain OG1 RF ace mutant and showed that it is deficient in adherence to CI, CIV, and LN. We also-found that polyclonal anti-Ace A antibodies raised against recombinant OG1 RF derived Ace A protein inhibited adherence of wild type OG1RF to these three ECM proteins. Using far-western blots and solid phase ELISAs, we confirmed in vitro Ace A binding to CI, CIV, and LN.

Materials and Methods:

Bacterial strains and culture conditions: Strains and plasmids used in this study are listed in Table 1. *E. faecalis* strain OG1 RF, a derivative of *E. faecalis* OG1, and *E. faecalis* strain V5B3 have been described previously (19, 26). *E. faecalis* strain MC02152, isolated from a patient with endocarditis, was kindly provided by J. M. Steckelberg, Mayo Clinic, MN. *Escherichia coli* cells were grown in Luria-Bertani (LB) broth or on LB agar with appropriate antibiotics overnight at 37° C. Enterococci were grown either in brain heart infusion (BHI) broth/agar or in Todd Hewitt broth/agar (DIFCO Laboratories, Detroit, Mich.) overnight at 37° C. for routine purposes and at 46° C. for adherence assays. Antibiotics were used at the following concentrations: kanamycin at 50 µg/ml, and ampicillin at 50–100 µg/ml for *E. coil*; kanamycin at 2000 µg/ml for the *E. faecalis* mutant. All constructs were given TX numbers as shown in Table 2. Plasmids from these constructs were assigned respective pTEX numbers.

Chemicals: Collagen types I and IV were purchased from Sigma Chemical Co. (St. Louis, Mo.). Mouse laminin (isolated from the EHS-sarcoma) was purchased from Life Technologies (Grand Island, N.Y.). Tran $^{35}$S-label and bovine serum albumin (BSA) were purchased from ICN Biomedicals Inc. (Costa Mesa, Calif.). Oligonucleotide primers were purchased from Life Technologies. PCR buffers were purchased from Invitrogen Corporation (Carlsbad, Calif.). All other chemicals used in the investigation were of molecular biology grade.

General DNA techniques: DNA preparation, purification, restriction digestion, agarose gel electrophoresis, and ligation were performed using standard methods (27). Chromosomal DNA from *E. faecalis* was prepared according to the method described by Murray and colleagues (19). PCR amplification of DNA was performed on a DNA thermal cycler (Perkin-Elmer Corp., Norwalk, Conn.). Preparation of agarose plugs, PFGE, and Southern blot analysis were carried out according to previously described methods (18, 23). Radioactive DNA probes were prepared by random primed labeling according to the protocol supplied (Life Technologies). Electroporation of *E. coli* and *E. faecalis* was carried out using a Bio-RAD Gene Pulser as described previously (12). Isopropylthio-β-D-galactoside (IPTG) and 5-bromo-4-chloro-3-indolyl-β-galactoside (X-Gal) were used at 0.5 mM and 80 μg/ml, respectively. DNA sequencing reactions were performed by the Taq dye-deoxy terminator method on an automated ABI Prism sequencer (Applied Biosystems, Foster city, CA).

Construction of a mutation in the ace gene of *E. faecalis* OG1 RF: The *E. faecalis* OG1 RF ace gene was disrupted using a suicide vector pTEX4577 (29) containing an internal fragment of the ace gene. A 1003 bp internal fragment (coding for the A domain of Ace of *E. faecalis* strain OG1 RF) was amplified by PCR using AceF2 (5'-GAGCAAAAGTTCAATCGTTGAC-3') (SEQ ID No. 11) and AceR3 (5'-GTCTGTCTTTTC-ACTTGTTTCT-3') (SEQ ID No. 12) primers and cloned into the TA cloning vector pCR®2.1 (Invitrogen Corp., Carlsbad, Calif.) resulting in TX5252. A 1100 bp XhoI-KpnI DNA fragment from pTEX5252 was recloned into a pBluescript derivative pTEX4577 and the resulting recombinant plasmid was designated as pTEX5253. Competent cells of *E. faecalis* OG1RF were electroporated with 5 μg of purified pTEX5253 in 2 μl sterile water (23). Transformants showing growth on Todd Hewitt agar supplemented with 2000 μg/ml kanamycin were selected and one was designated as TX5256. Chromosomal DNA from agarose plugs was analyzed by PFGE after NotI or SmaI restriction digestion and hybridization to confirm the disruption. To further confirm the location of pTEX4577 within ace, chromosomal DNA from TX5256 was PCR amplified using the AceF2 or AceR3 primers and T7 or T3 primers from pTEX4577 and the resulting PCR products were sequenced. To test for stability of this disruption mutation, OG1RF ace::pTEX5253 (TX5256) was grown overnight at 37° C. or 46° C. in BHI broth without kanamycin, then reinoculated into BHI broth, grown again overnight two times, and then plated on BHI agar. Approximately 3000 colonies grown on BHI agar were sub-patched on BHI agar supplemented with 2000 μg/ml kanamycin to screen for colonies that had lost resistance to kanamycin.

Adherence assay: Adherence to CI, CIV, and LN was tested by a previously described assay with some modifications (40). Bacteria were streaked from freezer vials onto BHI agar and incubated at 37° C. overnight. A few colonies were picked, resuspended in BHI, and 1×10⁸ CFU were inoculated into 5 ml BHI broth with 10 μCi/ml of Tran ³⁵S label. The cultures were grown at 46° C. for 16 hours, and then harvested by centrifugation at 3000 rpm for 15 minutes. The cell pellets were washed three times in PBS buffer and resuspended in 0.1% Tween-80, 0.1% BSA in PBS. The cell density was adjusted to an $OD_{600}$. One microgram of ECM proteins in a total volume of 50 μl PBS was used to coat Immulon 1 Removawells (Dynatech Labs, Chantilly, Va.) and incubated at 4° C. overnight. After decanting, the wells were blocked with 200 μl of 0.2% BSA in PBS at 4° C. for 2 hours, and then washed with PBS three times. A total volume of 50 μl of labeled bacteria were added into each well and incubated at room temperature for two hours with gentle shaking at 70 rpm. The wells were washed with 0.1% Tween-80, 0.1% BSA in PBS three times. Each detachable well was separated and placed in a vial with 2 ml scintillation liquid and counted in a liquid scintillation counter (LKB Wallace, San Francisco, Calif.). Fifty micro liters of labeled bacteria (adjusted to an $OD_{600}$ of 0.2) were counted to determine the total amount of radioactivity added to each well. Adherence percentage was calculated using the formula (radioactivity of bound cells/radioactivity of total cells added)×100. The assays were performed in duplicate. Isolates were considered to adhere to ECM proteins if >5% of total labeled cells bound to the well.

Cloning, expression and purification of Ace A from OG1 RF: A 1008 bp DNA fragment coding for the complete A domain was amplified from pTEX5252 (derived from OG1RF) using AceFc (5'-CAGAA CTCGAGTTGAGCAAAAGTTCAATC-3') (SEQ ID No. 13) and AceRc (5'-TGGA GGTACCCTAGTCTGTCTTTTCACTTG-3') (SEQ ID No. 14) primers (introduced restriction sites are underlined), cloned into pBAD/HisA expression vector (Invitrogen) followed by electroporation into the *E. coli* host LMG194, and one of the resulting colonies (designated as TX5254) was verified for fidelity of the sequence and confirmed as correct by sequencing. Following electrophoresis of lysates on 10% NuPAGE Bis-Tris gels (NOVEX, San Diego, Calif.), western transfer was carried out according to the protocol supplied by NOVEX and His tagged recombinant protein detected with anti-His (penta) antibodies (Qiagen Inc., Valencia, Calif.).

Recombinant Ace A domain was overexpressed by inoculating one-liter of LB with 10 ml of overnight culture of TX5254. Following 2.5 hours of growth at 37° C., arabinose was added to a final concentration of 0.2% to induce protein expression, and incubation was continued for an additional 6 hours. The bacterial cell pellet was lysed by sonication in denaturing lysis buffer (8 M urea, 0.1 M $NaH_2PO_4$, 0.01 M Tris-HCl [pH 8.0]) containing 5 mM imidazole and the supernatant was purified using metal chelating ($Ni^{2+}$) chromatography. The bound proteins were washed with 8 M urea, 0.1 M NaH2PO₄, 0.01 M Tris-HCl [pH 6.3] and neutralized with renaturing buffer (50 mM Tris-HCl, 50 mM NaCl, 50 mM $NaH_2PO_4$ [pH 8.0]); after washing with renaturing buffer containing 20–40 mM imidazole, the recombinant protein was eluted with a linear gradient of 50–400 mM imidazole in renaturing buffer and the fractions were analyzed by SDS-PAGE. Fractions containing eluted recombinant Ace A were pooled, dialyzed against 25 mM Tris-HCl [pH 8.0], concentrated by lyophilization and repurified using metal chelating ($Ni^{2+}$) chromatography. Purified recombinant Ace A protein showed a single band on SDS-PAGE.

Production of rabbit polyclonal serum: After verifying a single reacting band of His-tagged recombinant Ace A on a western blot probed with anti-His (penta) antibodies (Qiagen Inc.), this protein was used to raise polyclonal antibodies by immunization of rabbits at Bethyl Laboratories Inc. (Montgomery, Tex.) and stored at −70° C. Antibody titers of sera were determined by ELISA with preimmune serum as control.

Protein extraction and western blotting: Protein extracts from *E. faecalis* OG1RF was prepared using mutanolysin (Sigma, St Louis, Mich.). *E. faecalis* OG1RF cells grown at 37° C. and 46° C. were washed and resuspended in 1/10 volume of 0.02 M Tris-HCl [pH 7.00]; 0.01 M $MgSO_4$ buffer containing 100 mM PMSF. Mutanolysin was added to a final concentration of 5 units/1 $OD_{600}$ of cells and incubated at 37° C. for one hour in a rotating shaker. The supernatant collected after centrifugation at 12000 rpm for 15 minutes was concentrated by lyophilization. Protein concentrations were estimated by BCA assay (PIERCE, Rockford, Ill.). Mutanolysin extracts from *E. faecalis* OG1 RF wild type and Ace insertion mutant (TX5256) were electrophoresed on 4–12% NuPAGE Bis-Tris gels (NOVEX, San Diego, Calif.) under reducing conditions in MOPS buffer, and transferred to a polyvinylidene difluoride (PVDF) membrane. Electrophoresis and transfer were carried out according to the protocol supplied by NOVEX. Membranes were then incubated with either anti-Ace A polyclonal antiserum or preimmune serum (antibody I) followed by Protein A horseradish peroxidase conjugate (antibody II), and developed with of 4-chloronaphthol in the presence of $H_2O_2$.

Far-western blot assay: Mutanolysin-PMSF extracts from the parental *E. faecalis* OG1RF and its ace insertion mutant (TX5256) were electrophoresed on 4–12% NuPAGE Bis-Tris gel (NOVEX, San Diego, Calif.) under non-reducing conditions in MOPS buffer, and transferred to a PVDF membrane. After overnight renaturing in blocking buffer, the membrane was further incubated with 10 µg/ml of CIV for about 16 h at 4° C. with gentle shaking. Bound CIV on westerns was detected using anti-collagen type IV monoclonal antibodies (Sigma) followed by horseradish peroxidase conjugated goat anti-mouse IgG antibodies (Life Technologies Inc.), and developed with 4-chloronaphthol in the presence of $H_2O_2$.

Elution of antibodies specific to Ace: Because the Ace immune serum previously described (25) was found to react with several bands, we eluted Ace A specific antibodies from anti-Ace (OG1RF) rabbit immune serum using the method described below and used in the adherence inhibition assay. Recombinant Ace A protein was electrophoresed on 10% NuPAGE Bis-Tris gels (NOVEX) and transferred to a PVDF membrane. Membranes were blocked with 5% skimmed milk and incubated with polyclonal serum raised against recombinant Ace A of OG1 RF. Following visualization of the antibodies bound to Ace on a cut strip using the procedure described in the previous section, the area containing the antigen-anti-Ace antibody complex was excised and incubated with 10 ml of 100 mM glycine [pH 2.5] for 15 min at room temperature to elute Ace-specific antibodies. After neutralization with 1 ml of 1 M Tris [pH 8.0], the solution was transferred to a clean tube and stored at −20° C. until use (8).

IgG purification and Inhibition of adherence: IgGs were purified from both preimmune rabbit serum and polyclonal immune rabbit serum raised against recombinant Ace by affinity column chromatography using Immunopure® (G) IgG purification kit as per the supplied protocol (PIERCE). Labeled bacteria were incubated with varying concentrations of either preimmune rabbit IgGs or anti-Ace A IgGs for 1 hour at 37° C., centrifuged at 3000 rpm followed by resuspension in PBS with 0.1% Tween-80 and 0.1% BSA to remove excess unbound IgGs, prior to addition of labeled cells to the ECM coated wells in adherence assay described in earlier section. Eluted Ace-specific antibodies were also used in the inhibition assay.

Binding of recombinant Ace to collagens and laminin: Microtiter plates were coated with 10 µg ECM proteins or BSA in 100 µl of PBS, and allowed to incubate overnight at 4° C. Wells were washed five times with PBST (PBS with 0.01% Tween-20). After blocking wells with 5% BSA, wells were again washed. Varying concentrations of recombinant Ace A (1–200 µg/100 µl) in PBS with 0.1% BSA were added to the wells and incubated at 37° C. After 4 hours, unbound protein was removed by washing with PBST. Bound proteins were detected by penta-His monoclonal antibodies (Qiagen Inc.) that recognize the His tag of the recombinant Ace A protein, followed by horseradish peroxidase conjugated goat anti-mouse IgG antibodies (Life Technologies Inc.). Relative binding was measured by monitoring absorbance at 450 nm following the addition of 3, 3', 5, 5',-tetramethyl benzidine and $H_2O_2$.

Results:

Construction of an ace disruption mutation and stability: Following electroporation of OG1 RF with the suicide vector pTEX5253 and selection on kanamycin, 14 recombinant OG1 RF colonies were recovered. DNA from three kanamycin resistant OG1RF derivative colonies was digested with NotI or SmaI, followed by PFGE; hybridization with an ace probe, prepared by amplifying with AceF2 and AceR3 primers, showed two ace hybridizing bands (as expected for insertion duplication mutants since there are single NotI and SmaI restriction sites in pTEX5253). OG1 RF processed the same way showed a single hybridizing fragment One of these colonies was designated as TX5256. The correct insertion, resulting from integration of pTEX5253, was also verified by sequencing of the PCR product amplified from TX5256 genomic DNA using AceF2 and T7 primers, and found to have occurred at nucleotide 1101.

All colonies of TX5256 tested after passing through multiple generations without antibiotic selection retained the ability to grow on BHI agar supplemented with 2000 µg/ml kanamycin indicating stability of this mutation.

Adherence of the OG1RF ace mutant (OG1RF ace::pTEX5253): Adherence of OG1RF and the mutant TX5256 to ECM proteins (CI, CIV, and LN) was tested. The ace mutant grown at 46° C. showed a 6.5 fold decrease in percentage of binding to CI (from 21.1% to 3.3%) when compared to OG1 RF. Similarly, the ace mutant grown at 46° C. showed a substantial decrease in adherence to CIV (27.4 fold decrease relative to OG1 RF) and LN (32.9 fold decrease relative to OG1RF) (FIG. 7). This reduced adherence was also found in two other ace disrupted kanamycin resistant colonies tested (data not shown).

Western analysis of mutanolysin preparations of *E. faecalis* OG1RF and the OG1RF ace mutant: Anti-Ace A polyclonal immune rabbit serum reacted with a single ~105 kDa band of mutanolysin-PMSF extracts prepared from 46° C. grown OG1 RF, whereas no bands were detected from mutanolysin-PMSF extracts of 37° C. grown OG1 RF (FIG. 8A). The apparent observed molecular weight is higher than predicted (calculated based on sequence described in companion paper), perhaps due to the acidic nature of the Ace protein (25) that has a pI of 4.2 as calculated from the amino acid sequence. The OG1 RF ace mutant (TX5256) grown at 46° C. demonstrated loss of ~105 kDa immunoreactive protein band seen in OG1RF grown at 46° C. (FIG. 8B).

Influence of anti-Ace IgGs on adherence of *E. faecalis* OG1RF to ECM proteins: We have previously reported inhibition of adherence of a 46° C. grown *E. faecalis* OG1 RF gelE mutant (29) to CI by IgGs purified from *E. faecalis* EF1 anti-Ace A antibodies (25). However, that serum reacted with several bands on western blots. Using IgGs that were purified from *E. faecalis* OG1RF anti-Ace A polyclonal immune serum, we tested the influence of anti-Ace IgGs on adherence of OG1 RF to CIV and LN as well as to CI. Using 0.001 µg/ml to 100 µg/ml of either purified preimmune IgGs or purified anti-Ace IgGs inhibition of adherence was tested. Preincubation with as little as 1 µg/ml of anti-Ace IgGs considerably inhibited adherence to CIV and LN, in addition to CI, whereas preimmune serum had no effect on adherence over the range of concentrations tested (Table 3). Antibodies eluted from recombinant Ace A were also tested in the adherence inhibition assay. As shown in FIG. 9, eluted antibodies at 1 µg/ml concentration eliminated 46° C. grown OG1 RF adherence to the three ECM proteins, CI, CIV, and LN (~20 fold decrease relative to OG1 RF).

We also examined the ability of these anti-Ace A IgGs (purified from rabbit polyclonal immune serum raised against OG1RF derived recombinant Ace A) to inhibit adherence of two clinical *E. faecalis* strains V583 and MC02152 to CI, CIV, and LN that showed conditional binding at 46° C. Preincubation of these strains with anti-Ace A IgGs at 20 µg/ml concentration inhibited adherence to CI, CIV, and LN; relative to preimmune serum, adherence decreased by about 8.5 to 13.4 fold as shown in Table 4. Purified IgGs from preimmune serum had no effect on adherence at this concentration.

Collagen type IV interaction with Ace using far-western: We used far-western analysis and examined CIV interaction with the ~105 kDa Ace protein to determine the direct association of CIV with Ace. Probing of mutanolysin-PMSF extracts (prepared from 46° C. grown OG1RF) on a western blot with CIV, followed by detection with anti-collagen type IV monoclonal antibodies, identified a single ~105 kDa protein band, whereas no band was detected from mutanolysin extracts of the OG1 RF ace mutant (FIG. 10).

Binding of recombinant Ace A domain to ECM proteins: The results from an ELISA demonstrating the binding of recombinant Ace A to immobilized CI, CIV, and LN are shown in FIG. 11. Binding of recombinant Ace protein to the collagens and laminin was found to be concentration dependent and exhibited saturation kinetics. Fibrinogen, to which none of *E. faecalis* isolates bound in our assay (40), was used as a control. The percentage of Ace bound to fibrinogen was the same as to BSA at all the concentrations tested (data not shown). As evident from FIG. 11, binding of Ace A to CIV was slightly greater compared to its binding to CI and LN.

Discussion

We previously showed that the majority of *E. faecalis* isolates adhered, after growth at 46° C., to CI, CIV, and LN (40). An examination of the adherence process revealed that: i) *E. faecalis* strain OG1RF adherence was dependent on the amounts of CI, CIV, and LN in the substrates; ii) OG1 RF adherence to ECM proteins was inhibited after preincubation of the bacteria with soluble ECM proteins; iii) trypsin treatment of the bacteria rendered the cells non-adhesive; iv) digestion of the CI and CIV substrates with collagenase destroyed their ability to support adhesion of strain OG1 RF, whereas bacteria still adhered to collagenase digested laminin substrate and v) scanning electron microscopy of *E. faecalis* OG1 RF adhered to laminin coated wells showed single cells evenly distributed over the substrate (40). We recently identified a gene, ace, in the *E. faecalis* strain V583 partial genome database that encodes a protein with a structural organization similar to the collagen binding MSCRAMM, Cna, from *S. aureus*. Both proteins contain features characteristic of cell wall anchored proteins at the C-terminus preceded by a region composed of B repeats and an N-terminal A region. The A region of Cna contains the collagen binding domain which has a β-barrel structure as revealed by X-ray analysis of protein crystals (37). One of the β-sheets contains a "trench" that was identified as a putative collagen binding site. Computational docking experiments showed that the binding trench could accommodate the rope-like collagen structure (24, 37). The A region of Ace has significant sequence similarity to the corresponding domain of Cna. We therefore expressed a recombinant form of the Ace A region and showed by Circular Dichroism spectroscopy that the secondary structure of Ace and Cna A regions are very similar (25). In fact, computational analysis suggested that the putative ligand binding domain of Ace adopts a structure very similar to that determined for the corresponding domain of Cna with a predicted binding trench. Furthermore, the recombinant Ace A region bound collagen type I and antibodies raised against the recombinant protein inhibited adherence of *E. faecalis* to collagen type I substrate (25).

In the current study, we have characterized the *E. faecalis* specific (2) ace gene from strain OG1 RF and found that an OG1 RF ace mutant showed markedly reduced binding not only to immobilized CI but also to CIV and LN, raising the possibility that the same MSCRAMM is responsible for adherence to the three ECM proteins.

However, since this mutant was generated by a chromosomal insertion, the possibility remains that the inserted plasmid may have had a polar effect on downstream genes that are responsible for some of the observed effect.

To detect the Ace protein in *E. faecalis* OG1RF, we raised polyclonal antibodies against recombinant Ace A of OG1 RF that has been expressed in *E. coli*. These anti-Ace A antibodies detected an ~105 kDa protein in 46° C. grown OG1 RF, but not in 37° C. grown OG1RF; the OG1RF ace mutant was found to lack the ~105 kDa protein. Detection of this anti-Ace reactive band in 46° C. grown OG1 RF mutanolysin extracts, but not in 37° C. grown OG1 RF, correlates with the previously reported conditional (growth at 46° C.) binding (40). We have also sequenced the complete ace gene from OG1 RF (20). The deduced amino acid sequence of OG1 RF Ace adhesin predicts a 75.6 kDa protein, which is ~30 kDa smaller than the observed molecular size on western blot. Similar results were found for Ace proteins of the other *E. faecalis* strains studied in the companion paper (20) as well as for *E. faecalis* EF1 and EF2 (25). This difference may be due to the high acidic nature of the Ace protein (25). Another possibility, that the difference in migration might be due to association of Ace with peptidoglycan seems less likely since mutanolysin was used in our preparations, and mutanolysin treatment is known to free at least some proteins from peptidoglycan (9). However, several lines of evidence strongly indicate that the protein identified in mutanolysin-PMSF extracts is indeed the ace gene product. The evidence includes i) anti-Ace A polyclonal antibodies reacted with a single ~105 kDa band in mutanolysin extracts prepared from 46° C. grown *E. faecalis* OG1 RF; ii) preimmune serum did not react with any band in these extracts; and iii) there was loss of the ~105 kDa protein band in the ace insertion mutant. In a companion paper, we also report that protein size variation among various *E. faecalis* strains corresponds to the number of B repeats (20).

To confirm the direct involvement of Ace, and not possible downstream gene products, in 46° C. evoked adherence of *E. faecalis* to CI, CIV, and LN, we tested the ability of anti-Ace A IgGs to inhibit binding of *E. faecalis* OG1RF to these immobilized ECM proteins. The inhibition of the adherence of 46° C. grown OG1RF to CI, CIV, and LN by anti-Ace A IgGs as well as by eluted Ace-specific antibodies provides evidence that the ~105 kDa protein of OG1 RF is the adhesin that mediates binding to these three ECM proteins. We also tested the ability of these IgGs to block adherence of the two clinical strains V583 and MC02152 after growth at 46° C. The inhibited adherence to CI, CIV, and LN by anti-Ace IgGs in these two strains further corroborates involvement of Ace A in strains that showed conditional adherence. We confirmed the CIV affinity to the ~105 kDa OG1 RF Ace protein using a far-western blot and then extended this result to test the binding ability of recombinant Ace A domain to CI, CIV, and LN in an ELISA. In the ELISAs, OG1RF derived recombinant Ace A protein bound to CI as well as to CIV and LN. These ELISA results implicate involvement of the A domain of Ace in binding to CI, CIV, and LN. It is tempting to speculate that the proposed trench on the Ace A domain that has been implicated in binding the triple-helix collagen structure (Y. Xu, R. T. Owens and M. Höök, unpublished results) is also responsible for binding the rigid triple helix structure of the laminin long arm. By analogy, the collagen binding integrins $\alpha1\beta1$ and $\alpha2\beta1$ both which contain a trench in the binding domain have been shown to bind laminin in addition to several types of collagens including CI and CIV (4, 22, 33).

Similar to the *E. faecalis* Ace adhesin, other adhesins have been reported to bind to different ECM proteins. The plasmid encoded outer membrane protein YadA of *Yersinia enterocolitica* has been shown to bind to several types of collagens (28), laminin (5, 30) as well as to fibronectin (38). A 150 kDa fibrinogen binding adhesin of *Porphyromonas* (*Bacteroides*) *gingivalis* also recognized fibronectin (10, 11). Switalski et al. (35) showed that the collagen binding MSCRAMM from *S. aureus* (later identified as Cna) recognizes many types of collagens and McGoven et al. (16) identified a *S. aureus* surface protein that could bind with broad specificity to several ECM proteins including fibrinogen, fibronectin, and vitronectin.

In conclusion, the results from the constructed OG1 RF ace mutant and the inhibition of binding of OG1 RF and of two clinical isolates to all three ECM proteins by anti-Ace A antibodies demonstrate that the A domain of Ace mediates adherence of *E. faecalis* to collagen type IV and laminin in addition to collagen type I. Further supporting evidence for Ace A mediated binding was obtained from the CIV far-western analysis and the ELISAs showing binding of recombinant Ace A to both collagens and laminin. Additional studies will be needed to determine what if any contribution ace may make to the ability of *E. faecalis* to colonize and/or cause infection in man.

TABLE 2

Bacterial strains and plasmids used in this study

| Strains/Plasmids | Relevant characteristics | Reference or source |
|---|---|---|
| Strains | | |
| *E. faecalis* | | |
| OG1RF | Adh$^+$, Fus$^r$, Rif$^r$ | 19, 40 |
| TX5256 | OG1RF ace::pTEX5253. ace insertion disruption mutant of OG1RF. Adh$^-$, Fus$^r$, Kan$^r$, Rif$^r$ | This study |
| *E. coli* | | |
| DH5α | *E. coli* host strain used for routine cloning | Stratagene |
| INVαF' | *E. coli* host strain for cloning of PCR products | Invitrogen |
| LMG194 | *E. coli* strain for expression of recombinant proteins | Invitrogen |
| TX5252 | INVαF' (pTEX5252), Amp$^r$, Kan$^r$ | This study |
| TX5253 | DH5α (pTEX5253), Kan$^r$ | This study |
| TX5254 | LMG194 (pTEX5254), Amp$^r$ | This study |
| Plamids | | |
| pTEX4577 | Derived from pBluescript SK$^-$, used for insertion disruption mutagenesis in enterococci | 29 |
| pBAD/HisA | Expression vector | Invitrogen |
| pTEX5252 | 1003 bp intragenic ace PCR product cloned into pCR ® 2.1 (TA cloning vector) | This study |
| pTEX5253 | 1100 bp XhoI - KpnI intragenic ace fragment from pTEX5252 cloned into pTEX4577 | This study |
| pTEX5254 | 1008 bp OG1RF ace (coding for complete A domain) cloned into pBAD/HisA expression vector | This study |

Adh$^+$: adherence to CI, CIV, and LN, after growth at 46° C.; Adh$^-$: markedly reduced adherence to CI, CIV, and LN. Amp$^r$: ampicillin resistant; Fus$^r$: fusidic acid resistant; Kan$^r$: kanamycin resistant; Rif$^r$: rifampicin resistant. CI: collagen type I; CIV: collagen type IV; LN: laminin.

TABLE 3

Inhibition of adherence of 46° C. grown *E. faecalis* OG1RF to ECM proteins by IgGs purified from anti-Ace A (OG1RF derived) rabbit immune serum

| | | IgG concentration | | | | | |
|---|---|---|---|---|---|---|---|
| | | 0.001 µg/ml | | 0.01 µg/ml | | 0.1 µg/ml | |
| ECM$^a$ | No IgG | PI$^b$ | Anti-Ace$^c$ | PI | Anti-Ace | PI | Anti-Ace |
| CI | 24.6 ± 3.88$^d$ | 25.3 ± 6.78 | 20.1 ± 4.04 | 27.2 ± 4.95 | 18.0 ± 4.09 | 24.5 ± 5.35 | 6.3 ± 1.04 |
| CIV | 29.6 ± 5.31 | 30.3 ± 6.15 | 26.2 ± 8.35 | 28.8 ± 6.12 | 20.3 ± 3.05 | 28.9 ± 6.61 | 7.9 ± 3.49 |
| LN | 32.0 ± 5.91 | 30.2 ± 1.94 | 26.2 ± 5.15 | 31.4 ± 7.89 | 21.8 ± 1.97 | 29.1 ± 4.67 | 8.6 ± 2.04 |
| BSA | 0.9 ± 0.12 | 0.7 ± 0.05 | 0.5 ± 0.09 | 0.1 ± 0.05 | 0.7 ± 0.09 | 0.6 ± 0.08 | 0.5 ± 0.03 |

| | IgG concentration | | | | | |
|---|---|---|---|---|---|---|
| | 1 µg/ml | | 10 µg/ml | | 100 µg/ml | |
| ECM$^a$ | PI | Anti-Ace | PI | Anti-Ace | PI | Anti-Ace |
| CI | 21.6 ± 2.86 | 2.2 ± 0.38 | 22.0 ± 3.12 | 2.3 ± 0.44 | 23.8 ± 3.66 | 1.5 ± 0.37 |

TABLE 3-continued

Inhibition of adherence of 46° C. grown E. faecalis OG1RF to ECM proteins by IgGs purified from anti-Ace A (OG1RF derived) rabbit immune serum

| | | | | | | | |
|---|---|---|---|---|---|---|---|
| CIV | 25.9 ± 8.98 | 3.2 ± 1.89 | 26.6 ± 5.12 | 2.8 ± 0.81 | 26.0 ± 4.73 | 2.2 ± 1.25 |
| LN | 26.4 ± 7.51 | 3.5 ± 1.25 | 28.3 ± 4.25 | 2.8 ± 0.56 | 32.0 ± 3.03 | 2.1 ± 0.49 |
| BSA | 0.8 ± 0.16 | 0.6 ± 0.26 | 0.6 ± 0.26 | 0.7 ± 0.12 | 0.6 ± 0.26 | 0.4 ± 0.06 |

[a]ECM: extracellular matrix proteins; CI: collagen type I; CIV: collagen type IV; LN: laminin; BSA: bovine serum albumin.
[b]PI: IgGs purified from preimmune rabbit serum.
[c]Anti-Ace: IgGs purified from polyclonal anti-Ace A rabbit immune serum.
[d]Values are means of % of cells bound ± standard deviation for six wells. Results are representative of three independent experiments.

TABLE 4

Inhibition of adherence of 46° C. grown E. faecalis clinical isolates V583 and MC02152 to ECM proteins by IgGs (20 μg/ml) purified from anti-Ace A (OG1RF derived) rabbit immune serum

| | E. faecalis V583 | | | E. faecalis MC02152 | | |
|---|---|---|---|---|---|---|
| ECM[a] | No IgG | PI[b] | Anti-Ace[c] | No IgG | PI | Anti-Ace |
| CI | 29.2 ± 1.87[d] | 28.1 ± 2.84 | 3.2 ± 0.17 | 26.0 ± 1.61 | 24.4 ± 1.31 | 2.9 ± 0.46 |
| CIV | 38.1 ± 8.66 | 33.6 ± 6.81 | 2.5 ± 0.17 | 27.7 ± 0.39 | 26.5 ± 1.84 | 2.3 ± 0.13 |
| LN | 29.4 ± 1.96 | 27.6 ± 3.53 | 2.7 ± 0.78 | 26.7 ± 1.22 | 23.5 ± 0.76 | 1.9 ± 0.52 |
| BSA | 0.7 ± 0.10 | 0.6 ± 0.07 | 0.6 ± 0.01 | 0.6 ± 0.12 | 0.5 ± 0.19 | 0.6 ± 0.17 |

[a]ECM: extracellular matrix proteins; CI: collagen type I; CIV: collagen type IV; LN: laminin; BSA: bovine serum albumin.
[b]PI: IgGs purified from preimmune rabbit serum.
[c]Anti-Ace: IgGs purified from polyclonal anti-Ace A rabbit immune serum.
[d]Values are means of % of cells bound ± standard deviation for six wells. Results are representative of three independent experiments.

EXAMPLE 3

Diversity of Ace from Different Strains of Enterococcus faecalis

Overview:

As indicated above, we have identified an E. faecalis sequence, ace, that encodes a bacterial adhesin similar to the collagen binding protein Cna of Staphylococcus aureus. In this study, we confirmed the specificity of ace among 350 enterococci including 161 E. faecalis isolates obtained from different geographic regions as well as from various clinical sources and then sequenced the gene from selected strains. A comparison of nucleotide and deduced amino acid sequences of Ace from 9 E. faecalis strains identified a highly conserved N-terminal A domain, followed by a variable B domain which contains 2 to 5 repeats of 47 amino acids in tandem array, preceded by a 20 amino acid partial repeat Using 17 other strains collected worldwide, the 5'-region of ace that encodes the A domain was sequenced and these sequences showed ≧97.5% identity. Among the previously reported five amino acids critical for collagen binding by Cna of S. aureus, four were found to be identical in Ace from all strains tested. Polyclonal immune rabbit serum prepared against recombinant Ace A derived from E. faecalis strain OG1 RF detected Ace in mutanolysin extracts of 7 out of 9 E. faecalis strains after growth at 46° C.; Ace was detected in four different molecular sizes that correspond to the variation in the B repeat region. To determine if there was any evidence to indicate that Ace might be produced under physiological conditions, we quantitatively assayed sera collected from patients with enterococcal infections for the presence of anti-Ace A antibodies. Ninety percent of sera (19 of 21) from patients with E. faecalis endocarditis showed reactivity with titers from 1:32 to >1:1024; the only two sera which lacked antibodies to Ace A had considerably lower titers of antibodies to other E. faecalis antigens as well. Human derived, anti-Ace A IgGs purified from an E. faecalis endocarditis patient serum inhibited adherence of 46° C. grown E. faecalis OG1 RF to collagen type I, type IV, and laminin. In conclusion, these results show that ace is highly conserved among isolates of E. faecalis with at least 4 variants related to the differences in the B domain, is expressed by different strains during infection in man, and that human derived antibodies can block adherence to these extracellular matrix proteins.

BACKGROUND

Enterococci normally colonize the intestinal tract, but these organisms, particularly Enterococcus faecalis, are also known to cause many clinical infections in humans including septicemia, bacteremia, urinary tract infections and 5–15% of cases of bacterial endocarditis (16). The existing knowledge of the factors that may influence the ability of enterococci to colonize host tissues, translocate across epithelial barriers, and survive in different host environments is rudimentary, but their increasing resistance to multiple antimicrobial drugs makes the study of pathogenesis of these organisms all the more important (19).

Interactions with host cells and colonization of mucosal surfaces are considered to be primary events in the pathogenesis of many infections (2). The pathogenesis of bacterial endocarditis is believed to begin with bacterial adhesion to extracellular matrix (ECM) of damaged heart tissue. Bacterial surface adhesins have been suggested to play a major role in adherence and colonization. Staphylococci are known to bind to a large number of proteins present in the host ECM. Molecular and functional characterization have identified a number of proteins, such as a collagen binding protein, Cna (23), fibronectin binding proteins (13, 30), and fibrinogen binding proteins (3, 5) collectively named microbial surface components recognizing adhesive matrix molecules (MSCRAMMs) (22), that mediate binding to ECM proteins. MSCRAMMs typically share some common structural features i) a short signal sequence followed by a non repetitive region which in most cases is responsible for binding to ECM proteins; ii) a repetitive region that exhibits variation among strains; and iii) a C terminal domain that includes a LPXTG anchoring motif, and a hydrophobic membrane spanning domain followed by a short tail rich in positively charged amino acids (9, 22).

Our recent work identified a gene in *E. faecalis* coding for a putative protein designated as Ace, that has characteristics similar to the collagen binding protein Cna of *Staphylococcus aureus* (26). The Ace sequence from *E. faecalis* strain V583 shows a putative N terminal signal sequence, followed by a 335 amino acid long A domain. The B domain is composed of 4.4 tandemly repeated 47-residue units of >90% identity. A cell wall-associated domain rich in proline residues that contains the cell wall-anchoring LPXTG consensus sequence and a hydrophobic transmembrane region of 18 amino acids, followed by a short cytoplasmic tail represents the carboxy terminal end of the protein (26). This work also localized the collagen type I (CI) binding property of Ace produced by *E. faecalis* strain EF1 to the A domain based on biochemical evidence. More recent results, submitted as a companion paper, demonstrate that Ace mediates the 46° C. evoked adherence of strain OG1 RF to collagen type IV (CIV) and mouse laminin (LN) (20), in addition to CI (26).

In the current study, we have included a large number of enterococcal isolates and studied sequence variation in the *E. faecalis* ace genes. Since most strains of *E. faecalis* exhibit conditional binding (i.e. after growth at 46° C.), we also attempted to detect Ace proteins from bacterial protein preparations made from cultures grown at both 37° C. and 46° C. Finally, in an effort to find evidence of expression of ace under more physiological conditions than 46° C., we have examined sera from patients with enterococcal infections for the presence of antibodies to Ace.

Materials and Methods

Bacterial strains: The enterococci used in this study are from a collection obtained over a 20-year period from various locations in United States of America, Belgium, Thailand, Lebanon, and Chile and included *E. faecalis* (161), *Enterococcus faecium* (171), *Enterococcus hirae* (6), *Enterococcus durans* (5), *Enterococcus casseliflavus* (2), *Enterococcus mundtii* (2), *Enterococcus gallinarum* (1), *Enterococcus solitarius* (1), and *Enterococcus raffinosus* (1). Isolates for this study were selected, in most cases, arbitrarily from our laboratory collection; many of them have been well characterized and are known not to be clonally derived (6, 11, 15, 17, 37). These isolates were from wounds, urine, feces, and blood, including endocarditis. *E. faecalis* strains OG1RF, JH2-2 and V583 have been described previously (12, 18, 28).

Culture conditions: Enterococci were grown in brain heart infusion (BHI) broth/agar (DIFCO Laboratories, Detroit, Mich.) at 37° C. for routine purposes or at 46° C. *Escherichia coli* cells were grown in Luria-Bertani (LB) broth or on LB agar with appropriate antibiotics overnight at 37° C. Concentrations of antibiotics used for *E. coli* were kanamycin at 50 µg/ml, and ampicillin at 50–100 µg/ml.

General DNA techniques: Routine DNA techniques were performed using standard methods (29). Chromosomal DNA from *E. faecalis* was isolated according to the previously described method (18). PCR amplifications were performed using a DNA thermal cycler (Perkin-Elmer Corp., Norwalk, Conn.) and synthetic oligonucleotide primers purchased either from Life Technologies (Grand Island, N.Y.) or from Genosys Biotechnologies Inc. (Woodlands, Tex.).

Colony lysates of enterococci were hybridized with intragenic ace DNA probes obtained by PCR amplification of *E. faecalis* OG1 RF genomic DNA using AceF2a and AceR3a primers as well as AceF3 (SEQ ID No. 18) and AceR2 (SEQ ID No. 25) primers (Table 5). Radioactive DNA probes were prepared by random primed labeling according to the protocol supplied (Life Technologies). Colony hybridization was carried out under low and high stringency conditions using previously described methods (6). Southern blot analysis was carried out, also with an ace probe representing a region with the highest degree of identity to the collagen binding domain of cna from *S. aureus* (26) amplified using AceF3 (SEQ ID No. 19) and AceR2 (SEQ ID No. 25) primers (Table 5), for selected *E. faecalis* and *E. faecium* strains, under low and high stringency hybridization conditions, according to the previously described method (24).

The complete ace gene was sequenced from selected *E. faecalis* strains using primers (SEQ ID Nos. 16–30) listed in Table 5. Part of the region coding for the N terminal Ace A domain was sequenced from other arbitrarily selected *E. faecalis* strains obtained from different geographical regions. DNA sequencing reactions were performed using the Taq dye-deoxy terminator method (Applied Biosystems, Foster City, Calif.). Sequences were aligned using the Sequencher program (Gene Codes Corporation, Ann Harbor, Mich.). DNA sequence data was analyzed, either using the Genetics Computer Group software package (Madison, Wis.) or the DNASTAR software (Madison, Wis.).

Antiserum to the Ace A domain of OG1RF: Cloning and expression of *E. faecalis* OG1RF ace gene, coding for all 335 amino acids of the Ace A domain, generation of polyclonal serum against this purified recombinant Ace A, and reactions of this serum with OG1RF have been described elsewhere (20, see also Table 6).

Western blotting: Protein extracts from 37° C. and 46° C. grown *E. faecalis* cultures were prepared, using the mutanolysin extraction method as described in the companion paper (20). Mutanolysin extracts from *E. faecalis* strains were electrophoresed on 4–12% NuPAGE Bis-Tris gels (NOVEX, San Diego, Calif.) under reducing conditions in MOPS buffer, and transferred to a polyvinylidene difluoride (PVDF) membrane. The presence of Ace protein was detected by incubating with either the anti-Ace A polyclonal antiserum described above or eluted antibodies from human endocarditis serum (antibody I) followed by Protein A horseradish peroxidase conjugate (antibody II), and developing with 4-chloronaphthol in the presence of $H_2O_2$.

Human sera: From our laboratory collection of sera (collected from different medical centers in the United States), four study groups that were grouped based on the diagnosis of infection were selected for analysis. Serum samples known to have antibodies against enterococcal total proteins from previous studies (1, 34, 41) were included. Strains isolated from patients who had donated serum but which were not available to us, and hence could not identified to species in our laboratory, were classified as Enterococcal Species Unknown (ESU). Sera from 21 patients with *E. faecalis* endocarditis (including some corresponding to strains studied here) and four patients with ESU endocarditis constituted one group. A second group consisted of 9 serum samples collected from patients with *E. faecalis* non-endocarditis infections such as bacteremia, urosepsis and osteomyelitis, and three sera obtained from ESU non-endocarditis infections. The third study group consisted of serum samples from 6 patients with *E. faecium* endocarditis, 1 patient with *E. faecium* urosepsis, and 2 patients with streptococcal infections. The final group, consisting of 12 sera obtained from hospitalized patients (HPS) with no knowledge of their diagnosis or of any infection, was included as a non-healthy control group. Available normal human sera (NHS) from our laboratory collection, previously pooled in groups of 2 to 3 from a total of 20 healthy volunteers, were used as a healthy control group.

ELISA: An enzyme linked immunosorbent assay (ELISA) using human sera was performed by a previously described method with some modifications (1). Polystyrene microtiter plates (Dynatech Laboratories Inc., Alexandria, Va.) were coated with 50 ng of recombinant Ace A protein from OG1 RF in 100 µl of PBS, and allowed to incubate overnight at 4° C. Wells were washed five times with PBST (PBS with 0.01% Tween-20). After blocking wells with 3% bovine serum albumin (BSA) at 37° C. in PBST, wells were washed three times with PBST. Each serum was assayed in duplicate in serial dilutions of 1:16 to 1:2048 in 1% BSA. Goat anti-human IgG peroxidase conjugate was used for detection of human antibodies to Ace. Absorbance at 450 nm was measured following the addition of 3,3',5,5',-tetramethyl benzidine and $H_2O_2$. Titers were determined after subtracting values from appropriate negative controls. For control sera, optical density at 450 nm was measured at each dilution. The sum of the average $OD_{450}$ value and two times the standard deviation was calculated for each dilution and used as cut off value for determining sera titers. One-tailed Student's t test was used to compare Ace A antibody levels between the four groups of subjects.

Enrichment of Ace specific antibodies by elution and their effect on adherence: Recombinant Ace protein was electrophoresed in 10% NuPAGE Bis-Tris gels (NOVEX), transferred to a PVDF membrane, and incubated with *E. faecalis* endocarditis serum S0032. Ace A specific antibody elution was performed by the procedure described elsewhere (41). Inhibition of enterococcal adherence to CI, CIV, and LN with IgGs affinity purified from normal human sera or from an *E. faecalis* endocarditis patient serum S0032 was carried out as described elsewhere for rabbit sera (20). Results are presented as % of cells bound, based on the formula (radioactivity of bound cells/radioactivity of total cells added)×100.

Accession numbers of nucleotide sequences: Ace nucleotide sequences reported here were submitted to GenBank and have received Accession No. AF-159247.

Results

Figure 12D:
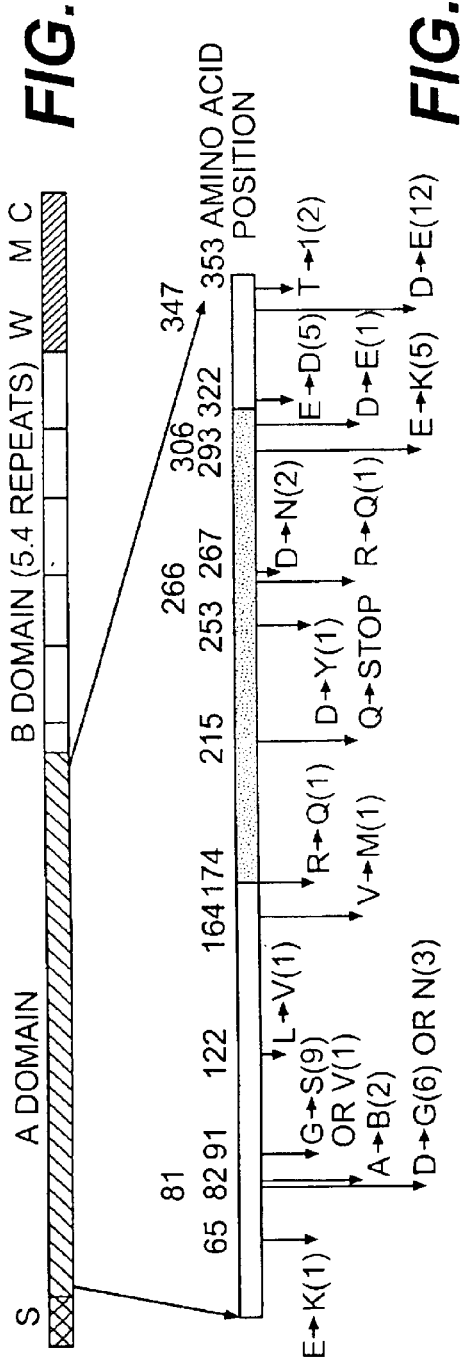

*E. faecalis* ace sequences: DNA sequencing and analysis revealed that the ace gene of *E. faecalis* OG1 RF is 2166 bp in length, encoding a putative polypeptide of 721 amino acids (FIG. 12A). As was previously reported for Ace of *E. faecalis* strain EF1, the first 31 residues have the properties of a signal peptide, with a charged region followed by hydrophobic residues (26). The N terminal region is composed of a 335 amino acid A domain, followed by a tandemly repeated B domain (FIG. 12A). In the B domain, 47 amino acids are repeated 5 times preceded by a short 20 amino acid partial repeat (FIG. 12D). Recer (recombinant sites in genes that also serve as flexible spacers in the protein) sequences previously described by de Chateau and Bjork (7), GAA AAT CcA GAT GAA (SEQ ID No. 15) coding for presumably unstructured ENPDE, were identified in the nucleotide sequence at the boundary between each B repeat. The C terminal region is composed of a cell wall domain with conserved LPKTG anchorage residues, followed by an 18 amino acid hydrophobic membrane spanning domain and a short cytoplasmic tail as previously found for EF1 (26). The predicted molecular weight of the Ace protein of OG1RF after signal peptide processing is 75.6 kDa.

The complete ace gene was also sequenced from 6 other *E. faecalis* strains shown to express adherence to CI, CIV, and LN and one strain which showed no adherence (39 and in this study) and compared to the ace sequence from E faecalis strains OG1 RF and V583 (*E. faecalis* database in progress, The Institute of Genomic Research (TIGR), Rockville, Md.). Analysis of complete ace sequences after gapped alignment revealed 77.7 to 99.8% identity at the DNA level and 77.7 to 99.7% identity at the protein level, with differences predominantly due to variation in the number of repeats in the B domain. Among these 9 strains, there were 155 nucleotide differences, of which many are silent. Signal peptide and cytoplasmic tail regions showed 100% identity at the amino acid level. The A domain, cell wall domain and membrane spanning domains were also found to be conserved with more than 95% identity. The number of repeats in the B domain were 2.4, 3.4, 4.4, and 5.4 in different strains, as shown in Table 6, for a total Ace size of 580, 627, 674 and 721 amino acids. The recer sequences were identified in B domain boundaries in all 9 strains. Further analysis of B repeat numbers among 6 other *E. faecalis* strains by PCR showed results consistent with the above mentioned four different patterns (FIG. 12B).

Since the Ace A domain was shown to be responsible for binding to CI (26), we further sequenced the 957 bp region of ace (121 bp through 1077 bp of ace) corresponding to the A domain from 17 other arbitrarily selected *E. faecalis* strains collected worldwide. Analysis of the A domain sequences from these and the other 9 *E. faecalis* strains showed differences at 46 nucleotides resulting in 16 amino acid substitutions (FIG. 12C). The percentage of identity between these 26 Ace A sequences was found to be between 97.5 and 100. Amino acids 174–319, that showed the highest degree of similarity to amino acids 151 to 338 of *S. aureus* collagen binding protein (Cna), were found to be highly conserved. Of the five amino acids that are critical for collagen binding by Cna of *S. aureus* (26, 36), tyrosine, arginine, phenylalanine, and asparagine (at positions 180, 193, 195, and 197 of Ace) were present in all the strains tested, whereas the fifth critical residue tyrosine (at position 233 in Cna of *S. aureus*, corresponding position 237 of Ace) was found to be conserved as lysine in all the 26 *E. faecalis* strains tested. One strain, *E. faecalis* SE47b, was found to have a stop codon at position 215.

Correlation of in vitro expression of Ace and of adherence: Table 6 summaries the adherence characteristics and results of probing mutanolysin-PMSF extract concentrates of 8 different strains of *E. faecalis* (as well as results with OG1 RF described in companion paper (20)), with polyclonal immune serum raised against recombinant OG1 RF Ace A. After growth at 37° C. a single ~105 kDa protein band was seen in extracts of *E. faecalis* END6 strain, and a single ~86 kDa weakly positive band for *E. faecalis* MC02152 strain (FIG. 13), whereas no band was detected in extracts of the remaining 6 strains tested. Probing of mutanolysin extracts prepared from these 8 *E. faecalis* strains grown at 46° C. with anti-Ace A antibodies showed a single reactive protein band in 6 *E. faecalis* strains (Table 6 and FIG. 13). The four observed sizes of protein bands are in concordance with the different number of B repeats (Table 6). No band was detected in extracts prepared from 37° C.

or 46° C. grown LBJ-1 and, as anticipated from sequencing data, no protein band was detected in *E. faecalis* SE47b. The adherence phenotype of these *E. faecalis* strains to CI, CIV, and LN was retested and the results are presented in Table 6. In addition to two previously reported *E. faecalis* strains END6 and SE47b, that showed adherence to collagens and/or laminin even after growth at 37° C. (39), *E. faecalis* MC02152 grown at 37° C. showed low level binding to ECM proteins (6% to CI, 8.9% to CIV, and 7.1% to LN), while the remaining *E. faecalis* strains showed <5% binding after growth at 37° C.; these latter strains were considered as adherence negative since we use 5% of cells bound as a cut off to define adherence. Seven of these strains, excluding LBJ1, showed a marked increase (to ≧20%) in adherence to CI, CIV, and LN after growth at 46° C. Of note, strain SE47b which showed significant binding to CI, CIV, and LN after growth at both 37° C. and 46° C. (39 and current study) also showed a high degree of clumping in in vitro culture conditions, which may have resulted in high counts of clumped cells, leading to a high percent of binding by a non-Ace mediated mechanism at both 37° C. and 46° C. IgGs purified from anti-Ace A rabbit immune serum were unable to inhibit adherence of SE47b (data not shown).

Reactivity of serum from humans with enterococcal Infections with Ace A recombinant protein: We initially screened several *E. faecalis* endocarditis sera by western blotting. Among 5 sera, one (S0032) showed strong reactivity, and three reacted moderately to recombinant Ace A protein, suggesting that in viva expression of ace by different strains had occurred in these patients (FIG. 14). Serum from a patient with *E. faecium* endocarditis did not react with recombinant Ace A.

We then quantitatively assayed the presence of Ace specific IgGs from the different sera groups. Nineteen of 21 (90%) *E. faecalis* endocarditis sera (including the four noted above) and 3 of 4 (75%) ESU endocarditis sera (group I) showed substantial reactivity (FIG. 15). The other three sera of the *E. faecalis* and ESU endocarditis group showed reactivity at the same levels as control sera; ELISA titers of these three sera against total enterococcal antigens were also low, ~20 to 60 fold lower than that of the other sera tested (data not shown). Titers of the reactive *E. faecalis* endocarditis sera against Ace A varied from 1:32 to >1:1024 as shown in FIG. 15. A total of 5 of 9 sera from *E. faecalis* non-endocarditis infections which included bone infections (1 of 2), urosepsis (1 of 2), line sepsis with bacteremia (1 of 1), cholangitis with bacteremia (0 of 1), cholecystitis (1 of 1), bacteremia (1 of 1), and cholelithiasis with secondary bacteremia (0 of 1) showed Ace A antibody levels greater than the cut off for the control sera levels, and all three sera from non-endocarditis ESU infections (group II sera) showed reactivity equal to controls. Of the 9 group III sera from patients with *E. faecium* and streptococcal infections (mainly endocarditis), one had elevated anti-Ace A IgG levels. The non-healthy control group (group IV) sera from hospitalized patients (HPS) reacted at levels that were the same or lower than those of normal human sera. A statistically significant difference was observed between study group 1 and group 2 versus group 3 and group 4 sera ($p<0.001$).

Ability of IgGs from endocarditis serum to inhibit adherence of *E. faecalis* OG1RF to ECM proteins: We examined the ability of IgGs purified from a high Ace A titer *E. faecalis* endocarditis patient serum S0032 (HTS) to inhibit adherence of 46° C. grown *E. faecalis* OG1 RF to CI, CIV, and LN. Preincubation of OG1 RF with IgGs from this serum at concentrations greater than 2 mg/ml inhibited adherence to CI, CIV, and LN by about 16–24 fold relative to normal human serum as shown in Table 7. Purified IgGs from normal human sera had a negligible effect on adherence at these concentrations.

To further test the involvement of human derived Ace specific antibodies, antibodies eluted from recombinant Ace A on a western blot probed with serum S0032 were used in the adherence inhibition assay. As shown in FIG. 16, 10 µg/ml of eluted antibody completely inhibited bacterial adherence to all the three ECM proteins, CI, CIV, and LN. These eluted human antibodies reacted with a single ~105 kDa band of mutanolysin-PMSF extracts of 46° C. grown OG1 RF on western blot (data not shown), similar to the rabbit anti-recombinant Ace A antibodies (20).

Lack of evidence of an ace homolog in non-*E. faecalis* species: Our recent hybridization results with 75 *E. faecalis* strains and 124 non-*E. faecalis* strains using the 1090 bp ace probe indicated that ace is specific to *E. faecalis* strains (8). Using this probe and a 419 bp conserved ace DNA probe (that represents the region with the most identity to the binding domain of Cna from *S. aureus* (26)), we tested colony lysates of 350 well characterized enterococcal isolates and showed that all 161 *E. faecalis* isolates were positive under high stringency conditions, whereas none of the 189 non-*E. faecalis* enterococcal isolates were positive even under low stringency hybridization conditions. Southern hybridization of DNA preparations from nine *E. faecium* strains with the 419 bp conserved ace DNA probe under low stringency conditions also showed no bands, further implying absence of a close ace homolog in *E. faecium*.

Discussion

Our earlier investigation has reported a conditional adherence phenotype among most *E. faecalis* isolates (39). Following this, we identified an *E. faecalis* gene, ace, that encodes a putative adhesin (Ace) and presented evidence for its role in binding to CI (26). In our companion paper, we disrupted ace gene in the laboratory strain OG1 RF and reported that Ace mediates adherence to CIV and LN in addition to CI (20).

In the current study, we examined the diversity of the ace gene in different *E. faecalis* strains. Our initial amplification of ace sequences from 15 *E. faecalis* isolates by PCR showed DNA fragments of four different sizes. To explain this observed size difference and also to investigate the extent of differences in ace sequences among *E. faecalis* isolates obtained from different sources, we sequenced the complete ace gene from eight selected *E. faecalis* strains. Comparison of nucleotide and deduced amino acid sequences of Ace from these strains with that available for V583 strain from TIGR database showed the highly conserved N-terminal regions representing the A domain, followed by variable B repeat region. Analysis of these sequences revealed that ace occurred in four different forms relating to variation in the B repeat numbers. Similarly, four molecular sizes of Ace proteins were observed on western blots probed with anti-Ace A immune rabbit serum. As reported earlier for Ace proteins from *E. faecalis* strains OG1RF (20), EF1 and EF2 (26), the observed molecular sizes of Ace detected on western blots of extracts from different *E. faecalis* strains were found to be larger than predicted sizes based on deduced amino acid sequences, perhaps due to their high acidic nature, as shown in Table 6. Consensus 15-nucleotide recer sequences were identified between each B repeat. Earlier analysis of recer sequences in *Peptostreptococcus magnus* suggested their possible role in recombination of new incoming modules at the DNA level (7). Similarly, at the protein level, the proline residues in ENPDE recer sequences have been proposed to promote lack of structure and thus allowing interdomain flexibility. No racer sequences were reported in staphylococcal collagen binding gene cna. Although we do not have any direct evidence of recombination occurring at recer sequences, this may possibly explain the variation in B repeats. We have yet to characterize the function of the B domain. Though several functions were predicted for the B domains of Cna of *S. aureus*, recent detailed studies were unable to prove any such functions (10, 25, 33). Further sequencing of the N-terminal ace region that codes for the A domain, the region we previously showed is involved in binding to CI (26), from 17 additional strains collected worldwide showed ≧97.5% identity, indicating the highly conserved nature of this functional domain. In one of these strains, *E. faecalis* SE47b, the ace gene was interrupted by a stop codon as will be discussed further below.

We also attempted to correlate the in vitro production of Ace with the observed phenotype, i.e., binding to ECM proteins CI, CIV, and LN after growth at 37° C. or 46° C. In western blots, Ace was detected in extracts of only two *E. faecalis* strains after growth at 37° C., of which one strain, END6, had been previously noted to bind to CI and CIV after growth at 37° C. (39). The other strain MC02152, which showed a faintly positive band after growth at 37° C., exhibited low level binding to CI, CIV, and LN. This is in contrast to the majority of *E. faecalis* strains (for which no band was detected after growth at 37° C.) which showed <5% binding after growth at 37° C.; since we use 5% of cells bound as a cut off to define adherence, these isolates were considered as adherence negative. Consistent with the observed binding of 46° C. grown *E. faecalis* strains to CI, CIV, and LN, the Ace protein was detected in most 46° C. grown *E. faecalis* strains. With MC02152, a much more strongly positive band was observed on the western blot after growth at 46° C., and its binding increased to 29% to CI, 38% to CIV and 41% to LN. Our companion paper also reports identification of a single ~105 kDa Ace protein band from 46° C. grown *E. faecalis* OG1 RF extracts, but not from 37° C. grown extracts (20). With E faecalis LBJ-1, we were unable to detect an Ace protein band on the western blot with extracts prepared from 37° C. or 46° C. grown cells, and it is the only strain that showed no adherence to CI, CIV, and LN after growth at either temperature. Similarly, as anticipated from sequencing data, no Ace protein band was found In extracts of SE47b, the strain whose binding was not reduced by anti-Ace A IgGs, indicating a non-Ace mediated adherence; this strain shows a high degree of clumping in broth which may explain its apparent binding to ECMs. Thus, the observed conditional expression of Ace protein correlates with conditional adherence (i.e., after growth at 46° C.) of *E. faecalis* strains (39). Since adhesin genes of other pathogenic bacteria have shown to be environmentally regulated (14, 21, 38), the absence of in vitro production of Ace at 37° C. is not unprecedented.

In an effort to determine if there was evidence of Ace expression under physiological conditions, we analyzed the antibody levels to recombinant Ace A using a diversified serum collection from patients from different medical centers with various types of infections caused by different strains. Our results showed significantly higher anti-Ace A IgG levels among most sera obtained from *E. faecalis* endocarditis patients as well as in some sera from other *E. faecalis* infections. The two *E. faecalis* endocarditis sera that were non-reactive with Ace had much lower total enterococcal antibody levels. Since we lack information about the time of sera collection relative to the onset of illness, it is possible that these negative sera were drawn early in infection. One of 6 sera from *E. faecium* endocarditis patients also showed reactivity to Ace A protein. Since Southern hybridization of genomic DNA isolated from this strain with the ace probes, even under low stringency conditions, showed absence of any hybridization, these antibodies may be the result of a prior infection with *E. faecalis*. It is of interest that the endocarditis-serum from the patient infected with LBJ-1 had Ace A antibodies (titer, 1:256). As described earlier, this strain showed neither conditional adherence nor in vitro Ace expression by western blots, but the presence of antibodies suggests that Ace was expressed at the time of infection or, possibly, during some prior infection. These results indicate that Ace is commonly expressed in vivo, during infection by different strains. Similar to our findings that suggest Ace is produced in vivo, though usually not at levels detectable by our assays when grown at 37° C. in vitro, we have observed other antigens that reacted with sera from patients with enterococcal infections but not with rabbit polyclonal serum raised against protein extracts from a 37° C. grown *E. faecalis* endocarditis isolate (40). We have also observed this with the polysaccharide gene cluster of *E. faecalis* for which we have evidence of in vivo, but not in vitro, production, except for an unusual mucoid strain, which expresses a polysaccharide antigen at a lower temperature (42).

In the bacterial ECM adherence assay, inhibition was obtained with IgGs from a high Ace A titer *E. faecalis* endocarditis patient serum S0032 and with Ace A specific eluted antibodies derived from this serum. The eluted Ace specific antibodies reacted only with a ~105 kDa band from extracts of 46° C. (but not 37° C.) grown OG1RF, indicating the specificity of the eluted antibodies. Recent studies on antibody response to fibronectin binding protein A in patients with *S. aureus* infections detected considerable variation in IgG levels that reacted with the ligand binding repeat domain of FnBpA. However, these antibodies were unable to block fibronectin binding (4).

Our recent study suggested usefulness of ace in species identification (8). In the present study, we included more *E. faecalis* isolates obtained from different geographical regions and from different clinical sites. We confirmed that ace is specific to *E. faecalis*, as none of the non-*E. faecalis* enterococcal isolates hybridized to an ace probe even under low stringency conditions, and is present in all isolates regardless of their clinical source; this is different from what is seen with the staphylococcal ace homolog, cna (encoding a collagen binding adhesin of *S. aureus*), which is present in only 38–56% *S. aureus* strains (27, 32, 35). The absence of hybridization using low stringency conditions is in contrast to our identification of homologs in *E. faecium* of other *E. faecalis* genes (e.g., efaA (31) and a polysaccharide gene cluster (unpublished observation) using low stringent hybridization conditions.

In conclusion, analysis of ace sequences from *E. faecalis* strains collected from patients worldwide showed that the *E. faecalis* specific gene, ace, occurs in at least four different forms, with ≧97.5% identity in the region encoding the A domain and more apparent variation in the region coding for the B domain, due to variation in the number of repeats. Conditional (after growth at 46° C.) in vitro expression of Ace, detected using polyclonal antibodies to OG1 RF derived recombinant Ace A, correlated with our previously described conditional adherence of these *E. faecalis* strains to ECM proteins. Identification of Ace specific antibodies in sera obtained from patients with enterococcal infections, especially patients with *E. faecalis* endocarditis, indicates that Ace is commonly expressed in vivo during infection in man, not just at 46° C. in vitro. Investigation of a possible role for Ace in pathogenesis and elucidation of whether the ability of these antibodies to block adherence of E. faecalis to ECM proteins has any potential protective effects in vivo will be the subject of our future studies.

TABLE 5

Oligonucleotide primers used in this study

| Oligonucleotide | Forward primer sequences (5'–3') | Location[a] |
|---|---|---|
| AceF1 | CTATTGTCAACTTCTGAAAAAG | −68 to −47 |
| AceF2 | GAGCAAAAGTTCAATCGTTGAC | 99 to 120 |
| AceF2a | TCACCAATAGTTCTCAACCG | 410 to 429 |
| AceF3 | CCAAATTGAGCGAGACTATC | 510 to 529 |
| AceF3a | CACTTGCCGAGTTTGAGC | 719 to 736 |
| AceBF1 | AAAATGTGGAAATGCCAACAGAAGAAAGTC | 986 to 1015 |
| AceF5 | AGTGAAAAGACAGACACAACA | 1087 to 1107 |
| AceF6 | AAATGAAGGAAGCCCACAG | 1836 to 1854 |

| Oligonucleotide | Reverse primer sequences (5'–3') | Location[a], complementary strand |
|---|---|---|
| AceR1a | GAGAACTATTGGTGATAAGCG | 424 to 404 |
| AceR2 | CATTCGTTGCGTCTTGATTG | 928 to 909 |
| AceR3 | GTCTGTCTTTTCACTTGTTTCT | 1101 to 1080 |
| AceR3a | GGTTTTTCAGGTAGGATTGG | 1499 to 1480 |
| AceR4 | TGGCTGTTTTTTCTCAGTTGT | 1749 to 1729 |
| AceBR1 | ATTTAATTTTTGAATTGGTTCACTAAGCAG | 1896 to 1867 |
| AceBR2 | CAGCAATTTATCTCCAGATAATAGAAAAGC | 2087 to 2058 |

[a]Location of Ace primers are relative to the ATG start codon of E. faecalis strain V583. This sequence was obtained from contig 6285 of E. faecalis database (The Institute of Genomic Research, Rockville, MD).

TABLE 6

Details of ace gene sequences and predicted proteins from different E. faecalis strains as well as observed molecular weights of detected Ace proteins after growth at two different temperatures

|   | Strain | Source/Reference | ace gene size (bp) | Number of B repeats | Predicted MW (kDa)[a] | pI[b] | Observed MW (kDa) after growth at 37° C. | 46° C. | Phenotype[c] 37° C./46° C. |
|---|---|---|---|---|---|---|---|---|---|
| 1 | OG1RF | 18 | 2166 | 5.4 | 75.6 | 4.22 | —[d,e] | 105[e] | −/+ |
| 2 | JH2-2 | 12 | 1743 | 2.4 | 61.0 | 4.36 | — | 75 | −/+ |
| 3 | V583 | 28 | 2025 | 4.4 | 70.9 | 4.24 | — | 94 | −/+ |
| 4 | MC02152 | Endocarditis | 1884 | 3.4 | 65.6 | 4.29 | 86 (faint) | 86 | (+)[f]/+ |
| 5 | END6 | Endocarditis | 2166 | 5.4 | 75.8 | 4.19 | 105 | 105 | (+)[g]/+ |
| 6 | LBJ-1 | Endocarditis | 1743 | 2.4 | 60.7 | 4.40 | — | — | −/− |
| 7 | SE33 | Community | 2025 | 4.4 | 70.6 | 4.30 | — | 94 | −/+ |
| 8 | MD9 | Urine | 1884 | 3.4 | 65.6 | 4.30 | — | 86 | −/+ |
| 9 | SE47b | Community | 2025[b] | 4.4 | 20.3[i] | 4.89 | — | — | (+)[i]/(+)[j] |

[a]Predicted molecular weight was estimated after processing signal peptide sequence.
[b]pI: Isoelectric point was calculated based on predicted protein sequence deduced from ace gene sequence.
[c]Some results on binding of E. faecalis strains to ECM proteins (collagen types I and IV, and laminin) were previously reported (39).
+/− denote binding (defined as ≧ 5% bacteria bound) or lack of binding at 37° C./46° C.
[d]Protein band not seen.
[e]Results for strain OG1RF are from Nallapareddy et al. (20)).
[f]Only 6 to 9% of 37° C. grown E. faecalis MC02152 cells were bound to wells with CI, CIV and LN vs. 29 to 41% of bound cells after growth at 46° C.
[g]37° C. grown E. faecalis END6 cells were bound to CI and CIV only.
[h]Base transition C→T at nucleotide 643 introduces a stop codon at codon 215.
[i]Size predicted with stop codon.
[j]E. faecalis SE47b shows a high degree of clumping under in vitro culture conditions at both 37° C. and 46° C.; adherence was not inhibited by anti-Ace IgGs indicating a non-Ace mediated mechanism.

TABLE 7

Inhibition of adherence of 46° C. grown E. faecalis OG1RF to ECM proteins by IgGs purified from E. faecalis endocarditis patient serum with high Ace A titers

| | | IgG concentration | | | | | | | |
|---|---|---|---|---|---|---|---|---|---|
| | | 0.1 mg/ml | | 1 mg/ml | | 2 mg/ml | | 4 mg/ml | |
| ECM[a] | No IgG | NHS[b] | HTS[c] | NHS | HTS | NHS | HTS | NHS | HTS |
| CI | 25.6 ± 1.59[d] | 23.0 ± 1.40 | 23.6 ± 0.37 | 21.2 ± 0.78 | 13.5 ± 0.30 | 21.2 ± 1.94 | 1.4 ± 0.29 | 18.8 ± 0.11 | 1.0 ± 0.03 |
| CIV | 27.7 ± 0.37 | 24.8 ± 1.55 | 28.2 ± 0.32 | 25.6 ± 0.32 | 19.9 ± 0.62 | 24.0 ± 1.56 | 1.0 ± 0.25 | 25.6 ± 0.69 | 0.9 ± 0.13 |
| LN | 31.9 ± 2.37 | 31.5 ± 0.21 | 30.4 ± 2.25 | 31.3 ± 1.37 | 11.2 ± 0.48 | 31.3 ± 0.98 | 2.0 ± 0.11 | 31.4 ± 2.10 | 2.6 ± 0.25 |
| BSA | 0.6 ± 0.03 | 0.9 ± 0.02 | 0.3 ± 0.02 | 0.7 ± 0.12 | 0.7 ± 0.20 | 0.7 ± 0.09 | 0.5 ± 0.11 | 0.8 ± 0.08 | 0.5 ± 0.05 |

[a]ECM: extracellular matrix proteins; CI: collagen type I; CIV: collagen type IV; LN: laminin; BSA: bovine serum albumin.
[b]NHS: IgGs purified from pooled normal human sera collected from healthy volunteers.
[c]HTS: IgGs purified from High Ace A Titer E. faecalis endocarditis patient Serum S0032 (>1:1024).
[d]Values are means of % of cells bound ± standard deviation. Results are representative of at least two independent experiments.

FOOTNOTES

1. Abbreviations: Ace, adhesin of collagen from enterococci; BHI media, brain-heart-infusion media; BSA, bovine serum albumin; CD, circular dichroism; Cna, *Staphylococcus aureus* collagen adhesin; ECM, extracellular matrix; FITC, fluorescein isothiocyanate; HEPES, N-(2-hydroxyethyl)piperazine-N'-2-ethanesulfonic acid; IPTG, isopropyl-β-D-thiogalactoside; LB, Luria broth; MSCRAMM, microbial surface components recognizing adhesive matrix molecules; PBS, phosphate-buffered saline; PCR, polymerase chain reaction; RMS, root mean square; SDS-PAGE, sodium dodecyl sulfate-polyacrylamide gel electrophoresis; SPR, surface plasmon resonance spectroscopy; TIGR, The Institute for Genomic Research; TSB, tryptic soy broth; UV/vis, ultraviolet/visible; amino acids are represented by standard one-letter codes.

2. Sequence data for *Enterococcus faecalis* was obtained from the Institute for Genomic Research website. Sequencing of *Enterococcus faecalis* was accomplished with support from the National Institute of Allergy and Infectious Diseases.

3. The nucleotide and amino acid sequences for Ace from *E. faecalis* strain V583 have been deposited in the Genbank database under Genbank Accession Number AF1 59247.

NUMBERED REFERENCES TO SPECIFICATION AND EXAMPLE 1

1. Murray, B. E. (1990) *Clin. Microbiol. Rev.* 3, 46–65
2. Foster, T. J. and Höök, M. (1998) *Trends Microbiol.* 6, 484–488
3. Patti, J. M., Allen, B. L., McGavin, M. J., and Höök, M. (1994) *Annu. Rev. Microbiol.* 48, 585–617
4. Patti, J. M., Jonsson, H., Guss, B., Switalski, L. M., Wiberg, K., Lindberg, M., and Höök, M. (1992) *J. Biol. Chem.* 267, 4766–4772
5. Patti, J. M., Boles, J. O., and Höök, M. (1993) *Biochem.* 32, 11428–11435
6. Nilsson, I. -M., Patti, J. M., Bremell, T., Höök, M., and Tarkowski, A. (1998) *J. Clin. Invest.* 101, 2640–2649
7. Symersky, J., Patti, J. M., Carson, M., House-Pompeo, K., Teale, M., Moore, D., Jin, L., DeLucas, L. J., Höök, M., and Narayana, S. V. L. (1997) *Nat. Struct. Biol.* 10, 833–838
8. Rich, R. L., Demeler, B., Ashby, K., Deivanayagarn, C. C. S., Petrich, J. W., Patti, J. M., Narayana, S. V. L., and Höök, M. (1998) *Biochemistry* 37, 15423–15433
9. Gillaspy, A. F., Patti, J. M., Pratt, Jr., F. L., Iandolo, J. J., and Smeltzer, M. S. (1997) *Gene* 196, 239–248
10. Switalski, L. M., Patti, J. M., Butcher, W., Gristina, A. G., Speziale, P., and Höök, M. (1993) *Mol. Microbiol.* 7, 99–107
11. Patti, J. M., Bremell, T., Krajewska-Pietrasik, D., Abdelnour, A., Tarkowski, A., Rydén, C. and Höök, M. (1994) *Infect. Immun.* 62, 152–161
12. Xiao, J., Höök, M., Weinstock, G. M., and Murray, B. E. (1998) *FEMS Immun. Med. Microbial.* 21, 287–295
13. Zareba, T. W., Pascu, C., Hryniewicz, W., Wadstrom, T. (1996) *Curr. Microbiol.* 34, 6–11
14. Altschul, S. F., Maddem, T. L., Schaffer, A. A., Zhang, J., Zhang, Z., Miller, W., and Lipman, D. J. (1997) *Nuc. Acids Res.* 25, 3389–3402
15. Peitsch, M. C., (1995) *Bio/Technology* 13, 658
16. Peitsch, M. C. (1996) *Biochem. Soc. Trans.* 24, 274
17. Peitsch, M. C., Guex, N. (1997) *Electrophoresis* 18, 2714
18. Caparon, M. G. and Scott, J. R. (1987) *Proc. Natl. Acad. Sci.* 84, 8677–8681
19. Singh, K. V. Qin, X., Weinstock, G. M., and Murray, B. E. (1998) *J. Infect. Dis.* 178, 1416–1420
20. Talay, S. R., Ehrenfeld, E., Chhatwal, G. S., and Timmis, K. N. (1991) *Mol. Microbiol.* 5, 1727–1734
21. Jett, B. D., Huycke, M. M., Gilmore, M. S. (1994) *Clin. Microbiol. Rev.* 7, 462–478
22. Valentin-Weigand, P. Chhatwal, G. S., and Blobel, H. (1988) *Am. J. Vet. Res.* 49, 485–488
23. Pace, C. N., Vajdos, F., Fee, L., Grmsley, G., and Gray, T. (1995) *Prot. Sci.* 4, 2411–2423
24. Patti, J. M., House-Pompeo, K., Boles, J. O., Garza, N., Gurusiddappa, S., and Höök, M. (1995) *J. Biol. Chem.* 270, 12005–12011
25. House-Pompeo, K., Boles, J. O., and Höök, M. (1994) *METHODS: A Companion to Meth. Enzymol.* 6, 134–142
26. Schneewind, O., Model, P., and Fischetti, V. A. (1992) *Cell,* 70, 267–281
27. Sahm, D. F., Kissinger, J., Gilmore, J. S., Murray, P. R., Mulder, R., Solliday, J., Clarke, B. (1989) *Antimicrob. Agents Chemother.* 33, 1588–1591
28. Rich, R. L., Narayana, S. V. L., Owens, R. T., Carson, M., Höök, A, Yang, W. -C., Deivanayagam, C. C. S., and Höök, M. *J. Biol. Chem.* (Submitted)
29. de Château, M. and Björk, L. (1996) *Proc. Natl. Acad. Sci.* 93, 8490–8495

REFERENCES TO EXAMPLE 2

1. Beck, K., I. Hunter, and J. Engel. 1990. Structure and function of laminin: anatomy of a multidomain glycoprotein. FASEB J. 4:148–160.

2. Duh, R. W., K. V. Singh, K. Malathum, and B. E. Murray. Comparision of in vitro activity of 19 antimicrobial agents against enterococci from healthy subjects and hospitalized patients. Microbial Drurg Resistance (Submitted for publication).
3. Engel, J. 1992. Laminins and other strange proteins. Biochemistry. 31:10643–10651.
4. Ettner, N., W. Göhring, T. Sasaki, K. Mann, and R. Timpl. 1998. The N-terminal globular domain of the laminin α1 chain binds to α1β1 and α2β1 integrins and to the heparan sulfate-containing domains of perlecan. FEBS Lett. 430:217–221.
5. Flügel, A., H. Schulze-Koops, J. Heesemann, K. Kühn, L. Sorokin, H. Burkhardt, K. von der Mark, and F. Emmrich. 1994. Interaction of enteropathogenic *Yersinia enterocolitica* with complex basement membranes and the extracellular matrix proteins collagen type IV, laminin-1 and -2, and nidogen/entactin. J. Biol. Chem. 269:29732–29738.
6. Foster, T. J., and M. Höok. 1998. Surface protein adhesins of *Staphylococcus aureus*. Trends Microbiol. 6:484–488.
7. Gehisen, K. R., L. Dillner, E. Engvall, and E. Ruoslahti. 1988. The human laminin receptor is a member of the integrin family of cell adhesion receptors. Science. 241:1228–1229.
8. Harlow, E., and D. Lane. 1988. Antibodies: a laboratory manual. Cold Spring Harbor Laboratory Press, Cold Spring Harbor, N.Y.
9. Juarez, Z. E., and M. W. Stinson. 1999. An extracellular protease of *Streptococcus gordonii* hydrolyzes type IV collagen and collagen analogues. Infect Immun. 67:271–278.
10. Lantz, M. S., R. D. Allen, P. Bounelis, L. M. Switalski, and M. Höok. 1990. *Bacteroides gingivalis* and *Bacteroides intermedius* recognize different sites on human fibrinogen. J. Bacteriol. 172:716–726.
11. Lantz, M. S., R. D. Allen, L. W. Duck, J. L. Blume, L. M. Switalski, and M. Höok. 1991. Identification of *Porphyromonas gingivalis* components that mediate its interactions with fibronectin. J. Bacteriol. 173:4263–4270.
12. Li, X., G. M. Weinstock, and B. E. Murray. 1995. Generation of auxotrophic mutants of *Enterococcus faecalis*. J. Bacteriol. 177:6866–6873.
13. Lindmark, H., and B. Guss. 1999. SFS, a novel fibronectin-binding protein from *Streptococcus equi*, inhibits the binding between fibronectin and collagen. Infect Immune. 67:2383–2388.
14. Ljungh, A., A. P. Moran, and T. Wadström. 1996. Interactions of bacterial adhesins with extracellular matrix and plasma proteins: pathogenic implications and therapeutic possibilities. FEMS Immunol Med Microbiol. 16:117–126.
15. Lopes, J. D., M. dos Reis, and R. R. Brentani. 1985. Presence of laminin receptors in *Staphylococcus aureus*. Science. 229:275–277.
16. McGavin, M. H., D. Krajewska-Pietrasik, C. Rydén, and M. Höok. 1993. Identification of a *Staphylococcus aureus* extracellular matrix-binding protein with broad specificity. Infect Immun. 61:2479–2485.
17. Miller, E. J., and S. Gay. 1987. The collagens: an overview and update. Methods Enzymol. 144:3–41.
18. Murray, B. E., K. V. Singh, J. D. Heath, B. R. Sharma, and G. M. Weinstock. 1990. Comparison of genomic DNAs of different enterococcal isolates using restriction endonucleases with infrequent recognition sites. J Clin Microbiol. 28:2059–2063.
19. Murray, B. E., K. V. Singh, R. P. Ross, J. D. Heath, G. M. Dunny, and G. M. Weinstock. 1993. Generation of restriction map of *Enterococcus faecalis* OG1 and investigation of growth requirements and regions encoding biosynthetic function. J. Bacteriol. 175:5216–5223.
20. Nallapareddy, S. R., K. V. Singh, R. W. Duh, G. M. Weinstock, and B. E. Murray. Diversity of ace, a gene encoding an MSCRAMM, from different strains of *Enterococcus faecalis* and evidence for production of Ace during human infections. Infect Immun. (Submitted for publication).
21. Patti, J. M., H. Jonsson, B. Guss, L. M. Switalski, K. Wiberg, M. Lindberg, and M. Höok. 1992. Molecular characterization and expression of a gene encoding a *Staphylococcus aureus* collagen adhesin. J Biol C hem. 267:4766–4772.
22. Pfaff, M., W. Göohring, J. C. Brown, and R. Timpl. 1994. Binding of purified collagen receptors (α1β1, α2β1) and RGD-dependent integrins to laminins and laminin fragments. Eur J. Biochem. 225:975–984.
23. Qin, X., F. Teng, Y. Xu, K. V. Singh, G. M. Weinstock, and B. E. Murray. 1998. Targeted mutagenesis of enterococcal genes. Methods in Cell Science. 20:21–33.
24. Rich, R. L., B. Demeler, K. Ashby, C. C. S. Deivanayagam, J. W. Petrich, J. M. Patti, S. V. L. Narayana, and M. Höok. 1998. Domain structure of the *Staphylococcus aureus* collagen adhesin. Biochemistry. 37:15423–15433.
25. Rich, R. L., B. Kreikemeyer, R. T. Owens, S. LaBrenz, S. V. L. Narayana, G. M. Weinstock, B. E. Murray, and M. Höok. 1999. Ace is a collagen-binding MSCRAMM from *Enterococcus faecalis*. J. Biol. Chem. 274:26939–26945.
26. Sahm, D. F., J. Kissinger, M. S. Gilmore, P. R. Murray, R. Mulder, J. Solliday, and B. Clarke. 1989. In vitro susceptibility studies of vancomycin-resistant *Enterococcus faecalis*. Antimicrob Agents Chemother. 33:1588–1591.
27. Sambrook, J., E. F. Fritsch, and T. Maniatis. 1989. Molecular cloning: a laboratory manual, 2nd ed. Cold Spring Harbor Laboratory Press, Cold Spring Harbor, N.Y.
28. Schulze-Koops, H., H. Burkhardt, J. Heesemann, K. von der Mark, and F. Emmrich. 1992. Plasmid-encoded outer membrane protein YadA mediates specific binding of enteropathogenic yersiniae to various types of collagen. Infect Immun. 60:2153–2159.
29. Singh, K. V., X. Qin, G. M. Weinstock, and B. E. Murray. 1998. Generation and testing of mutants of *Enterococcus faecalis* in a mouse peritonitis model. J Infect Dis. 178:1416–1420.
30. Skumik M., Y. el Tahir, M. Saarinen, S. Jalkanen, and P. Toivanen. 1994. YadA mediates specific binding of enteropathogenic *Yersinia enterolitica* to human intestinal submucosa. Infect Immun. 62:1252–1261.
31. Spellerberg, B., E. Rozdzinski, S. Martin, J. Weber-Heynemann, N. Schnitzler, R. Lütticken, and A. Podbielski. 1999. Lmb, a protein with similarities to the Lral adhesin family, mediates attachment of *Streptococcus agalactiae* to human laminin. Infect Immun. 67:871–878.
32. Speziale, P., G. Raucci, L. Visai, L. M. Switalski, R. Timpl, and M. Höok. 1986. Binding of collagen to *Staphylococcus aureus* Cowan 1. J. Bacteriol. 167:77–81.
33. Sung, U., J. J. O'Rear, and P. D. Yurchenco. 1993. Cell and heparin binding in the distal long arm of laminin: identification of active and cryptic sites with recombinant and hybrid glycoprotein. J. Cell Biol. 123:1255–1268.
34. Switalski, L. M., H. Murchison, R. Timpl, R. Curtiss III, and M. Höok. 1987. Binding of laminin to oral and endocarditis strains of viridans streptococci. J. Bacteriol. 169:1095–1101.

35. Switalski, L. M., P. Speziale, and M. Höök. 1989. Isolation and characterization of a putative collagen receptor from *Staphylococcus aureus* strain Cowan 1. J. Biol. Chem. 264:21080–21086.

36. Switalski, L. M., P. Speziale, M. Höök, T. Wadström, and R. Timpl. 1984. Binding of *Streptococcus pyogenes* to laminin. J. Biol. Chem. 259:3734–3738.

37. Symersky, J., J. M. Patti, M. Carson, K. House-Pompeo, M. Teale, D. Moore, L. Jin, A. Schneider, L. J. DeLucas, M. Höök, and S. V. L. Narayana. 1997. Structure of the collagen-binding domain from a *Staphylococcus aureus* adhesin. Nat Struct Biol. 4:833–838.

38. Tertti, R., M. Skurnik, T. Vartio, and P. Kuusela. 1992. Adhesion protein YadA of *Yersinia* species mediates binding of bacteria to fibronectin. Infect Immun. 60:3021–3024.

39. Westerlund, B., and T. K. Korhonen. 1993. Bacterial proteins binding to the mammalian extracellular matrix. Mol Microbiol. 9:687–694.

40. Xiao, J., M. Höök, G. M. Weinstock, and B. E. Murray. 1998. Conditional adherence of *Enterococcus faecalis* to extracellular matrix proteins. FEMS Immunol Med Microbiol. 21:287–295.

41. Yurchenco, P. D., and J. C. Schittny. 1990. Molecular architecture of basement membranes. FASEB J. 4:1577–1590.

REFERENCES TO EXAMPLE 3

1. Arduino, R. C., B. E. Murray, and R. M. Rakita. 1994. Roles of antibodies and complement in phagocytic killing of enterococci. Infect Immun. 62:987–993.

2. Beachey, E. H. 1981. Bacterial adherence: adhesin-receptor interactions mediating the attachment of bacteria to mucosal surface. J Infect Dis. 143:325–345.

3. Bodén, M. K., and J. I. Flock. 1994. Cloning and characterization of a gene for a 19 kDa fibrinogen-binding protein from *Staphylococcus aureus*. Mol Microbiol. 12:599–606.

4. Casolini, F., L. Visai, D. Joh, P. G. Conaldi, A. Toniolo, M. Höök, and P. Speziale. 1998. Antibody response to fibronectin-binding adhesin FnbpA in patients with *Staphylococcus aureus* infections. Infect Immun. 66:5433–5442.

5. Cheung, A. I., S. J. Projan, R. E. Edelstein, and V. A. Fischetti. 1995. Cloning, expression, and nucleotide sequence of a *Staphylococcus aureus* gene (fbpA) encoding a fibrinogen-binding protein. Infect Immun. 63:1914–1920.

6. Coque, T. M., J. E. Patterson, J. M. Steckelberg, and B. E. Murray. 1995. Incidence of hemolysin, gelatinase, and aggregation substance among enterococci isolated from patients with endocarditis and other infections and from feces of hospitalized and community-based persons. J Infect Dis. 171:1223–1229.

7. de Chateau, M., and L. Björck. 1996. Identification of interdomain sequences promoting the intronless evolution of a bacterial protein family. Proc Natl Acad Sci USA 93:8490–8495.

8. Duh, R. W., K. V. Singh, K. Malathum, and B. E. Murray. Comparision of in vitro activity of 19 antimicrobial agents against enterococci from healthy subjects and hospitalized patients. Microbial Drug Resistance (Submitted for publication).

9. Foster, T. J., and M. Höök. 1998. Surface protein adhesins of *Staphylococcus aureus*. Trends Microbiol. 6:484–488.

10. Gillaspy, A. F., C. Y. Lee, S. Sau, A. L. Cheung, and M. S. Smeltzer. 1998. Factors affecting the collagen binding capacity of *Staphylococcus aureus*. Infect Immun. 66:3170–3178.

11. Gordillo, M. E., K. V. Singh, and B. E. Murray. 1993. Comparison of ribotyping and pulsed-field gel electrophoresis for subspecies differentiation of strains of *Enterococcus faecalis*. J Clin Microbiol. 31:1570–1574.

12. Jacob, A. E., and S. J. Hobbs. 1974. Conjugal transfer of plasmid-borne multiple antibiotic resistance in *Streptococcus faecalis* var. *zymogenes*. J. Bacteriol. 117:360–372.

13. Jönsson, K., C. Signäs, H. P. Müller, and M. Lindberg. 1991. Two different genes encode fibronectin binding proteins in *Staphylococcus aureus*. The complete nucleotide sequence and characterization of the second gene. Eur J Biochem. 202:1041–1048.

14. Lee, C. A., and S. Falkow. 1990. The ability of *Salmonella* to enter mammalian cells is affected by bacterial growth state. Proc Natl Acad Sci USA 87:4304–4308.

15. Malathum, K., K. V. Singh, G. M. Weinstock, and B. E. Murray. 1998. Repetitive sequence-based PCR versus pulsed-field gel electrophoresis for typing of *Enterococcus faecalis* at the subspecies level. J Clin Microbiol. 36:211–215.

16. Murray, B. E. 1990. The life and times of the *Enterococcus*. Clin Microbiol Rev. 3:46–65.

17. Murray, B. E., K. V. Singh, J. D. Heath, B. R. Sharma, and G. M. Weinstock. 1990. Comparison of genomic DNAs of different enterococcal isolates using restriction endonucleases with infrequent recognition sites. J Clin Microbiol. 28:2059–2063.

18. Murray, B. E., K. V. Singh, R. P. Ross, J. D. Heath, G. M. Dunny, and G. M. Weinstock. 1993. Generation of restriction map of *Enterococcus faecalis* OG1 and investigation of growth requirements and regions encoding biosynthetic function. J. Bacteriol. 175:5216–5223.

19. Murray, B. E., and G. M. Weinstock. 1999. Enterococci: new aspects of an old organism. Proc Assoc Am Physicians. 111:328–334.

20. Nallapareddy, S. R., X. Qin, G. M. Weinstock, M. Höök, and B. E. Murray. The *Enterococcus faecalis* adhesin, Ace, mediates attachment to ECM proteins collagen type IV and laminin as well as collagen type I. Infect Immun. (Submitted for publication).

21. Olsén, A., A. Arnqvist, M. Hammar, S. Sukupolvi, and S. Normark. 1993. The RpoS sigma factor relieves H-NS-mediated transcriptional repression of csgA, the subunit gene of fibronectin-binding curli in *Escherichia coli*. Mol Microbiol. 7:523–536.

22. Patti, J. M., B. L. Allen, M. J. McGavin, and M. Höök. 1994. MSCRAMM-mediated adherence of microorganisms to host tissues. Annu Rev Microbiol: 48:585–617.

23. Patti, J. M., H. Jonsson, B. Guss, L. M. Switalski, K. Wiberg, M. Lindberg, and M. Höök. 1992. Molecular characterization and expression of a gene encoding a *Staphylococcus aureus* collagen adhesin. J. Biol. Chem. 267:4766–4772.

24. Qin, X., F. Teng, Y. Xu, K. V. Singh, G. M. Weinstock, and B. E. Murray. 1998. Targeted mutagenesis of enterococcal genes. Methods in Cell Science. 20:21–33.

25. Rich, R. L., B. Demeler, K. Ashby, C. C. S. Deivanayagam, J. W. Petrich, J. M. Patti, S. V. L. Narayana, and M. Höök. 1998. Domain structure of the *Staphylococcus aureus* collagen adhesin. Biochemistry. 37:15423–15433.

26. Rich, R. L., B. Kreikemeyer, R. T. Owens, S. LaBrenz, S. V. L. Narayana, G. M. Weinstock, B. E. Murray, and M. Höök. 1999. Ace is a collagen-binding MSCRAMM from *Enterococcus faecalis*. J. Biol. Chem. 274:26939–26945.

27. Ryding, U., J. I. Flock, M. Flock, B. Söderquist, and B. Christensson. 1997. Expression of collagen-binding protein and types 5 and 8 capsular polysaccharide in clinical isolates of *Staphylococcus aureus*. J Infect Dis. 176:1096–1099.
28. Sahm, D. F., J. Kissinger, M. S. Gilmore, P. R. Murray, R. Mulder, J. Solliday, and B. Clarke. 1989. in vitro susceptibility studies of vancomycin-resistant *Enterococcus faecalis*. Antimicrob Agents Chemother. 33:1588–1591.
29. Sambrook, J., E. F. Fritsch, and T. Maniatis. 1989. Molecular cloning: a laboratory manual, 2nd ed. Cold Spring Harbor Laboratory Press, Cold Spring Harbor, N.Y.
30. Signäs, C., G. Raucci, K. Jönsson, P. E. Lindgren, G. M. Anantharamaiah, M. Höök, and M. Lindberg. 1989. Nucleotide sequence of the gene for a fibronectin-binding protein from *Staphylococcus aureus*: use of this peptide sequence in the synthesis of biologically active peptides. Proc Natl Acad Sci USA. 86:699–703.
31. Singh, K. V., T. M. Coque, G. M. Weinstock, and B. E. Murray. 1998. In vivo testing of an *Enterococcus faecalis* efaA mutant and use of efaA homologs for species identification. FEMS Immunol Med Microbiol. 21:323–331.
32. Smeltzer, M. S., A. F. Gillaspy, F. L. Pratt, Jr., M. D. Thames, and J. J. Iandoio. 1997. Prevalence and chromosomal map location of *Staphylococcus aureus* adhesin genes. Gene. 196:249–259.
33. Snodgrass, J. L., N. Mohamed, J. M. Ross, S. Sau, C. Y. Lee, and M. S. Smeltzer. 1999. Functional analysis of the *Staphylococcus aureus* collagen adhesin B domain. Infect Immun. 67:3952–3959.
34. Sulaiman, A., R. M. Rakita, R. C. Arduino, J. E. Patterson, J. M. Steckelberg, K. V. Singh, and B. E. Murray. 1996. Serological investigation of enterococcal infections using western blot. Eur J Clin Microbiol Infect Dis. 15:826–829.
35. Switalski, L. M., J. M. Patti, W. Butcher, A. G. Gristina, P. Speziale, and M. Höök. 1993. A collagen receptor on *Staphylococcus aureus* strains isolated from patients with septic arthritis mediates adhesion to cartilage. Mol Microbiol. 7:99–107.
36. Symersky, J., J. M. Patti, M. Carson, K. House-Pompeo, M. Teale, D. Moore, L. Jin, A. Schneider, L. J. DeLucas, M. Höök, and S. V. L Narayana. 1997. Structure of the collagen-binding domain from a *Staphylococcus aureus* adhesin. Nat Struct Biol. 4:833–838.
37. Tomayko, J. F., and B. E. Murray. 1995. Analysis of *Enterococcus faecalis* isolates from intercontinental sources by multilocus enzyme electrophoresis and pulsed-field gel electrophoresis. J Clin Microbiol. 33:2903–2907.
38. VanHeyningen, T., G. Fogg, D. Yates, E. Hanski, and M. Caparon. 1993. Adherence and fibronectin binding are environmentally regulated in the group A streptococci. Mol Microbiol. 9:1213–1222.
39. Xiao, J., M. Höök, G. M. Weinstock, and B. E Murray. 1998. Conditional adherence of *Enterococcus faecalis* to extracellular matrix proteins. FEMS Immunol Med Microbiol. 21:287–295.
40. Xu, Y., L. Jiang, B. E. Murray, and G. M. Weinstock. 1997. *Enterococcus faecalis* antigens in human infections. Infect Immun. 65:4207–4215.
41. Xu, Y., B. E. Murray, and G. M. Weinstock. 1998. A cluster of genes involved in polysaccharide biosynthesis from *Enterococcus faecalis* OG1 RF. Infect Immun. 66:4313–4323.
42. Xu, Y., K. V. Singh, X. Qin, B. E. Murray, and G. M. Weinstock. 2000. Analysis of a gene cluster of *Enterococcus faecalis* involved in polysaccharide biosynthesis. Infect Immun 68:815–823.

What is claimed is:

1. An isolated nucleic acid sequence as set forth in sequence SEQ ID NO:2.

2. An isolated nucleic acid sequence coding for the collagen binding protein having the amino acid sequence as set forth in SEQ ID NO: 1.

3. An isolated nucleic acid sequence comprising nucleotides 520 to 957 of SEQ ID NO: 2.

4. An isolated nucleic acid sequence coding for the A domain of the collagen binding Ace protein from *Enterococcus facalis* wherein the A domain comprises the amino acids 174–319 of SEQ ID NO:1.

* * * * *

UNITED STATES PATENT AND TRADEMARK OFFICE
CERTIFICATE OF CORRECTION

PATENT NO. : 6,908,994 B1
APPLICATION NO. : 09/568470
DATED : June 21, 2005
INVENTOR(S) : Rich et al.

It is certified that error appears in the above-identified patent and that said Letters Patent is hereby corrected as shown below:

Please insert the following new Section after Column 1, line 5:

STATEMENT REGARDING FEDERALLY SPONSORED RESEARCH OR DEVELOPMENT:
This invention was made with Government support under Contract AR44415 awarded by NIH. The government has certain rights in this invention.

Signed and Sealed this

Thirtieth Day of January, 2007

JON W. DUDAS
*Director of the United States Patent and Trademark Office*

UNITED STATES PATENT AND TRADEMARK OFFICE
CERTIFICATE OF CORRECTION

PATENT NO.       : 6,908,994 B1                                    Page 1 of 1
APPLICATION NO.  : 09/568470
DATED            : June 21, 2005
INVENTOR(S)      : Rich et al.

It is certified that error appears in the above-identified patent and that said Letters Patent is hereby corrected as shown below:

Please insert the following new Section after Column 1, line 5:

STATEMENT REGARDING FEDERALLY SPONSORED RESEARCH OR DEVELOPMENT:
   This invention was made with Government support under Contract Nos: AR44415 and AI33516 awarded by NIH. The government has certain rights in this invention.

Signed and Sealed this

Second Day of June, 2009

JOHN DOLL
*Acting Director of the United States Patent and Trademark Office*